US012196756B2

(12) United States Patent
Gidwani et al.

(10) Patent No.: US 12,196,756 B2
(45) Date of Patent: Jan. 14, 2025

(54) LECTIN-BASED DIAGNOSTICS OF CANCERS

(71) Applicant: Kaivogen Oy, Turku (FI)

(72) Inventors: Kamlesh Gidwani, Shahganj (IN); Kim Pettersson, Turku (FI); Henna Kekki, Porvoo (FI)

(73) Assignee: UNIOGEN OY, Turku (FI)

( * ) Notice: Subject to any disclaimer, the term of this patent is extended or adjusted under 35 U.S.C. 154(b) by 1422 days.

(21) Appl. No.: 16/318,035

(22) PCT Filed: Jul. 14, 2017

(86) PCT No.: PCT/FI2017/050541
§ 371 (c)(1),
(2) Date: Jan. 15, 2019

(87) PCT Pub. No.: WO2018/011474
PCT Pub. Date: Jan. 18, 2018

(65) Prior Publication Data
US 2021/0278411 A1 Sep. 9, 2021

(30) Foreign Application Priority Data
Jul. 14, 2016 (FI) ....................................... 20165588

(51) Int. Cl.
G01N 33/574 (2006.01)
(52) U.S. Cl.
CPC ............. *G01N 33/57438* (2013.01); *G01N 33/57415* (2013.01); *G01N 33/57419* (2013.01); *G01N 33/57434* (2013.01); *G01N 2333/4724* (2013.01)

(58) Field of Classification Search
None
See application file for complete search history.

(56) References Cited

U.S. PATENT DOCUMENTS

| 5,075,218 | A | 12/1991 | Jette et al. |
| 5,126,243 | A | 6/1992 | DelVillano, Jr. et al. |
| 9,594,078 | B2 | 3/2017 | Choi et al. |
| 2004/0219690 | A1 | 11/2004 | Choi et al. |
| 2009/0131773 | A1 | 5/2009 | Struve et al. |
| 2010/0028418 | A1 | 2/2010 | Van et al. |
| 2010/0081214 | A1 | 4/2010 | Choi et al. |
| 2012/0003756 | A9 | 1/2012 | Choi et al. |
| 2012/0165221 | A1* | 6/2012 | Landstein ........ G01N 33/57438 435/7.92 |
| 2012/0251557 | A1 | 10/2012 | Van et al. |
| 2014/0186853 | A1 | 7/2014 | Yamashita et al. |

FOREIGN PATENT DOCUMENTS

| EP | 0274264 A1 | 7/1988 |
| EP | 2565268 A1 | 3/2013 |
| EP | 2722670 A1 | 4/2014 |
| JP | S62257063 A | 11/1987 |
| JP | S 63-159763 A | 7/1988 |
| JP | H 2-107967 A | 4/1990 |
| JP | 2006525527 A | 11/2006 |
| JP | 2013006801 A | 1/2013 |
| JP | 2014-183839 A | 10/2014 |
| KR | 20140011760 A | 1/2014 |
| WO | 2006061208 A1 | 6/2006 |
| WO | 2008007941 A1 | 1/2008 |
| WO | 2008040362 A2 | 4/2008 |
| WO | 2012173228 A1 | 12/2012 |
| WO | 2017005974 A1 | 1/2017 |

OTHER PUBLICATIONS

Saeland et al (Int J Cancer. Jul. 1, 2012;131(1):117-28. Epub Nov. 28, 2011) (Year: 2012).*
Waiker et al (J Am Soc Nephrol. Jan. 2012; 23(1): 13-21) (Year: 2012).*
Brooks (Genome Res. Feb. 2012;22(2):183-7) (Year: 2012).*
Baghbanian et al (Gastroenterol Hepatol Bed Bench 2013;6(1):32-35) (Year: 2013).*
Juang et al (Urological Science 25 (2014) 28-30) (Year: 2014).*
A. Belo, "The Sweet and Sorrow of Pancreatic Cancer 'Galectin-4 and Glycosylation in Pancreatic Cancer'", PhD Thesis, Molecular Cell Biology and Immunology Department, VUMC, Apr. 2, 2015, pp. 13-30.
Office Action issued on Jun. 29, 2021, by the Japanese Patent Office in corresponding Japanese Patent Application No. 2019-523186, and an English Translation of the Office Action. (6 pages).
Beatson, et al., "The Breast Cancer-Associated Glycoforms of MUC1, MUC1-Tn and sialyl-Tn, Are Expressed in COSMC Wild-Type Cells and Bind the CType Lectin MGL", PLOS One, May 2015, pp. 1-21.
Bogdan, et al., "Glycodendrimer coated gold nanoparticles for proteins detection based on surface energy transfer process", RSC Adv., Jan. 2012, pp. 985-991, vol. 2, No. 3.
Cazet, et al., "Tumour-associated carbohydrate antigens in breast cancer", Breast Cancer Research, Jan. 2010, pp. 1-13.
Duffy, et al., "CA 15-3: Uses and limitation as a biomarker for breast cancer", Clinica Chimica Acta 411, 2010, pp. 1869-1874.
Dumych et al., "Visualization of melanoma tumor with lectin-conjugated rare-earth doped fluoride nanocrystals", Croat Med J., 2014, pp. 186-194, vol. 55.
Feinberg, et al., "Multiple Modes of Binding Enhance the Affinity of DC-SIGN for High Mannose N-Linked Glycans Found on Viral Glycoproteins", Journal of Biological Chemistry, Nov. 2006, pp. 4202-4209, vol. 282, No. 6.
Fromell, et al., "Nanoparticle decorated surfaces with potential use in glycosylation analysis", Colloids and Surfaces B: Biointerfaces 46, 2005, pp. 84-91.
Gidwani, et al., "A Nanoparticle-Lectin Immunoassay Improves Discrimination of Serum CA125 from Malignant and Benign Sources", Clinical Chemistry, Oc. 2016, pp. 1390-1400, vol. 62, No. 10.

(Continued)

*Primary Examiner* — Brian Gangle
*Assistant Examiner* — Andrea K McCollum
(74) *Attorney, Agent, or Firm* — Buchanan Ingersoll & Rooney PC

(57) ABSTRACT

The present disclosure relates to non-invasive diagnostics of cancers, such as breast cancer, colorectal cancer, pancreatic cancer and prostate cancer, on the basis of altered glycosylation patterns of cancer-associated biomarkers.

12 Claims, 22 Drawing Sheets

(56) References Cited

OTHER PUBLICATIONS

Guo, et al., "Structura l basis for distinct ligand-binding and targeting properties of the receptors DC-SIGN and DC-SIGNR", Nat. Struct. Mol. Biol, Jul. 2004, pp. 591-589, vol. 11, No. 7.
International Search Report (PCT/ISA/210) mailed on Nov. 27, 2017, by the European Patent Office as the International Searching Authority for International Application No. PCT/FI2017/050541.
Liu, et al., "A rapid and simple approach for glycoform analysis", Analytica Chimica Acta 865, 2015, pp. 71-75.
Llop, et al., "Improvement of Prostate Cancer Diagnosis by Detecting PSA Glycosylation-Specific Changes", Theranosti CS, Jan. 2016, pp. 1190-1204, vol. 6, No. 8.
Maolanon, et al., "Mucin glyco-profiling by magnetic bead capture approach and its predictive biomarker value in breast- and colorectal cancer", 2015 SFG Annual Meeting, Meeting Abstracts, pp. 1283-1284.
Munkley, et al., "The role of glycans in the development and progression of prostate cancer", Nature Reviews, Urology, Apr. 2016, pp. 324-333, vol. 13, No. 6.
Pinto, et al., "Identification of new cancer biomarkers based on aberrant mucin glycoforms by in situ proximity ligation", J. Cell. Mol. Med., 2012, pp. 1474-1484, vol. 16, No. 7.
Poruk, et al., "The Clinical Utility of CA 19-9 in Pancreatic Adenocarcinoma: Diagnostic and Prognostic Updates", Current Molecular Medicine, Mar. 2013, pp. 340-351.
Saeland, et al., "Differential glycosylation of MUC1 and CEACAM5 between normal mucosa and tumour tissue of colon cancer patients", International Journal of Cancer, Nov. 2011, pp. 117-128, vol. 131, No. 1.
Saeland, et al., "The C-type lectin MGL expressed by dendritic cells detects glycan changes on MUC1 in colon carcinoma", Cancer Immunol Immunother, 2007, pp. 1225-1236.
Saeland, et al., "The C-type lectin MGL expressed by dendritic cells detects glycan changes on MUCl in colon carcinoma", Cancer Immunology, Immunotherapy, Dec. 2006, pp. 1225-1236, vol. 56, No. 8.
Soukka, et al., "Utilization of Kinetically Enhanced Monovalent Binding Affinity by Immunoassays Based on Multivalent Nanoparticle-Antibody Bioconjugates", Anal. Chem., 2001, pp. 2254-2260, vol. 73.
Syed, et al., "Role of lectin microarrays in cancer diagnosis", PROTEOMICS, Apr. 2016, pp. 1257-1265, vol. 16, No. 8.
Written Opinion (PCT/ISA/237) mailed on Nov. 27, 2017, by the European Patent Office as the International Searching Authority for International Application No. PCT/FI2017/050541.
Yang, et al., "Electrogenerated chemiluminescence biosensing for the detection of prostate PC-3 cancer cells incorporating antibody as capture probe and ruthenium complex-labelled wheat germ agglutinin as signal probe", Analytica Chimica Acta, Sep. 2014, pp. 1-8, vol. 863.
Office Action issued on Mar. 3, 2023, by the Japanese Patent Office in corresponding Japanese Patent Application No. 2022-040090, and an English Translation of the Office Action. (4 pages).
The extended European Search Report issued on Mar. 30, 2023, by the European Patent Office in corresponding European Application No. 22214996.5. (11 pages).
Y. Kumada et al., "Improved Lectin ELISA for Glycosylation Analysis of Biomarkers Using PS-tag-fused Single-chain Fv", Journal of Immunological Methods, 2012, pp. 15-22, vol. 385, No. 1.

* cited by examiner

A

B

C

A

B

C

A

B

C

| 1st sample of BrCa, n=45 and HC=31 | |
|---|---|
| | AUC |
| CA15-3 IA | 0,805 |
| CA15-3MGL assay1 | 0,897 |
| CA153MGL assay2 | 0,848 |

| 1st sample of BrCa, n=41 HC=18 | |
|---|---|
| | AUC |
| CA15-3 IA | 0,833 |
| CA15-3WGA Assay | 0,880 |

LECTIN-BASED DIAGNOSTICS OF CANCERS

FIELD OF THE INVENTION

The present disclosure relates to non-invasive diagnostics of cancers, such as breast cancer, colorectal cancer, pancreatic cancer, prostate cancer on the basis of altered glycosylation patterns of cancer-associated biomarkers, especially CA15-3, CEA, CA19-9 and PSA.

BACKGROUND OF THE INVENTION

Some specific embodiments of the present disclosure relate to breast cancer (BrCa), which is the second leading cause of cancer death in women worldwide. The incidence is very low among women under 30 years of age but increases after 45 years of age. Mucin1 (MUC1 also known as CA15-3), located on the apical surface of human epithelial cells, is a large transmembrane glycoprotein with molecular weight ranging from 500 to 1000 kDa with extracellular portion consisting of highly conserved 20 amino acid repeat units (tandem repeats) within which there are five potential glycosylation sites. The CA15-3 antigen is secreted from tumor cells and is a well-established serological marker for monitoring the clinical course of breast cancer patients while it has poor sensitivity, being positive only in 17% of all breast cancer patients (Fleisher M. et al. 2002). The CA15-3 assay is not suitable as a diagnostic test because of its low sensitivity in stage I and II disease, but in advanced mammary carcinomas, changes in the antigen levels provide a useful non-invasive indicator of early recurrence, presence of residual disease, and continued remission of poor prognosis. Therefore, there is an urgent need of an improved BrCa biomarker especially for early detection of primary lesions abut also for earlier and more precise monitoring of malignancy, the degree of progress, and therapeutic effects on the cancer.

There is also a need for improved biomarkers for cancers such as gastrointestinal cancers including colorectal cancer and pancreatic cancer, and prostate cancer.

BRIEF DESCRIPTION OF THE INVENTION

In one aspect, the present invention provides a method of determining prostate cancer disease state in a subject. The method comprises the steps of: i) assaying a sample obtained from said subject for the level of a PSA glycoform which binds to macrophage galactose-type lectin (MGL) by determining binding of PSA to MGL; ii) comparing the detected level of said lectin-binding PSA glycoforms in said sample with that of a control sample or a predetermined threshold value; and iii) determining the prostate cancer disease state in said subject on the basis of said comparison. In some embodiments, the method may further comprise assaying said sample also for the conventional PSA protein antigen.

In another aspect, the invention provides a method of determining colorectal cancer disease state in a subject. The method comprises the steps of: i) assaying a sample obtained from said subject for the level of a CEA glycoform which binds to one or more lectins selected from the group consisting of mannose binding lectin (MBL), Dendritic Cell-Specific Intercellular adhesion molecule-3-Grabbing Nonintegrin (DC-SIGN) and MGL by determining binding of CEA to said lectin; ii) comparing the detected level of said lectin-binding CEA glycoforms in said sample with that of a control sample or a predetermined threshold value; and iii) determining the colorectal cancer disease state in said subject on the basis of said comparison. In some embodiments, the method may further comprise assaying said sample for the binding of CEA to MBL and DC-SIGN; MBL and MGL; DC-SIGN and MGL; or MBL, DC-SIGN and MGL. In some further embodiments, the method may also comprise assaying said sample also for the conventional CEA protein antigen.

In a further aspect, the invention provides a method of determining pancreatic cancer disease state in a subject. The method comprises the steps of: i) assaying a sample obtained from said subject for the level of a CA19-9 glycoform which binds to DC-SIGN by determining binding of CA19-9 to DC-SIGN; ii) comparing the detected level of said lectin-binding CA19-9 glycoform in said sample with that of a control sample or a predetermined threshold value; and iii) determining the prostate cancer disease state in said subject on the basis of said comparison. In some embodiments, the method may further comprise assaying said sample also for the conventional CA19-9 protein antigen.

In one aspect, the present disclosure provides a method of determining breast cancer disease state in a subject. The method comprises the steps of: i) assaying a sample obtained from said subject for the level of CA15-3 glycoform which binds to one or more lectins selected form the group consisting of MGL and WGA; ii) comparing the detected level of said lectin-binding glycoform of CA15-3 in said sample with that of a control sample or a predetermined threshold value; and iii) determining the breast cancer disease state in said subject on the basis of said comparison.

In some embodiments, the method of determining breast cancer disease state may further comprise assaying a sample obtained from said sample for one or more further lectin-binding glycoforms of a biomarker, wherein said biomarker is CA15-3 and said lectin is selected from the group consisting of DSL and Gal4, and/or for one or more conventional biomarkers selected from the group consisting of CA15-3, CA125, and CEA and/or for one or more further lectin-binding glycoforms of a biomarker, wherein said biomarker is selected from CA125 and CEA, and wherein said lectin selected from the group consisting of SBA, SNA, PNA, MAA II, AAL, UEA, PHA-E, RCA, WGA, WFA, PSA, VVL, TJA-II, DSL, HPA, MGL, DC-SIGN, MMR, MBL, Siglec-2, Siglec-3, Siglec-5, Siglec-9, Siglec-10, Siglec-11, Galectin-3, Galectin-4, and E-selectin.

Increased level of any one of the glycoforms or biomarkers set forth above in an assayed sample as compared with that of a control sample or a predetermined threshold value may be indicative that said subject has or is at risk of having cancer.

In some embodiments, the above methods of determining cancer disease state in a subject may be carried out for screening, diagnosing, prognosing, or monitoring said cancer. In some embodiments, said monitoring is for monitoring onset of said cancer, for monitoring any change in risk of having or developing said cancer, for monitoring response to treatment, for monitoring relapse of said cancer, or for monitoring recurrence of said cancer.

In further aspects, the present disclosure provides kits for use in the methods set forth above or in any one of their embodiments. In some embodiments, the kit comprises a PSA-binding agent and MGL, wherein either said CA15-3-binding agent or said MGL comprises a detectable label. In some other embodiments, the kit comprises a CEA-binding agent and one or more lectins selected from the group consisting of MBL, DC-SIGN and MGL, wherein either said CA15-3-binding agent or said lectin comprises a detectable label. In some still further embodiments, the kit comprises a CA19-9-binding agent and DC-SIGN, wherein either said CA15-3-binding agent or said DC-SIGN comprises a detectable label. In some even further embodiments, the kit comprises a CA15-3-binding agent, and one or more lectins selected from the group consisting of MGL and WGA, wherein either said CA15-3-binding agent or said one or more lectins comprise a detectable label. In some embodiments, the lectin in question may be immobilized on a detectable nanoparticle or it may be labelled with a detectable label.

In some embodiments, the kit may further comprise one or more lectins selected from the group consisting of SBA, SNA, PNA, MAA II, AAL, UEA, PHA-E, RCA, WGA, WFA, PSA, VVL, TJA-II, DSL, HPA, MGL, DC-SIGN, MMR, MBL, Siglec2, Siglec-3, Siglec-5, Siglec-9, Siglec-10, Siglec-11, Galectin-3, Galectin-4, E-selectin, DSL and Gal4, optionally provided as immobilized on a nanoparticle, and/or at least one reagent which binds to a biomarker selected from the group consisting of CA15-3, CA125, and CEA.

In some further aspects, the invention provides uses of different lectins for determining a cancer disease state in a subject. More specifically, provided herein is use of MGL for determining prostate cancer disease state in a subject by assaying a sample obtained from said subject for the level of PSA glycoform which binds to MGL; use of MBL, DC-SIGN and/or MGL for determining colorectal cancer disease state in a subject by assaying a sample obtained from said subject for the level of CEA glycoform which binds MBL, DC-SIGN and/or MGL; use of DC-SIGN for determining pancreatic cancer disease state in a subject by assaying a sample obtained from said subject for the level of CA19-9 glycoform which binds to DC-SIGN; and use of MGL or WGA, either alone or in combination, and optionally in combination with DSL and/or Gal4, for determining a breast cancer disease state in a subject by assaying a sample obtained from said subject for the level of CA15-3 glycoform which binds to MGL, WGA, DSL, and/or Gal4. In any of these embodiments, lectin in question may be immobilized on a nanoparticle or labelled with a detectable label.

Other objectives, aspects, embodiments, details and advantages of the present invention will become apparent from the following figures, detailed description, examples, and dependent claims.

BRIEF DESCRIPTION OF THE DRAWINGS

In the following the invention will be described in greater detail by means of preferred embodiments with reference to the attached drawings, in which FIG. 1A illustrates a conventional CA15-3 immunoassay, in which the capture and tracer Mab's detect the protein core and sialylated carbohydrate epitopes of CA15-3, respectively. FIG. 1B illustrates a combined immuno-lectin-assay, in which CA15-3 is captured with a specific Mab and traced with lectins, coated on $Eu^{+3}$-nanoparticles, which bind to glycan moieties of CA15-3.

In FIG. 17B the CRC patients are grouped into two categories: the patients who were alive at the end of follow-up and the patients who died during follow-up. Mann-Whitney's U-test $p<0.01$: **, $p<0.05$: *, and $p>0.05$: •. The short horizontal bars present the medians. The long horizontal line presents the cutoff of 5 ng/ml for commercial CEA immunoassay, and the dotted lines the prospective cutoff levels for different glycovariant CEA assays.

DETAILED DESCRIPTION OF THE INVENTION

Figure 1:
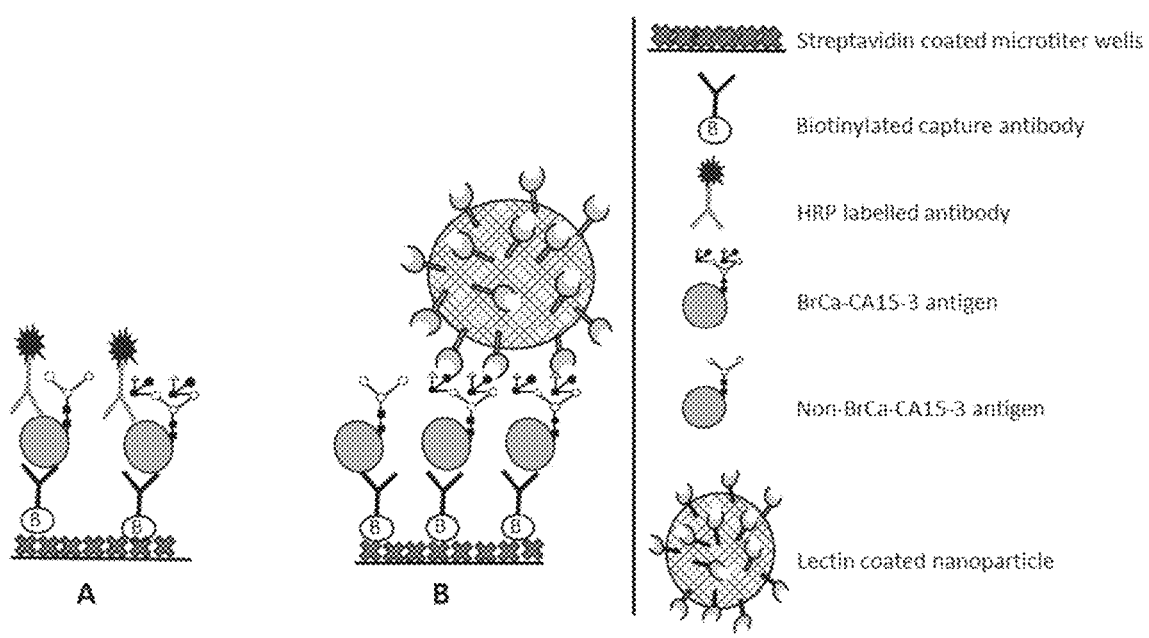
FIG. 1 is a schematic representation of different assay formats.

The present disclosure is, at least partly, based on studies aiming to identify glycoforms of known cancer biomarkers with improved sensitivity over other species of the same biomarkers. In accordance with this aim, the present disclosure provides means and methods of determining cancer state in a subject who is suspected to suffer from or be at risk of suffering from cancer, especially for screening, diagnosing, prognosing, or monitoring said cancer. According to specific embodiments, said cancer is breast cancer, gastrointestinal cancer such as colorectal cancer or pancreatic cancer, or prostate cancer.

As used herein, the term "or" has the meaning of both "and"" and "or" (i.e. "and/or"). Furthermore, the meaning of a singular noun includes that of a plural noun and thus a singular term, unless otherwise specified, may also carry the meaning of its plural form. In other words, the term "a" or "an" may mean one or more.

As used herein, the term "subject" refers to an animal, preferably to a mammal, more preferably to a human, and in some embodiments most preferably to a female like in embodiments relating to breast cancer, while in some other embodiments most preferably to a male like in embodiments relating to prostate cancer. Depending on an embodiment in question, said subject may suffer from cancer with or without diagnosis, be suspected to suffer from cancer, be at risk of cancer, or may have already been treated for cancer. Herein, the terms "human subject", "patient" and "individual" are interchangeable.

As used herein, the term "sample" refers to a tissue sample, such as a biopsy sample taken from breast tissue, and to a sample of a bodily fluid, such as ascites fluid, urine, blood, plasma, serum, and peritoneal cavity fluid, obtained from a subject. In some embodiments, said tissue sample may be a formalin-fixed or paraffin-embedded tissue sample.

Generally, obtaining the sample to be analysed from a subject is not part of the present method of determining a subject's cancer disease state. A blood, serum or plasma sample is the most preferred sample type to be used in the present method and its all embodiments.

The term "sample" also includes samples that have been manipulated or treated in any appropriate way after their procurement, including but not limited to centrifugation, filtration, precipitation, dialysis, chromatography, treatment with reagents, washing, or enriching for a certain component of the sample such as a cell population.

As used herein, the terms "biomarker" and "marker" are interchangeable, and refer to a molecule which is differentially present in a sample taken from a subject suffering from cancer as compared with a comparable sample taken from a subject who is apparently heathy. Accordingly, the biomarker may be referred to as a cancer biomarker. Preferred cancer biomarkers include CA15-3, CA125, CEA, CA19-9 and PSA, and especially certain lectin-binding glycoforms thereof. As used herein, the terms "CA15-3", "CA125", "CEA", "CA19-9", and "PSA" refer to the conventional CA15-3, CA125, CEA, CA19-9, and PSA protein antigens, respectively, which are detectable by conventional immunoassays. As used herein, the terms $CA15-3^{LECTIN}$, $CA125^{LECTIN}$, $CEA^{LECTIN}$, $CA19-9^{LECTIN}$, and $PSA^{LECTIN}$ refer to lectin-binding glycoforms of these biomarkers. By way of example, the term "$CA15-3^{WGA}$" refers to glycoforms of CA15-3 which bind to WGA.

In embodiments which concern assessment of the level of more than one biomarker, same or different samples obtained from a subject whose cancer disease state is to be determined may be used for each assessment. Said different samples may be of the same or different type.

As used herein, the term "level" is interchangeable with the terms "amount" and "concentration", unless otherwise indicated.

To determine whether a detected level of a biomarker is indicative of the presence or risk of the presence of a disease associated with said biomarker, its level in a relevant control has to be determined. Once the control levels are known, the determined marker levels can be compared therewith and the significance of the difference can be assessed using standard statistical methods. In some embodiments, a statistically significant difference between the determined biomarker level and the control level is indicative of the disease in question. In some further embodiments, before to be compared with the control, the biomarker levels are normalized using standard methods.

Comparison of the assayed level of a biomarker in a sample to be analysed with that of a relevant control or a predetermined threshold value may in some embodiments be performed by a processor of a computing device.

Regardless of whether or not the processor of the computing device is used for said comparison, the level of the assayed level of a biomarker is, at least in some embodiments, determined as "increased" or "higher" if the level of the biomarker in the sample is, for instance, at least about 1.5 times, 1.75 times, 2 times, 3 times, 4 times, 5 times, 6 times, 8 times, 9 times, 10 times, 20 times or 30 times the predetermined threshold level or the level of the biomarker in a control sample. In some embodiments, the difference between the level of the biomarker in the sample to be analyzed and the predetermined threshold level or the level of the biomarker in a control sample has to be statistically significant in order to provide a proper diagnostic, prognostic or predictive result.

Concentration of a biomarker in a sample obtained from a subject whose cancer disease state is to be determined or who is to be screened, diagnosed, prognosed, or monitored for cancer is considered "non-increased" or "normal" if the detected concentration thereof is lower, essentially the same or essentially non-altered as compared with that of a relevant control sample or a predetermined threshold value.

As used herein, the term "control" may refer to a control sample obtained from an apparently healthy individual or pool of apparently healthy individuals, or it may refer to a predetermined threshold value, i.e. a cut-off value, which is indicative of the presence or absence of the disease in question. Statistical methods for determining appropriate threshold values will be readily apparent to those of ordinary skill in the art. The threshold values may have been determined, if necessary, from samples of subjects of the same age, demographic features, and/or disease status, etc. The threshold value may originate from a single individual not affected by the disease in question or be a value pooled from more than one such individual.

In some embodiments, the term "control sample" refers to a sample obtained from the same subject whose cancer disease state is to be determined but obtained at a time point different from the time point of the disease state determination. Non-limiting examples of such different time points include one or more time points before diagnosis of the disease, one or more time points after diagnosis of the disease, one or more time points before treatment of the disease, one or more time points during treatment of the disease, and one or more time points after treatment of the disease. Typically, such control samples obtained from the same subject are used when the purpose of breast cancer disease state determination is to monitor said disease, especially to monitor the onset of the disease, or risk development of the disease, response to treatment, relapse of the disease, or recurrence of the disease.

As used herein, the term "apparently healthy" refers to an individual or a pool of individuals who show no signs of cancer and thus are believed not to be affected by cancer or who are predicted not to develop cancer.

As used herein, the term "indicative of a disease", when applied to a biomarker, refers to a level which, using routine statistical methods setting confidence levels at a minimum of 95%, is diagnostic of said disease or a stage of said disease such that the detected level is found significantly more often in subjects with said disease or a stage of said disease than in subjects without said disease or another stage of said disease. Preferably, the level which is indicative of a disease is found in at least 80% of subjects who have the disease and is found in less than 10% of subjects who do not have the disease. More preferably, the level which is indicative of said disease is found in at least 90%, at least 95%, at least 98%, or more in subjects who have the disease and is found in less than 10%, less than 8%, less than 5%, less than 2.5%, or less than 1% of subjects who do not have the disease.

Existing CA15-3 immunoassays routinely used diagnostically are based on the determination of CA15-3 antigen levels in serum or plasma by two different monoclonal antibodies which recognize different epitopes of CA15-3. In some non-limiting embodiments, one of the antibodies may be specific for a protein epitope while the other may be specific for a carbohydrate epitope, such as a sialylated carbohydrate epitope. Such conventional immunoassays, herein referred to as "assaying a sample for CA15-3 antigen concentration", are commercially available from several different providers. Accordingly, the term "CA15-3" refers to the CA15-3 species recognizable by the conventional immunoassays. In some embodiments, cut-off levels such as 20 U/ml, 22 U/ml, 25 U/ml, 30 U/ml or 35 U/ml may be employed.

In the experiments leading to some embodiments of the present invention, two lectins, namely macrophage galactose-type lectin (MGL) and wheat germ agglutinin (WGA), among a panel of 28 different plant or human lectins tested showed remarkably high reactivity towards CA15-3 derived from a breast cancer cell line. Also Datura stramonium Lectin (DSL) and Galectin-4 (Gal4) showed some reactivity towards cancerous CA15-3.

For the sake of simplicity, "CA15-3$^{LECTIN}$" is used as a general term to refer to any one or more lectin-binding glycoforms of CA15-3, including for example CA15-3$^{MGL}$, CA15-3$^{WGA}$, CA15-3$^{DSL}$, or CA15-3$^{GAL4}$, which refer to MGL-, WGA-, DSL- and Gal4-binding species of CA15-3, respectively.

Clinical applicability of the results obtained with breast cancer-derived isolated CA15-3 was verified in a small cohort of samples obtained from patients with metastatic breast cancer. By assaying the samples for CA15-3$^{MGL}$ or CA15-3$^{WGA}$, subjects with breast cancer could be distinguished from healthy controls with higher sensitivity than by using a conventional CA15-3 immunoassay. Moreover, median fold-difference between healthy controls and breast cancer patients was only 2-fold with the existing CA15-3 immunoassay, while it was >200-fold with the CA15-3$^{MGL}$ assay. In a different cohort, median fold-difference between healthy controls and breast cancer patients was only 2.8-fold with the existing CA15-3 immunoassay, while it was >400-fold with the CA15-3$^{MGL}$ assay. In some embodiments, CA15-3$^{WGA}$ is the preferred lectin to be used.

One way to compare the performance of different biomarkers is to draw ROC curves and compare their AUC values, false positive rates, false negative rates, and success rates. As demonstrated in the experimental part, the false negative rate of the CA15-3$^{MGL}$ assay was lower than that of the conventional assay. Moreover, higher AUC values were obtained both in CA15-3$^{MGL}$ and CA15-3$^{WGA}$ assays than in the conventional CA15-3 assays.

Receiver Operating Characteristic (ROC) curves may be utilized to demonstrate the trade-off between the sensitivity and specificity of a marker, as is well known to skilled persons. The sensitivity is a measure of the ability of the marker to detect the disease, and the specificity is a measure of the ability of the marker to detect the absence of the disease. The horizontal X-axis of the ROC curve represents 1-specificity, which increases with the rate of false positives. The vertical Y-axis of the curve represents sensitivity, which increases with the rate of true positives. Thus, for a particular cut-off selected, the values of specificity and sensitivity may be determined. In other words, data points on the ROC curves represent the proportion of true-positive and false-positive classifications at various decision boundaries. Optimum results are obtained as the true-positive proportion approaches 1.0 and the false-positive proportion approaches 0.0. However, as the cut-off is changed to increase specificity, sensitivity usually is reduced and vice versa.

As used herein, the term "false positive" refers to a test result, which classifies an unaffected subject incorrectly as an affected subject. Likewise, "false negative" refers to a test result, which classifies an affected subject incorrectly as an unaffected subject.

As used herein, the term "true positive" refers to a test result, which classifies a subject who has a disease correctly as an affected subject. Likewise, "true negative" refers to a test result, which classifies an unaffected subject correctly as an unaffected.

In accordance with the above, the term "success rate" refers to the percentage-expressed proportion of affected individuals with a positive result, while the term "false positive rate" refers to the percentage-expressed proportion of unaffected individuals with a positive result.

The area under the ROC curve, often referred to as the AUC, is a measure of the utility of a marker in the correct identification of disease subjects. Thus, the AUC can be used to determine the effectiveness of the test. An area of 1 represents a perfect test; an area of 0.5 represents a worthless test. A traditional rough guide for classifying the accuracy of a diagnostic or predictive test is the following: AUC values 0.9 to 1 represent test with excellent diagnostic or prognostic power, AUC values 0.80 to 0.90 represent a test with good diagnostic or prognostic power, AUC values 0.70 to 0.80 represent a test with fair diagnostic or prognostic power, AUC values 0.60 to 0.70 represent a test with poor diagnostic or prognostic power, and AUC values 0.50 to 0.60 represent a test with failed diagnostic or prognostic power.

CA15-3$^{MGL}$ and CA15-3$^{WGA}$ assays did not correlate well with each other, or with the conventional immunoassay. It is thus envisaged that, in some embodiments, it would be advantageous to use these assays in combination to complement their performance.

In accordance with the above, the present invention provides a method of determining breast cancer state in a subject by assaying a sample obtained from said subject for CA15-3$^{MGL}$ and/or CA15-3$^{WGA}$. Increased level of said CA15-3$^{MGL}$ and/or CA15-3$^{WGA}$ in said sample as compared with that of a control sample or a predetermined threshold value is indicative that said subject has or is at risk of having breast cancer. On the other hand, non-increased or normal level of both CA15-3$^{MGL}$ and CA15-3$^{WGA}$ in said sample as compared with that of a control sample or a predetermined threshold value is indicative that said subject is apparently healthy with respect to breast cancer or is not at risk of having or developing breast cancer. It is envisaged that since the results of CA15-3$^{MGL}$ and CA15-3$^{WGA}$ assays did not correlate well in the clinical analyses made, sensitivity of the method may be improved by carrying out assays for both CA15-3$^{MGL}$ and CA15-3$^{WGA}$.

In some embodiments of the above method, a sample obtained from a subject whose breast cancer disease state is to be determined, may be further assayed for one or both of CA15-3$^{DSL}$ and CA15-3$^{GAL4}$ in order to improve the performance of the disease state determination. Accordingly, said sample may be assayed either for CA15-3$^{MGL}$ and CA15-3$^{DSL}$; CA15-3$^{MGL}$ and CA15-3$^{GAL4}$; CA15-3$^{WGA}$ and CA15-3$^{DSL}$; CA15-3$^{WGA}$ and CA15-3$^{GAL4}$; CA15-3$^{MGL}$, CA15-3$^{DSL}$ and CA15-3$^{GAL4}$; CA15-3$^{WGA}$, CA15-3$^{DSL}$, and CA15-3$^{GAL4}$; or CA15-3$^{MGL}$, CA15-3$^{WGA}$, CA15-3$^{DSL}$, and CA15-3$^{GAL4}$.

In any aspects and embodiments disclosed herein, the predetermined threshold value for CA15-3$^{LECTIN}$ may be from about 2 U/ml to about 3 U/ml, e.g. about 2.5 U/ml. However, depending on the desired sensitivity and specificity, other predetermined threshold values for CA15-3$^{LECTIN}$ may be used. Non-limiting examples of such other threshold values include any values falling within ranges from about 2 U/ml to about 7 U/ml, from about 2 U/ml to about 6 U/ml, from about 2 U/ml to about 5 U/ml, and from about 2 U/ml to about 4 U/ml. For screening purposes and other uses where the clinical sensitivity of the assay needs be maximized, threshold values as low as about 0.5 to 2 U/ml, e.g.

about 1 U/ml or 1.5 U/ml, may also be used. On the other hand, in diagnostic or other embodiments where the clinical specificity of the assay needs be maximized, threshold values as high as about 5 to 20 U/ml, e.g. about 10 U/ml or 15 U/ml, may also be used. However, these ranges may also vary depending on the specifics of the detection technique.

Because of poor correlation between CA15-3$^{MGL}$ or CA15-3$^{WGA}$ assays and the conventional CA15-3 immunoassay, it is envisaged that the sensitivity of the method may be improved also by including CA15-3 as a further biomarker in the method. Accordingly, in some embodiments, the method of determining a subject's breast cancer disease state may comprise assaying a sample obtained from said sample for one or more CA15-3$^{LECTIN}$ species set forth above, and assaying the same or a different sample obtained from said subject for CA15-3 concentration conventionally. In such a method, increased level of at least one of the CA15-3$^{LECTIN}$ species or increased level of CA15-3 would be indicative that said subject has or is at risk of having breast cancer. On the other hand, non-increased or normal level of all the assayed CA15-3$^{LECTIN}$ species in combination with non-increased or normal level of CA15-3 would be indicative that said subject does not have or is not at risk of having breast cancer, i.e. is apparently healthy. Depending on the desired performance, for instance regarding sensitivity and specificity, the method may comprise assaying same or different samples for either CA15-3$^{MGL}$ and CA15-3;
CA15-3$^{WGA}$ and CA15-3;
CA15-3$^{MGL}$, CA15-3$^{WGA}$, and CA15-3;
CA15-3$^{MGL}$, CA15-3$^{DSL}$ and CA15-3;
CA15-3$^{MGL}$, CA15-3$^{GAL4}$, and CA15-3;
CA15-3$^{WGA}$, CA15-3$^{DSL}$, and CA15-3;
CA15-3$^{WGA}$, CA15-3$^{GAL4}$, and CA15-3;
CA15-3$^{MGL}$, CA15-3$^{DSL}$, CA15-3$^{GAL4}$, and CA15-3;
CA15-3$^{WGA}$, CA15-3$^{DSL}$, CA15-3$^{GAL4}$, and CA15-3; or
CA15-3$^{MGL}$, CA15-3$^{WGA}$, CA15-3$^{DSL}$, CA15-3$^{GAL4}$, and CA15-3.

Human cancer antigen 125 (CA125), also known as mucin 16 or MUC16, is a complex transmembrane glycoprotein and the most widely used biomarker for epithelial ovarian cancer. However, its expression may be elevated also in other cancers, including breast cancer, colorectal cancer, pancreatic cancer, and liver cancer. Accordingly, one or more lectin-binding glycoforms of CA125, collectively referred to herein as CA125$^{LECTIN}$, may in some embodiments of the present methods be used as further markers for determining a subject's breast cancer disease state. Depending on the desired performance of the method in determining a subject's breast cancer disease state, such as sensitivity or specificity, a sample obtained from said subject may be assayed for either CA15-3$^{MGL}$ and CA125$^{LECTIN}$;
CA15-3$^{WGA}$ and CA125$^{LECTIN}$;
CA15-3$^{MGL}$, CA15-3$^{WGA}$, and CA125$^{LECTIN}$;
CA15-3$^{MGL}$, CA15-3$^{DSL}$ and CA125$^{LECTIN}$;
CA15-3$^{MGL}$, CA15-3$^{GAL4}$, and CA125$^{LECTIN}$;
CA15-3$^{WGA}$, CA15-3$^{DSL}$, and CA125$^{LECTIN}$;
CA15-3$^{WGA}$, CA15-3$^{GAL4}$, and CA125$^{LECTIN}$;
CA15-3$^{MGL}$, CA15-3$^{DSL}$, CA15-3$^{GAL4}$, and CA125$^{LECTIN}$;
CA15-3$^{WGA}$, CA15-3$^{DSL}$, CA15-3$^{GAL4}$, and CA125$^{LECTIN}$; or
CA15-3$^{MGL}$, CA15-3$^{WGA}$, CA15-3$^{DSL}$, CA15-3$^{GAL4}$, and CA125$^{LECTIN}$.

Preferably, CA125$^{LECTIN}$ is CA125$^{MGL}$ but it may also be any one or more of lectin-binding species of CA125. In other words, said "LECTIN" in the general term CA125$^{LECTIN}$ may refer to any one or more CA125-binding lectins, wherein said lectin is selected from the group consisting of SBA, SNA, PNA, MAA II, AAL, UEA, PHA-E, RCA, WGA, WFA, PSA, VVL, TJA-II, DSL, HPA, MGL, DC-SIGN, MMR, MBL, Siglec-2, Siglec-3, Siglec-5, Siglec-9, Siglec-10, Siglec-11, Galectin-3, Galectin-4, and E-selectin. Assaying for any one of the CA15-3$^{LECTIN}$ and CA125$^{LECTIN}$ combinations disclosed above may further comprise assaying for conventional CA15-3 and/or CA125. In some non-limiting embodiments, a cut-off value of 35 U/ml may be employed for CA125.

Carcinoembryonic antigen (CEA) is a widely used glycoprotein biomarker especially for cancers of the large intestine (colon and rectal cancer). However, its expression is elevated also in many other cancers, including breast, gastrointestinal tract, liver, lung, ovarian, pancreatic, and prostatic cancers. Accordingly, one or more lectin-binding glycoforms of CEA, collectively referred to herein as CEA$^{LECTIN}$, may in some embodiments of the present methods be used as further markers for determining a subject's breast cancer disease state. Depending on the desired performance of the method in determining a subject's breast cancer disease state, such as sensitivity or specificity, a sample obtained from said subject may be assayed for either CA15-3$^{MGL}$ and CEA$^{LECTIN}$;
CA15-3$^{WGA}$ and CEA$^{LECTIN}$;
CA15-3$^{MGL}$, CA15-3$^{WGA}$, and CEA$^{LECTIN}$;
CA15-3$^{MGL}$, CA15-3$^{DSL}$ and CEA$^{LECTIN}$;
CA15-3$^{MGL}$, CA15-3$^{GAL4}$, and CEA$^{LECTIN}$;
CA15-3$^{WGA}$, CA15-3$^{DSL}$, and CEA$^{LECTIN}$;
CA15-3$^{WGA}$, CA15-3$^{GAL4}$, and CEA$^{LECTIN}$;
CA15-3$^{MGL}$, CA15-3$^{DSL}$, CA15-3$^{GAL4}$, and CEA$^{LECTIN}$;
CA15-3$^{WGA}$, CA15-3$^{DSL}$, CA15-3$^{GAL4}$, and CEA$^{LECTIN}$; or
CA15-3$^{MGL}$, CA15-3$^{WGA}$, CA15-3$^{DSL}$, CA15-3$^{GAL4}$, and CEA$^{LECTIN}$.

Preferably, CEA$^{LECTIN}$ is CEA$^{MBL}$ CEA$^{DC-SIGN}$ and/or CEA$^{MGL}$, but it may also be any other one or more of lectin-binding species of CEA. In other words, said "LECTIN" in the general term CEA$^{LECTIN}$ may refer to any one or more CEA-binding lectins, wherein said lectin is selected from the group consisting of SBA, SNA, PNA, MAA II, AAL, UEA, PHA-E, RCA, WGA, WFA, PSA, VVL, TJA-II, DSL, HPA, MGL, DC-SIGN, MMR, MBL, Siglec-2, Siglec-3, Siglec-5, Siglec-9, Siglec-10, Siglec-11, Galectin-3, Galectin-4, and E-selectin. Assaying for any one of the CA15-3$^{LECTIN}$ and CEA$^{LECTIN}$ combinations disclosed above may further comprise assaying for conventional CA15-3 and/or CEA. In some non-limiting embodiments, any cut-off values ranging from about 2.5 µg/l to about 10 µg/l, such as 2.7 µg/l or 5 µg/l, may be employed for CEA.

Furthermore, in some embodiments, the present method of determining a subject's breast cancer disease state may comprise assaying a sample obtained from said subject for either CA15-3$^{MGL}$, CA125$^{LECTIN}$, and CEA$^{LECTIN}$;
CA15-3$^{WGA}$, CA125$^{LECTIN}$, and CEA$^{LECTIN}$;
CA15-3$^{MGL}$, CA15-3$^{WGA}$, CA125$^{LECTIN}$, and CEA$^{LECTIN}$;
CA15-3$^{MGL}$, CA15-3$^{DSL}$, CA125$^{LECTIN}$, and CEA$^{LECTIN}$;
CA15-3$^{MGL}$, CA15-3$^{GAL4}$, CA125$^{LECTIN}$, and CEA$^{LECTIN}$;
CA15-3$^{WGA}$, CA15-3$^{DSL}$, CA125$^{LECTIN}$, and CEA$^{LECTIN}$;
CA15-3$^{WGA}$, CA15-3$^{GAL4}$, CA125$^{LECTIN}$, and CEA$^{LECTIN}$;

CA15-3$^{MGL}$, CA15-3$^{DSL}$, CA15-3$^{GAL4}$, CA125$^{LECTIN}$, and CEA$^{LECTIN}$;
CA15-3$^{WGA}$, CA15-3$^{DSL}$, CA15-3$^{GAL4}$, CA125$^{LECTIN}$, and CEA$^{LECTIN}$; or
CA15-3$^{MGL}$, CA15-3$^{WGA}$, CA15-3$^{DSL}$, CA15-3$^{GAL4}$, CA125$^{LECTIN}$, and CEA$^{LECTIN}$.

Preferably, CA125$^{LECTIN}$ is CA125$^{MGL}$, and CEA$^{LECTIN}$ is CEA$^{MBL}$, CEA$^{DC\text{-}SIGN}$ and/or CEA$^{MGL}$, but said "LECTIN" in the general terms CA125$^{LECTIN}$ and CEA$^{LECTIN}$ may refer, independently from each other, to any one or more CA125- or CEA-binding lectins, wherein said lectin is selected from the group consisting of SBA, SNA, PNA, MAA II, AAL, UEA, PHA-E, RCA, WGA, WFA, PSA, VVL, TJA-II, DSL, HPA, MGL, DC-SIGN, MMR, MBL, Siglec-2, Siglec-3, Siglec-5, Siglec-9, Siglec-10, Siglec-11, Galectin-3, Galectin-4, and E-selectin, respectively. Assaying for any one of the CA15-3$^{LECTIN}$, CA125$^{LECTIN}$, and CEA$^{LECTIN}$ combinations disclosed above may further comprise assaying for conventional CA15-3, CA125, and/or CEA.

In some embodiments, the present method of determining a subject's breast cancer disease state may comprise assaying a sample obtained from said subject for
CEA$^{MBL}$
CEA$^{DC\text{-}SIGN}$,
CEA$^{MGL}$,
CEA$^{MBL}$ and CEA$^{DC\text{-}SIGN}$,
CEA$^{MBL}$ and CEA$^{MGL}$,
CEA$^{DC\text{-}SIGN}$ and CEA$^{MGL}$,
CEA$^{MBL}$, CEA$^{DC\text{-}SIGN}$ and CEA$^{MGL}$,
CEA$^{MBL}$ and CA15-3$^{MGL}$,
CEA$^{DC\text{-}SIGN}$ and CA15-3$^{MGL}$,
CEA$^{MGL}$ and CA15-3$^{MGL}$,
CEA$^{MBL}$ and CA15-3$^{WGA}$,
CEA$^{DC\text{-}SIGN}$ and CA15-3$^{WGA}$,
CEA$^{MGL}$ and CA15-3$^{WGA}$,
CEA$^{MBL}$, CA15-3$^{MGL}$, and CA15-3$^{WGA}$,
CEA$^{MBL}$, CA15-3$^{MGL}$, and CA15-3$^{DSL}$,
CEA$^{MBL}$, CA15-3$^{MGL}$, and CA15-3$^{GAL4}$,
CEA$^{MBL}$, CA15-3$^{WGA}$, and CA15-3$^{DSL}$,
CEA$^{MBL}$, CA15-3$^{WGA}$, and CA15-3$^{GAL4}$,
CEA$^{MBL}$, CA15-3$^{MGL}$, CA15-3$^{DSL}$, and CA15-3$^{GAL4}$,
CEA$^{MBL}$, CA15-3$^{WGA}$, CA15-3$^{DSL}$, and CA15-3$^{GAL4}$,
CEA$^{MBL}$, CA15-3$^{MGL}$, CA15-3$^{WGA}$, CA15-3$^{DSL}$, and CA15-3$^{GAL4}$, CEA$^{DC\text{-}SIGN}$ CA15-3$^{MGL}$, and CA15-3$^{WGA}$,
CEA$^{DC\text{-}SIGN}$, CA15-3$^{MGL}$, and CA15-3$^{DSL}$,
CEA$^{DC\text{-}SIGN}$, CA15-3$^{MGL}$, and CA15-3$^{GAL4}$,
CEA$^{DC\text{-}SIGN}$, CA15-3$^{WGA}$, and CA15-3$^{DSL}$,
CEA$^{DC\text{-}SIGN}$, CA15-3$^{WGA}$, and CA15-3$^{GAL4}$,
CEA$^{DC\text{-}SIGN}$, CA15-3$^{MGL}$, CA15-3$^{DSL}$, and CA15-3$^{GAL4}$,
CEA$^{DC\text{-}SIGN}$, CA15-3$^{WGA}$, CA15-3$^{DSL}$, and CA15-3$^{GAL4}$,
CEA$^{DC\text{-}SIGN}$, CA15-3$^{MGL}$, CA15-3$^{WGA}$, CA15-3$^{DSL}$, and CA15-3$^{GAL4}$,
CEA$^{MGL}$ and CA15-3$^{MGL}$,
CEA$^{MGL}$ and CA15-3$^{WGA}$
CEA$^{MGL}$, CA15_3$^{MGL}$, and CA15_3$^{WGA}$
CEA$^{MGL}$, CA15-3$^{MGL}$, and CA15-3$^{DSL}$;
CEA$^{MGL}$, CA15-3$^{MGL}$, and CA15-3$^{GAL4}$,
CEA$^{MGL}$, CA15-3$^{WGA}$, and CA15-3$^{DSL}$,
CEA$^{MGL}$, CA15-3$^{WGA}$, and CA15-3$^{GAL4}$,
CEA$^{MGL}$, CA15-3$^{MGL}$, CA15-3$^{DSL}$, and CA15-3$^{GAL4}$,
CEA$^{MGL}$, CA15-3$^{WGA}$, CA15-3$^{DSL}$, and CA15-3$^{GAL4}$,
CEA$^{MGL}$, CA15-3$^{MGL}$, CA15-3$^{WGA}$, CA15-3$^{DSL}$, and CA15-3$^{GAL4}$,
CEA$^{MBL}$, CEA$^{DC\text{-}SIGN}$, and CA15-3$^{MGL}$,
CEA$^{MBL}$, CEA$^{MGL}$, and CA15-3$^{MGL}$,
CEA$^{DC\text{-}SIGN}$, CEA$^{MGL}$, and CA15-3$^{MGL}$,
CEA$^{MBL}$, CEA$^{DC\text{-}SIGN}$, and CA15-3$^{WGA}$,
CEA$^{MBL}$, CEA$^{MGL}$, and CA15-3$^{WGA}$,
CEA$^{DC\text{-}SIGN}$, CEA$^{MGL}$, and CA15-3$^{WGA}$,
CEA$^{DC\text{-}SIGN}$, CEA$^{MBL}$, CA15-3$^{MGL}$, and CA15-3$^{WGA}$
CEA$^{DC\text{-}SIGN}$, CEA$^{MBL}$, CA15-3$^{MGL}$, and CA15-3$^{DSL}$
CEA$^{DC\text{-}SIGN}$, CEA$^{MBL}$, CA15-3$^{MGL}$, and CA15-3$^{GAL4}$;
CEA$^{DC\text{-}SIGN}$, CEA$^{MBL}$, CA15-3$^{WGA}$, and CA15-3$^{DSL}$
CEA$^{DC\text{-}SIGN}$, CEA$^{MBL}$, CA15-3$^{WGA}$, and CA15-3$^{GAL4}$,
CEA$^{MGL}$, CEA$^{MBL}$, CA15-3$^{MGL}$, and CA15-3$^{WGA}$,
CEA$^{MGL}$, CEA$^{MBL}$, CA15-3$^{MGL}$, and CA15-3$^{DSL}$,
CEA$^{MGL}$, CEA$^{MBL}$, CA15-3$^{MGL}$, and CA15-3$^{GAL4}$,
CEA$^{MGL}$, CEA$^{MBL}$, CA15-3$^{WGA}$, and CA15-3$^{DSL}$,
CEA$^{MGL}$, CEA$^{MBL}$, CA15-3$^{WGA}$, and CA15-3$^{GAL4}$,
CEA$^{DC\text{-}SIGN}$, CEA$^{MBL}$, CA15-3$^{MGL}$, and CA15-3$^{WGA}$
CEA$^{DC\text{-}SIGN}$, CEA$^{MGL}$, CA15-3$^{MGL}$, and CA15-3$^{DSL}$
CEA$^{DC\text{-}SIGN}$, CEA$^{MGL}$, CA15-3$^{MGL}$, and CA15-3$^{GAL4}$;
CEA$^{DC\text{-}SIGN}$, CEA$^{MGL}$, CA15-3$^{WGA}$, and CA15-3$^{DSL}$
CEA$^{DC\text{-}SIGN}$, CEA$^{MGL}$, CA15-3$^{WGA}$, and CA15-3$^{GAL4}$
CEA$^{MBL}$, CEA$^{DC\text{-}SIGN}$, CEA$^{MBL}$, CA15-3$^{MGL}$, CA15-3$^{DSL}$, and CA15-3$^{GAL4}$,
CEA$^{MBL}$, CEA$^{DC\text{-}SIGN}$, CEA$^{MBL}$, CA15-3$^{WGA}$, CA15-3$^{DSL}$, and CA15-3$^{GAL4}$, or
CEA$^{MBL}$, CEA$^{DC\text{-}SIGN}$, CEA$^{MBL}$, CA15-3$^{MGL}$, CA15-3$^{WGA}$, CA15-3$^{DSL}$, and CA15-3$^{GAL4}$.

Assaying a sample for any one of the biomarker combinations set forth above, may further comprise assaying also for one or more breast cancer-associated biomarkers selected from the group consisting of one or more CA125$^{LECTIN}$ species (e.g. CA125$^{MGL}$), one or more CA19-9$^{LECTIN}$ (e.g. CA19-9$^{DC\text{-}SIGN}$) species, conventional CEA, conventional CA15-3, conventional CA125, and conventional CA19-9.

More generally, the present method of determining a subject's breast cancer disease state may in some embodiments comprise assaying a sample obtained from said subject for any one or more lectin-binding species of a biomarker selected from the group consisting of CEA$^{LECTIN}$ (e.g. CEA$^{MBL}$ CEA$^{DC\text{-}SIGN}$ and/or CEA$^{MGL}$), CA19-9$^{LECTIN}$ (e.g. CA19-9$^{DC\text{-}SIGN}$), CA125$^{LECTIN}$ (e.g. CA125$^{MGL}$), and CA15-3$^{LECTIN}$ (e.g. CA15-3$^{MGL}$ and/or CA15-3$^{WGA}$, optionally in combination with CA15-3$^{DSL}$ and/or CA15-3$^{GAL4}$), and optionally, assaying a sample also for one or more conventional breast-cancer associated biomarker selected from the group consisting of CEA, CA19-9, CA125, and CA15-3.

In any of the embodiments set forth above, the method of determining a breast cancer disease state in a subject may be more specifically formulated as a method of screening, diagnosing, prognosing and/or monitoring breast cancer, be it de novo or recurrent appearance or suspicion of breast cancer.

In accordance with the above, the present method is in some embodiments directed to diagnosing of breast cancer, i.e. determining whether or not a subject has or is at risk of having or developing breast cancer. This is also meant to include instances where the presence or the risk of breast cancer is not finally determined but that further diagnostic testing is warranted. In such embodiments, the method is not by itself determinative of the presence or absence, or of the risk of breast cancer in the subject but can indicate that further diagnostic testing is needed or would be beneficial. Therefore, the present method may be combined with one or more other diagnostic methods for the final determination of the presence or absence, or of the risk of breast cancer in the subject. Such other diagnostic methods are well known to a person skilled in the art.

Being non-invasive and suitable for analysing urine and serum samples, the present method and its various embodiments may be easily incorporated into a population screening protocol to identify subjects having or being at risk of having or developing breast cancer. This would enable not only early diagnosis of breast cancer, but also active surveillance for the onset of breast cancer in subjects with identified increased risk of developing breast cancer later in life. Moreover, early detection of breast cancer would allow treating the disease early when chances of cure are at their highest.

The present method and its various embodiments may be used not only for diagnostic purposes but also for prognosis or predicting the outcome of breast cancer, or monitoring onset of breast cancer, any development in risk of breast cancer, the subject's recovery or survival from breast cancer, any possible relapse or recurrence of the disease, or response to treatment. In some embodiments, the method comprises monitoring breast cancer in said subject by comparing the level of one or more $CA15-3^{LECTIN}$ species set forth above, with or without concomitantly comparing the level of one or more further biomarkers selected from the group consisting of CA15-3, $CA125^{LECTIN}$, CA125, $CEA^{LECTIN}$, and CEA as set forth above, with the respective level in one or more other samples obtained from the same subject at a different time point. Samples that may be employed in the monitoring include, but are not limited to, samples collected at different time points after diagnosis of breast cancer and/or before, during, and after therapeutic intervention, e.g. by surgery, radiation therapy, chemotherapy, any other suitable therapeutic treatment, or any combination thereof, to relieve or cure breast cancer. In some embodiments, said monitoring is carried out by repeating the assaying step at least twice at different time points, wherein said time points are selected, independently from each other, from the time points set forth above. In some embodiments, the monitoring is carried out during or after treatment of breast cancer, and/or the method comprises determining said subject as having relapse or recurrence of breast cancer or as being at risk of relapse or recurrence of breast cancer, if the level of at least one of the biomarkers is higher than in one or more earlier samples obtained from the same subject, or higher than in a relevant control or above a predetermined threshold value.

In some embodiments, the present method is particularly suitable for early diagnosis of breast cancer and early detection of breast cancer relapse, recurrence and progression. Accordingly, $CA15-3^{MGL}$ and/or $CA15-3^{WGA}$, optionally in combination with one or more biomarkers selected from the group consisting of $CA15-3^{DSL}$, $CA15-3^{GAL4}$, CA15-3, $CA125^{LECTIN}$, CA125, $CEA^{LECTIN}$, and CEA as set forth above, may serve as early tumor markers for breast cancer as well as for breast cancer relapse, recurrence and/or progression. Thus, the present method and any biomarker combinations disclosed herein may be used not only for diagnostic, prognostic and monitoring purposes but also for screening of asymptomatic women for breast cancer or a risk of developing breast cancer.

In some aspects, the present disclosure also provides use of $CA15-3^{LECTIN}$, preferably $CA15-3^{MGL}$, as a biomarker for determining a subject's disease state other than breast cancer. The inventors have experimental evidence that $CA15-3^{MGL}$ biomarker may be used for identifying subjects correctly as either subjects with epithelial ovarian cancer (EOC) or endometriosis, or as apparently healthy. Accordingly, the present disclosure provides use of $CA15-3^{LECTIN}$, preferably $CA15-3^{MGL}$, as a biomarker for determining a subject's EOC disease state, or for diagnosing, prognosing, or monitoring EOC. Also provided is a method of determining EOC disease state in a subject, as well as a method of diagnosing, prognosing, or monitoring EOC in a subject, wherein the method comprises assaying a sample obtained from said subject for $CA15-3^{LECTIN}$, preferably for $CA15-3^{MGL}$. Increased level of said $CA15-3^{LECTIN}$, preferably said $CA15-3^{MGL}$, is indicative that said subject has or is at risk of having EOC. Optionally, said $CA15-3^{LECTIN}$, preferably said $CA15-3^{MGL}$, may be used in any combination with one or more conventional breast cancer-associated biomarkers including, but not limited to, CA125, CEA, and CA15-3, and/or one or more lectin-binding species of thereof including, but not limited to, $CA125^{MGL}$, $CEA^{DC-SIGN}$ and/or $CEA^{MBL}$. Accordingly, the methods of determining EOC disease state in a subject or screening, diagnosing, prognosing, or monitoring EOC in a subject may further comprise assaying a sample obtained from said subject for one or more of the further biomarkers set for above. Any details of the embodiments disclosed herein with respect to breast cancer apply to embodiments concerning EOC, even if not repeated herein.

In some further embodiments, any biomarker combinations disclosed with respect to breast cancer may also be used for determining a subject's EOC disease state, or for screening, diagnosing, prognosing, or monitoring EOC in a subject.

In some other aspects, the present disclosure provides multiple uses of various lectin-binding species of biomarkers associated with gastrointestinal cancers, such as colorectal cancer, and pancreatic cancer, as exemplified in more detail below. Also, provided is a method of determining a state of a gastrointestinal cancer in a subject, as well as a method of screening, diagnosing, prognosing, or monitoring a gastrointestinal cancer in a subject. Any details of the embodiments disclosed herein with respect to breast cancer apply to embodiments concerning gastrointestinal cancers, even if not repeated herein.

In some embodiments, the present disclosure also provides use of $CA15-3^{LECTIN}$ (e.g. $CA15-3^{MGL}$ and/or $CA15-3^{WGA}$, optionally in combination with $CA15-3^{DSL}$ and/or $CA15-3^{GAL4}$) as a biomarker for determining a subject's disease state of colorectal cancer, or for screening, diagnosing, prognosing, or monitoring colorectal cancer in said subject. Also provided is a method of determining colorectal cancer disease state in a subject, as well as a method of screening, diagnosing, prognosing, or monitoring colorectal cancer in a subject, wherein the method comprises assaying a sample obtained from said subject for said $CA15-3^{LECTIN}$. Increased level of said $CA15-3^{LECTIN}$ would be indicative that said subject has or is at risk of having colorectal cancer. Optionally, said $CA15-3^{LECTIN}$ may be used in any combination with one or more conventional colorectal cancer-associated biomarkers including, but not limited to, CEA, CA19-9, CA125, and CA15-3, and/or one or more lectin-binding species thereof including, but not limited to, $CEA^{LECTIN}$ (e.g. $CEA^{MBL}$, $CEA^{DC-SIGN}$ and/or $CEA^{MGL}$), $CA19-9^{LECTIN}$ (e.g. $CA19-9^{DC-SIGN}$), and $CA125^{LECTIN}$ (e.g. $CA125^{MGL}$). Accordingly, the methods of determining colorectal cancer disease state in a subject or screening, diagnosing, prognosing, or monitoring colorectal cancer in a subject may further comprise assaying a sample obtained from said subject for one or more of the further biomarkers set for above.

According to experimental evidence by the inventors, MGL, Dendritic Cell-Specific Intercellular adhesion molecule-3-Grabbing Non-integrin (DC-SIGN) and Mannose Binding Lectin (MBL) show high reactivity with several colorectal cancer-derived CEA preparations. Thus, $CEA^{MBL}$, $CEA^{DC-SIGN}$ and/or $CEA^{MGL}$ are particularly potent biomarkers for use in various aspects of colorectal cancer diagnostics set forth above, and may be used either alone or in any combination with one or more conventional colorectal cancer-associated biomarkers including, but not limited to, CEA, CA19-9, CA125, and CA15-3, and/or one or more lectin-binding species thereof selected from the group consisting of including, but not limited to, $CA19-9^{LECTIN}$ (e.g. $CA199^{DC-SIGN}$), and $CA125^{LECTIN}$ (e.g. $CA125^{MGL}$), $CA15-3^{LECTIN}$ (e.g. $CA15-3^{MGL}$ and/or $CA15-3^{WGA}$, optionally in combination with $CA15-3^{DSL}$ and/or $CA15-3^{GAL4}$), and further $CEA^{LECTIN}$ species.

As demonstrated in Example 5, different glycovariant CEA assays, namely assays for $CEA^{DC-Sign}$, $CEA^{MGL}$ or $CEA^{MBL}$ can improve the colorectal cancer specificity of CEA tumor marker. CRC patients and healthy controls having plasma CEA levels in the normal range were differentially detected with the lectin glycovariant CEA assays, with increased amount of CEA glycoforms in CRC. The number of false-negatives significantly decreased using $CEA^{DC-Sign}$, $CEA^{MGL}$ or $CEA^{MBL}$ assay. Thus, some preferred embodiments of the present methods and uses relating to colorectal cancer are based on and/or comprise assaying a sample obtained from a subject whose colorectal cancer disease state is to be determined for i) $CEA^{MBL}$ with or without CEA; ii) $CEA^{DC-SIGN}$ with or without CEA; iii) $CEA^{MGL}$ with or without CEA; iv) $CEA^{MBL}$ and $CEA^{DC-SIGN}$ with or without CEA; v) $CEA^{MBL}$ and $CEA^{MGL}$ with or without CEA; vi) $CEA^{DC-SIGN}$ and $CEA^{MGL}$ with or without CEA; or vi) $CEA^{MBL}$, $CEA^{DC-SIGN}$ and $CEA^{MGL}$ with or without CEA. Any embodiments and details thereof disclosed herein with respect to other cancers, especially breast cancer, apply to the embodiments concerning colorectal cancer, even though not repeated herein.

Carbohydrate antigen (CA19-9) is a widely used biomarker especially for pancreatic cancer. However, its expression is elevated also in many other gastrointestinal cancers, including colorectal cancer and liver cancer. Accordingly, one or more lectin-binding glycoforms of CA19-9, collectively referred to herein as $CA19-9^{LECTIN}$, may in some embodiments of the present methods be used as further markers for determining a subject's disease state of a gastrointestinal cancer, such as colorectal cancer, and pancreatic cancer. A preferred CA19-9 species is $CA19-9^{DC-SIGN}$. In some non-limiting embodiments, cut-off values such as about 26 U/ml or about 37 U/ml may be employed for CA19-9.

In some embodiments, the present disclosure also provides use of $CA15-3^{LECTIN}$ (e.g. $CA15-3^{MGL}$ and/or $CA15-3^{WGA}$, optionally in combination with $CA15-3^{DSL}$ and/or $CA15-3^{GAL4}$) as a biomarker for determining a subject's disease state of pancreatic cancer, or for screening, diagnosing, prognosing, or monitoring pancreatic cancer in said subject. Also provided is a method of determining pancreatic cancer disease state in a subject, as well as a method of screening, diagnosing, prognosing, or monitoring pancreatic cancer in a subject, wherein the method comprises assaying a sample obtained from said subject for $CA15-3^{LECTIN}$. Increased level of said $CA15-3^{LECTIN}$ would be indicative that said subject has or is at risk of having pancreatic cancer. Optionally, said $CA15-3^{LECTIN}$ may be used in any combination with one or more conventional pancreatic cancer-associated biomarkers including, but not limited to, CEA, CA19-9, CA125, and CA15-3, and/or one or more lectin-binding species thereof including, but not limited to, $CEA^{LECTIN}$ (e.g. $CEA^{DC-SIGN}$ and/or $CEA^{MBL}$), $CA19-9^{LECTIN}$ (e.g. $CA199^{DC-SIGN}$), and $CA125^{LECTIN}$ (e.g. $CA125^{MGL}$). Accordingly, the methods of determining pancreatic cancer disease state in a subject or screening, diagnosing, prognosing, or monitoring pancreatic cancer in a subject may further comprise assaying a sample obtained from said subject for one or more of the further biomarkers set for above.

As demonstrated in Example 6, $CA19-9^{DC-SIGN}$ improved the discrimination of pancreatic cancer patients from healthy controls and benign controls (i.e. patients having benign disease of the liver or biliary tract) compared to the conventional CA19-9 immunoassay. Moreover, the $CA19-9^{DC-SIGN}$ assay decreased the number of false-negatives, significantly improving the sensitivity. Thus, some preferred embodiments of the present methods and uses relating to pancreatic cancer are based on and/or comprise assaying a sample obtained from a subject whose pancreatic cancer disease state is to be determined for $CA19-9^{DC-SIGN}$ with or without assaying for the conventional CA19-9 antigen. Any embodiments and details thereof disclosed herein with respect to other cancers, especially breast cancer, apply to the embodiments concerning pancreatic cancer, even though not repeated herein.

Alternatively, any appropriate combination of lectin-binding biomarker species selected from the group consisting of $CEA^{LECTIN}$ (e.g. $CEA^{MBL}$ $CEA^{DC-SIGN}$ and/or $CEA^{MGL}$), $CA19-9^{LECTIN}$ (e.g. $CA19-9^{DC-SIGN}$), $CA125^{LECTIN}$ (e.g. $CA125^{MGL}$), and $CA15-3^{LECTIN}$ (e.g. $CA15-3^{MGL}$ and/or $CA15-3^{WGA}$, optionally in combination with $CA15-3^{DSL}$ and/or $CA15-3^{GAL4}$), optionally with any desired combination of conventional CEA, CA19-9, CA125, and CA15-3, may be employed in any of the embodiments set forth above relating to gastrointestinal cancers, including colorectal cancer, and pancreatic cancer. In a non-limiting more specific alternative, $CEA^{MBL}$, $CEA^{DC-SIGN}$ and/or $CEA^{MGL}$ are used in any combination with one or more conventional gastrointestinal cancer-associated biomarkers including, but not limited to, CEA, CA19-9, CA125, and CA15-3, and/or one or more lectin-binding species thereof selected from the group consisting of $CA19-9^{LECTIN}$ (e.g. $CA19-9^{DC-SIGN}$), and $CA125^{LECTIN}$ (e.g. $CA125^{MGL}$), $CA15-3^{LECTIN}$ (e.g. $CA15-3^{MGL}$ and/or $CA15-3^{WGA}$, optionally in combination with $CA15-3^{DSL}$ and/or $CA15-3^{GAL4}$), and further $CEA^{LECTIN}$ species. In some further embodiments, any biomarker combinations disclosed with respect to breast cancer may also be used for determining a state of a gastrointestinal cancer in a subject, or for screening, diagnosing, prognosing, or monitoring a gastrointestinal cancer in a subject, wherein said gastrointestinal cancer includes, but is not limited to colorectal cancer and pancreatic cancer.

Furthermore, in one aspect, the present disclosure provides use of one or more lectin-binding species of prostate specific antigen, i.e. $PSA^{LECTIN}$, preferably $PSA^{MGL}$, one or more $CEA^{LECTIN}$ species, such as $CEA^{MBL}$, $CEA^{DC-SIGN}$ and/or $CEA^{MGL}$, and/or one or more $CA19-9^{LECTIN}$ species such as $CA19-9^{DC-SIGN}$, either alone or in any combination thereof, for use as biomarkers for determining a subject's disease state of prostate cancer, or for screening, diagnosing, prognosing, or monitoring prostate cancer in said subject. Optionally, any one or more of the lectin-binding biomarkers set forth above may be used in any combination with conventional PSA, CEA, and/or CA19-9 biomarkers. In some specific embodiments, lectin-binding biomarker species to be assayed for include, but are not limited to:

$PSA^{MGL}$;
$CEA^{DC\text{-}SIGN}$;
$CEA^{MBL}$;
$CA19\text{-}9^{LECTIN}$;
$PSA^{MGL}$ and $CEA^{DC\text{-}SIGN}$;
$PSA^{MGL}$ and $CEA^{MBL}$;
$PSA^{MGL}$ and $CA19\text{-}9^{LECTIN}$;
$CEA^{DC\text{-}SIGN}$ and $CEA^{MBL}$;
$CEA^{DC\text{-}SIGN}$ and $CA19\text{-}9^{LECTIN}$;
$CEA^{MBL}$ and $CA19\text{-}9^{LECTIN}$;
$PSA^{MGL}$, $CEA^{DC\text{-}SIGN}$, and $CEA^{MBL}$;
$PSA^{MGL}$, $CEA^{DC\text{-}SIGN}$, and $CA19\text{-}9^{LECTIN}$;
$PSA^{MGL}$, $CEA^{MBL}$, and $CA19\text{-}9^{LECTIN}$;
$CEA^{DC\text{-}SIGN}$, $CEA^{MBL}$, and $CA19\text{-}9^{LECTIN}$; or
$PSA^{MGL}$, $CEA^{DC\text{-}SIGN}$, $CEA^{MBL}$, and $CA19\text{-}9^{LECTIN}$.

Assaying a sample for any one of the specific biomarker combinations set forth above may further comprise assaying also for one or more conventional biomarkers selected from PSA, CEA and CA19-9.

As demonstrated in Example 7, $PSA^{MGL}$ can discriminate between the cancerous and non-cancerous PSA antigen. Thus, some preferred embodiments of the present methods and uses relating to prostate cancer are based on and/or comprise assaying a sample obtained from a subject whose prostate cancer disease state is to be determined for $PSA^{MGL}$ with or without assaying for the conventional PSA antigen. Any embodiments and details thereof disclosed herein with respect to other cancers, especially breast cancer, apply to the embodiments concerning prostate cancer, even though not repeated herein.

In some further embodiments, $PSA^{WGA}$, $PSA^{Gal4}$ and/or $PSA^{Dectin2}$ may be used for determining prostate cancer disease state in a subject. Thus, some embodiments of the present methods and uses relating to prostate cancer are based on and/or comprise assaying a sample obtained from a subject whose prostate cancer disease state is to be determined for $PSA^{WGA}$, $PSA^{Gal4}$ or $PSA^{Dectin2}$; $PSA^{MGL}$ and $PSA^{WGA}$; $PSA^{MGL}$ and $PSA^{Gal4}$; $PSA^{MGL}$ and $PSA^{Dentin2}$; $PSA^{WGA}$ and $PSA^{Gal4}$; $PSA^{WGA}$ and $PSA^{Dentin2}$; $PSA^{Gal4}$ and $PSA^{Dentin2}$; $PSA^{MGL}$, $PSA^{WGA}$ and $PSA^{Gal4}$; $PSA^{MGL}$ $PSA^{WGA}$ and $PSA^{Dentin2}$; $PSA^{WGA}$ $PSA^{Gal4}$ and $PSA^{Dentin2}$; $PSA^{MGL}$ $PSA^{Gal4}$ and $PSA^{Dentin2}$; or $PSA^{MGL}$, $PSA^{WGA}$, $PSA^{Gal4}$ and $PSA^{Dentin2}$. Any of these embodiments may also comprise assaying for the conventional PSA antigen.

For the sake of simplicity, conventional cancer-associated biomarkers disclosed herein, namely CA15-3, CA125, CEA, CA19-9, or PSA, are collectively referred to by the general term "GlycoProt", while lectin-binding glycoforms thereof are referred to by the general term "$GlycoProt^{LECTIN}$". Depending on the embodiment in question, the terms may refer to one or more biomarkers or glycoforms encompassed by the terms, respectively, as is readily understood by those skilled in the art. Preferred $GlycoProt^{LECTIN}$ species include, but are not limited to, $CA15\text{-}3^{MGL}$, $CA15\text{-}3^{WGA}$, $CA15\text{-}3^{DSL}$, $CA15\text{-}3^{GAL4}$, $CA125^{MGL}$, $CEA^{DC\text{-}SIGN}$, $CEA^{MBL}$, and $PSA^{MGL}$.

Assaying a sample for any $GlycoProt^{LECTIN}$ disclosed herein may be carried out by any means, methods, or techniques available in the art. A preferred but non-limiting example is to determine the GlycoProt's level of binding to the lectin in question. This may be performed, for example, by a sandwich assay, wherein a GlycoProt-specific antibody, preferably a monoclonal antibody or a fragment therof (e.g. a Fab fragment), is used as a capturing agent and the lectin in question is used as a tracer. For use as a tracer, said lectin may be detectably labelled, either directly or indirectly.

As used herein, the term "antibody" refers to an immunoglobulin structure comprising two heavy (H) chains and two light (L) chains interconnected by disulfide bonds. Antibodies can exist as intact immunoglobulins or as any of a number of well-characterized antigen-binding fragments or single chain variants thereof, all of which are herein encompassed by the term "antibody". Non-limiting examples of said antigen-binding fragments include Fab fragments, Fab' fragments, F(ab')2 fragments, and Fv fragments. Said fragments and variants may be produced by recombinant DNA techniques, or by enzymatic or chemical separation of intact immunoglobulins as is well known in the art. The term "antibody" also includes, but is not limited to, polyclonal, monoclonal, and recombinant antibodies of isotype classes IgA, IgD, IgE, IgG, and IgM and subtypes thereof In some other embodiments, a sandwich assay may be conducted using a reversed way. In such cases, lectin in question is used as a capturing agent and a GlycoProt-specific antibody, preferably a monoclonal antibody, as a directly or indirectly detectably labelled tracer. Since urine contains less interfering glycosylated molecules than blood, the reversed sandwich assay may operate better with urine samples than with blood samples.

In some embodiments, a sandwich assay may comprise one or more washing steps after a capturing step in order to remove any GlycoProt species not specific for the capturing agent. Appropriate washing solutions and conditions (e.g. time and temperature) are known to those skilled in the art.

Sandwich assays according to various embodiments of the present invention may be performed either on a solid surface, such as a microtiter plate, or in lateral flow format. Means and methods for binding a capturing agent to a solid surface, e.g. via a streptavidin-biotin complex, or incorporating a capturing agent to a lateral flow assay are known in the art and readily apparent to a skilled person.

Suitable substrates for use in the present solid phase sandwich assays include, but are not limited to, glass, silica, aluminosilicates, borosilicates, metal oxides such as alumina and nickel oxide, gold, various clays, nitrocellulose or nylon. As indicated above, the substrate may in some embodiments be coated with an appropriate compound to enhance binding of a capturing agent (i.e. either an anti-GlycoProt antibody or a lectin) to the substrate. In some further embodiments, one or more control antibodies or control lectins may also be attached to the substrate.

Any one or more, preferably monoclonal, anti-GlycoProt antibodies may be used in the above-mentioned sandwich assays either as capturing agents or as tracers. Non-limiting examples of suitable commercial anti-CA15-3 antibodies include Ma552 and Ma695, while non-limiting examples of suitable commercial anti-CA125 antibodies include Ov185, Ov197, and OvK95, available at least from Fujirebio Diagnostics, Sweden. Further GlycoProt-specific monoclonal antibodies are available in the art or may be produced according to methods well known in the art. For use as a tracer, an anti-GlycoProt antibody may be labelled with any appropriate label known in the art including, but not limited, to fluorescent labels, bioluminescent labels, chemiluminescent labels. In some embodiments, said anti-GlycoProt antibody may detectably labelled indirectly, for example through immobilization to a detectable nanoparticle.

Lectins are commercially available from multiple sources. Some lectins, such as MGL and DC-SIGN, are available with or without C-terminal fusion to human IgG1-Fc. Both forms may be employed in the present methods. In some embodiments, the Fc-fused forms are preferred.

For use as a tracer, lectins may be detectably labelled by various ways as is well known in the art. In some embodiments, one or more lectins to be employed for assaying a sample for the level of GlycoProt$^{LECTIN}$ may be directly labelled with any available detectable label using standard techniques. For example, GlycoProt$^{LECTIN}$ may be directly labelled with a lanthanide chelate, such as an europium (III), terbium (III), samarium (III), dysprosium (III), ytterbium (III), erbium (III) or neodynium (III) chelate, or made detectable through colorimetric detection, e.g. by conjugating the GlycoProt$^{LECTIN}$ with horseradish peroxidase (HRP) or alkaline phosphatase (AP). In some other embodiments, one or more lectins to be employed may be detectably labelled indirectly, for example by immobilizing said one or more lectins on a detectable nanoparticle. Such nanoparticleimmobilized lectins are called lectin-NPs for short.

As used herein, the term "nanoparticle" (NP) refers to a particle, synthetic or natural, having one or more dimensions, e.g. a diameter, of less than about 1000 nm, e.g. about 500 nm or less, about 100 nm or less, or about 50 nm or less. As used herein, the term "about" refers to a range of values±10% of a specified value. For example, the phrase "about 100 nm" includes ±10% of 100 nm, or from 90 nm to 110 nm. The nanoparticles may generally have a spherical shape but also non-spherical shapes such as ellipsoidal shapes can be used. In some embodiments, all the dimensions of said nanoparticle are less than about 1000 nm, about 500 nm or less, about 100 nm or less, or about 50 nm or less.

A variety of different materials may be utilized in the present nanoparticles. Non-limiting examples of suitable polymers include poly(ethylene glycol) (PEG), polystyrene, polyethylene, poly(acrylic acid), poly(methyl methacrylate) (PMMA), polysaccharides, and copolymers or combinations thereof. Other suitable nanoparticle materials include, but are not limited to, colloidal gold, silver, quantum dots, carbon, porous silicon, and liposomes. Further suitable nanoparticle materials include protein nanoparticles, mineral nanoparticles, glass nanoparticles, nanoparticle crystals, metal nanoparticles, and plastic nanoparticles.

Nanoparticles suitable for use in various embodiments of the present invention or disclosure, may be directly or indirectly qualitatively or quantitatively detectable by any known means. For instance, the nanoparticles may be detectable owing to an inherent quality as in the case of e.g. upconverting nanoparticles (UCNP), resonance particles, quantum dots, and gold particles. In some other embodiments, the nanoparticles can be made detectable e.g. by fluorescent labels, bioluminescent labels, chemiluminescent labels. In some further embodiments, labelling or doping with lanthanides, i.e. luminescent lanthanide ions with luminescence emission in visible or near-infrared or infrared wavelengths and long fluorescence decay, such as europium (III), terbium (III), samarium (III), dysprosium (III), ytterbium (III), erbium (III) and neodynium (III), are preferred means for making the present nanoparticles detectable.

Lectins may be immobilized on nanoparticles by any suitable method known in the art, including but not limited to that disclosed in Example 1. In those embodiments which involve more than one different lectin, said different lectins may be immobilized either on the same or different nanoparticles in any desired ratios.

In some non-limiting embodiments, the most preferred nanoparticles are polystyrene nanoparticles having a diameter of either about 97 nm or about 107 nm. Such nanoparticles are commercially available at least from Thermo Scientific Seradyn Inc. Further preferred nanoparticles include europium chelate-doped nanoparticles. Advantages of such nanoparticles include i) signal amplification provided by a great number of chelates per particle, ii) strengthened functional affinity (avidity) of the lectins to their target glycostructure epitopes enabled by the high density of immobilized lectins on the particle, and iii) the glycostructure specificity of the lectins used as enabled by creation of the multivalent nanoparticles. However, nanoparticles are only one preferred way of providing adequate avidity effect and signal amplification for carrying out the present invention or disclosure and their various embodiments.

Furthermore, in those embodiments which involve more than one different lectin, a sample may be assayed for different GlycoProt$^{LECTIN}$ species either in a same assay (i.e. concomitantly) or in different assays (i.e. in parallel), either simultaneously or sequentially. In any such assays, said different lectins may have been detectably labelled, either directly or indirectly, with same of different labels. In some embodiments, multiplexing, for example, by using differently labelled nanoparticles bearing different lectin species in a single assay may be a preferred format for carrying out any of the methods or embodiments thereof disclosed herein.

In some specific embodiments, one or more lectins immobilized on a same or different nanoparticles labelled with a detectable label such as a lanthanide chelate selected from europium(III), terbium(III), samarium(III), and dysprosium (III) are used as tracers. In some more specific embodiments, europium chelate is used as a detectable label. In a non-limiting preferred embodiment, lectin-NP is used as a tracer and is doped with about 30000 Eu-chelates. In some other specific embodiments, lectin in question is attached on upconverting phosphorus (UCP) particles, which are particularly suitable for use as tracers in the lateral flow format.

It is also possible to create a detectable signal by using any available sensor technology. For example, a solid surface may incorporate a recognition element (transducer) capable of converting the binding reaction into a detectable signal with or without the use of label moieties. Different types of transducers can be employed, including those based on electrochemical or optical detection. Detection may also be based on either homogeneous or heterogeneous detection techniques, as is apparent to those skilled in the art.

Coating the lectins on the surface of nanoparticles instead of coating them onto solid surfaces such as microtiter wells, arrays or sensors, brings about significant benefits in terms of assay performance especially in non-competitive assay formats where the lectins are used in combination with specific antibodies. When such antibodies are bound to the solid phase, the typically significantly higher affinity of antibodies as compared to that of lectins can be exploited in full to capture the target biomarker molecules onto the solid phase with high efficiency and stability as the first step. Given the high affinity of antibodies, also small target molecules with only one copy of the targeted epitope can be captured with high stability. Once the target molecules are captured, the avidity effect of the lectin nanoparticles, i.e. the effect where several adjoining lectins can bind to adjoining captured target molecules thereby significantly increasing the binding force compared to singular lectin molecules, can also be utilized in full.

Further combined with the fact that the nanoparticles typically allow significant intensification of the measurable signal, the lectin-NP/solid-phase-antibody approach optimally combines the high specificity of both binding partners, the high binding force of singular antibodies, the high binding force of multiple adjoining lectins on multiple adjoining glycostructures (the avidity effect), and the high level of signal detectable for each bound nanoparticle, resulting in the optimal combination of high sensitivity and high specificity, both in terms of both analytical and clinical attributes.

Furthermore, while lectins typically have a high specificity against the target glycostructures (glycoforms), such forms may also exist in other molecules than the targeted one. Therefore, in some preferred embodiments, a wash step is employed between the target molecule antibody capture phase and the lectin-NP binding phase, to wash out all non-targeted and unbound molecules that may in some cases comprise the same glycostructures as the targeted molecules and hence pose a risk of unspecific detection based on cross-reactivity between species. Once the specific target molecules are captured by the use of antibodies, and other molecules washed away before the lectin binding step, the risk of unspecific binding of unwanted targets by lectins becomes eliminated. Such a wash step is also preferred to prevent competition of the target molecule for binding to distant sites around the lectin-NP, although this would occur with a low affinity in many cases. However, both the risk of cross-reactivity and distant binding increase when the target molecule has several reactive glycostructures like in the case of many molecules with high molecular weight, such as CA15-3, where adjoining lectins can bind to adjoining glycostructures in the same target molecule. In such case the use of the non-competitive lectin-NP/solid-phase-antibody approach with a wash step before the lectin-NP binding reaction results in a significantly more sensitive and target specific assay compared to platforms where the lectins are bound to the solid phase, or where the lectin-NPs are employed without an intermediate wash step. Similarly, because of an almost complete lack of the avidity effect, assay platforms where the lectins (instead of the antibodies) are bound to the solid phase have poor performance with small target molecules such as PSA which only has one glycostructure moiety per molecule.

The present disclosure also provides a kit for use in the present methods and various embodiments thereof. In its broadest form, the kit comprises reagents for assaying one or more lectin-binding species of cancer-associated glycoprotein biomarkers selected from the group consisting of CA15-3, CA125, CEA, C19-9, and PSA. In other words, the kit comprises reagents for assaying a sample for any desired GlycoProt$^{LECTIN}$ species or combination thereof selected from the group consisting of CA15-3$^{LECTIN}$, CA125$^{LECTIN}$, CEA$^{LECTIN}$, CA19-9$^{LECTIN}$, and PSA$^{LECTIN}$. For each GlycoProt$^{LECTIN}$ to be assayed, at least one reagent is a GlycoProt-binding agent specific for the GlycoProt in question, such as monoclonal anti-GlycoProt antibody, and at least one of the reagents is the lectin in question, preferably immobilized on a nanoparticle. Either said GlycoProt-binding agent or said lectin is detectably labelled. The lectin may be indirectly labelled through a detectable nanoparticle on which it is immobilized. GlycoProt$^{LECTIN}$ species to be assayed for, and thus the reagents to be included in the kit, depend on the intended purpose of using the kit, especially on cancer that is to be screened, diagnosed, prognosed, or monitored, and preferred combinations become apparent from the disclosure above.

Optionally, the kit may also comprise reagents for assaying one or more conventional GlycoProt antigens, preferably selected from the group consisting of CA15-3, CA125, CA19-9, CEA, and PSA. Non-limiting examples of typical reagents for assaying said conventional GlycoProt antigens include two GlycoProt-binding agents for each conventional GlycoProt antigen to be assayed, such as two monoclonal anti-GlycoProt antibodies, which bind to different epitopes in said GlycoProt. For each specific GlycoProt, one of the binding agents may be the same as the GlycoProt-binding agent provided for assaying a respective GlycoProt$^{LECTIN}$. Nevertheless, one of the GlycoProt-binding agents may be immobilized on a solid surface or provided for use as a capturing agent in lateral flow format, while the other GlycoProt-binding agent may comprise a detectable label. Conventional GlycoProt antigens to be assayed for, and thus the reagents to be included in the kit, depend on the intended purpose of using the kit, especially on cancer that is to be screened, diagnosed, prognosed, or monitored, and preferred combinations become apparent from the disclosure above.

In some embodiments, the kit is provided for determining a subject's breast cancer disease state, or for screening, diagnosing, prognosing, or monitoring breast cancer in said subject. In such cases, the kit comprises a CA15-3 binding agent, such as a monoclonal anti-CA15-3 antibody, and MGL and/or WGA, optionally immobilized onto a same or a different nanoparticle. In some further embodiments, also DSL and/or Gal4 may be provided, optionally as immobilized onto a same or different nanoparticle. Either said CA15-3 binding agent or said lectin comprises a detectable label or has been immobilized on a solid surface, such as a microtiter plate. In some further embodiments, streptavidin coating of the plates and biotinylation of the antibody are used for said attaching. Alternative ways of achieving the same are readily available for a skilled person.

In some further embodiments, a kit provided for determining a subject's breast cancer disease state, or for screening, diagnosing, prognosing, or monitoring breast cancer in said subject may also comprise reagents for assaying additional biomarkers selected from the group consisting of, CA15-3, CA125$^{LECTIN}$(e.g. CA125$^{MGL}$), CA125, CEA$^{LECTIN}$ (e.g. CEA$^{MBL}$, CEA$^{DC-SIGN}$ and/or, CEA$^{MGL}$) and CEA. Suitable reagents for these assays become apparent from above.

Accordingly, in some embodiments, especially concerning breast cancer, the kit may further comprise one or more reagents for assaying CA15-3 protein concentration. Non-limiting examples of typical reagents for assaying CA15-3 protein concentration include two CA15-3 binding agents, such as two monoclonal anti-CA15-3 antibodies, which bind to different protein epitopes in CA15-3. One of the CA15-3 binding agents may be the same as the CA15-3 binding agent provided for assaying CA15-3$^{MGL}$ or CA15-3$^{WGA}$. One of the two CA15-3 binding agents may be immobilized on a solid surface or provided for use as a capturing agent in lateral flow format, while the other CA15-3 binding agent may comprise a detectable label. Alternatively or in addition, corresponding reagents may be comprised in the kit for assaying a sample for CA125 and/or CEA.

Optionally, the kit may also comprise a control for comparing to a measured value of CA15-3 binding to MGL and/or WGA. In some embodiments, the control is a threshold value for comparing to the measured value.

In some embodiments, a kit is provided for determining a subject's colorectal cancer disease state, or for screening, diagnosing, prognosing, or monitoring colorectal cancer in said subject. In such cases, the kit comprises a CEA-binding agent, such as a monoclonal anti-CEA antibody, and at least one lectin selected from the group consisting of MBL DC-SIGN and MGL, optionally immobilized onto a nanoparticle. If more than one lectin is to be used, the may be immobolized onto same or different nanoparticles. In some embodiments, the lectin to be used may be CEA$^{MBL}$, CEA$^{DC-SIGN}$ or CEA$^{MGL}$, while in other embodiments lectins $CEA^{MBL}$ and $CEA^{DC\text{-}SIGN}$; $CEA^{MBL}$ and $CEA^{MGL}$; $CEA^{DC\text{-}SIGN}$ and $CEA^{MGL}$; or CEA; or $CEA^{MBL}$, $CEA^{DC\text{-}SIGN}$ and $CEA^{MGL}$ are used in combination. Either said CEA-binding agent or said lectin comprises a detectable label or has been immobilized on a solid surface, such as a microtiter plate. In some further embodiments, streptavidin coating of the plates and biotinylation of the antibody are used for said attaching. Alternative ways of achieving the same are readily available for a skilled person.

In some further embodiments, a kit provided for determining a subject's colorectal cancer disease state, or for screening, diagnosing, prognosing, or monitoring colorectal cancer in said subject may also comprise reagents for assaying additional biomarkers such as CEA. Accordingly, in some embodiments, the kit may further comprise one or more reagents for assaying CEA protein concentration. Suitable reagents for this purpose are readily available in the art and include, but are not limited to, monoclonal anti-CEA antibodies. In some embodiments, two monoclonal anti-CEA antibodies, which bind to different protein epitopes in CEA may be employed. One of the CEA binding agents may be the same as the CEA-binding agent provided for assaying $CEA^{MBL}$, $CEA^{DC\text{-}SIGN}$ and/or $CEA^{MGL}$. One of the two CEA binding agents may be immobilized on a solid surface or provided for use as a capturing agent in lateral flow format, while the other CEA-binding agent may comprise a detectable label.

Optionally, the kit may also comprise a control for comparing to a measured value of CEA binding to MBL, DC-SIGN and/or MGL. In some embodiments, the control is a threshold value for comparing to the measured value.

In some embodiments, a kit is provided for determining a subject's pancreatic cancer disease state, or for screening, diagnosing, prognosing, or monitoring pancreatic cancer in said subject. In such cases, the kit comprises a CA19-9-binding agent, such as a monoclonal anti-CA19-9 antibody, and at least one lectin, preferably DC-SIGN, optionally immobilized onto a nanoparticle. Either said CA19-9-binding agent or said lectin comprises a detectable label or has been immobilized on a solid surface, such as a microtiter plate. In some further embodiments, streptavidin coating of the plates and biotinylation of the antibody are used for said attaching. Alternative ways of achieving the same are readily available for a skilled person.

In some further embodiments, a kit provided for determining a subject's pancreatic cancer disease state, or for screening, diagnosing, prognosing, or monitoring pancreatic cancer in said subject may also comprise reagents for assaying additional biomarkers such as CA19-9. Accordingly, in some embodiments, the kit may further comprise one or more reagents for assaying CA19-9 protein concentration. Suitable reagents for this purpose are readily available in the art and include, but are not limited to, monoclonal anti-CA19-9 antibodies. In some embodiments, two monoclonal anti-CA19-9 antibodies, which bind to different protein epitopes in CA19-9 may be employed. In such cases, one of the CA19-9 binding agents may be the same as the CA19-9-binding agent provided for assaying CA19-9$^{DC\text{-}SIGN}$. One of the two CA19-9 binding agents may be immobilized on a solid surface or provided for use as a capturing agent in lateral flow format, while the other CA19-9-binding agent may comprise a detectable label.

Optionally, the kit may also comprise a control for comparing to a measured value of CA19-9 binding to DC-SIGN. In some embodiments, the control is a threshold value for comparing to the measured value.

In some embodiments, a kit is provided for determining a subject's prostate cancer disease state, or for screening, diagnosing, prognosing, or monitoring prostate cancer in said subject. In such cases, the kit comprises a PSA-binding agent, such as a monoclonal anti-PSA antibody or an antigen-binding fragment thereof, and at least one lectin, preferably MGL, optionally immobilized onto a nanoparticle. Either said PSA binding agent or said lectin comprises a detectable label or has been immobilized on a solid surface, such as a microtiter plate. In some further embodiments, streptavidin coating of the plates and biotinylation of the antibody are used for said attaching. Alternative ways of achieving the same are readily available for a skilled person.

In some further embodiments, a kit provided for determining a subject's prostate cancer disease state, or for screening, diagnosing, prognosing, or monitoring prostate cancer in said subject may also comprise reagents for assaying additional biomarkers such as PSA. Accordingly, in some embodiments, the kit may further comprise one or more reagents for assaying PSA protein concentration. Suitable reagents for this purpose are readily available in the art and include, but are not limited to, monoclonal anti-PSA antibodies and antigen-binding fragments thereof. In some embodiments, two monoclonal anti-PSA antibodies, which bind to different protein epitopes in PSA may be employed. In such cases, one of the PSA binding agents may be the same as the PSA-binding agent provided for assaying $PSA^{MGL}$. One of the two PSA-binding agents may be immobilized on a solid surface or provided for use as a capturing agent in lateral flow format, while the other PSA-binding agent may comprise a detectable label.

Optionally, the kit may also comprise a control for comparing to a measured value of PSA binding to MGL. In some embodiments, the control is a threshold value for comparing to the measured value.

In some further embodiments, the kit may also comprise a computer readable medium comprising computer-executable instructions for performing any method of the present disclosure.

In addition to the reagents for assaying a sample for the biomarker combinations set forth above, the kit may also comprise reagents for assaying said samples for any other biomarker, especially for one or more biomarkers associated with any disease other than the cancer in question, such as other cancers. Thus, the kit may be used not only for screening, diagnosing, prognosing, or monitoring cancer but also for screening, diagnosing, prognosing, or monitoring, for example, other cancers, depending on the specificity and sensitivity of the one or more other biomarkers whose concentrations are to be assayed.

Various details and embodiments of the present method apply also to the present kit, as is readily understood by a skilled person. Thus, properties and features of suitable nanoparticles, for instance, are not repeated herein with respect to the kit.

Also provided is the use of MGL and/or WGA, optionally in any combination with DSL and/or Gal4, or the use of any composition, such as a nanoparticle composition comprising the same, for determining a state of breast cancer in a subject, or for screening, diagnosing, prognosing, or monitoring breast cancer in a subject. Any details and specifics disclosed with respect to the present method and its embodiments apply to the various uses of these biomarkers even though the details and specifics are not repeated herein.

Also provided is the use of MBL, DC-SIGN and/or MGL, or the use of any composition, such as a nanoparticle composition comprising the same, for determining a state of colorectal cancer in a subject, or for screening, diagnosing, prognosing, or monitoring colorectal cancer in a subject. Any details and specifics disclosed with respect to the present method and its embodiments apply to the various uses of these biomarkers even though the details and specifics are not repeated herein.

Also provided is the use of DC-SIGN, or the use of any composition, such as a nanoparticle composition comprising the same, for determining a state of pancreatic cancer in a subject, or for screening, diagnosing, prognosing, or monitoring pancreatic cancer in a subject. Any details and specifics disclosed with respect to the present method and its embodiments apply to the various uses of these biomarkers even though the details and specifics are not repeated herein.

Also provided is the use of MGL, or the use of any composition, such as a nanoparticle composition comprising the same, for determining a state of prostate cancer in a subject, or for screening, diagnosing, prognosing, or monitoring prostate cancer in a subject. Any details and specifics disclosed with respect to the present method and its embodiments apply to the various uses of these biomarkers even though the details and specifics are not repeated herein.

Uses of various other lectin-binding biomarker species and any combinations thereof are also provided. Any details and characteristics of such uses become apparent from the disclosure above.

It will be obvious to a person skilled in the art that, as technology advances, the inventive concept can be implemented in various ways. The invention and its embodiments are not limited to the examples described below but may vary within the scope of the claims.

EXAMPLES

Breast Cancer

Example 1: Materials and Methods

Origin of CA15-3 and Clinical Samples

Cancerous CA15-3 from a primary breast cancer (BrCa) cell line was obtained from Fujirebio Diagnostics, Sweden.

All clinical samples were provided by University of Tampere, Finland with appropriate permissions and informed consents in accordance with the ethical guidelines of the Hospital District of Pirkanmaa. The clinical samples included a cohort of longitudinal plasma samples (n=199) from 45 different BrCa patients and serum/plasma samples from apparently healthy women as controls (HC, n=31).

Anti-CA15-3 Antibodies

Two different monoclonal anti-CA15-3 antibodies, namely Ma552 and Ma695, which detect the protein core and sialylated carbohydrate epitope of the MUC-1 (CA15-3) antigen, respectively, were obtained from Fujirebio Diagnostics, Sweden.

For use as solid-phase capture agents, the antibodies were biotinylated for 4 h at room temperature (RT) with a 40-fold molar excess of biotin isothiocyanate using a standard procedure known in the art. The biotinylated antibodies were purified with NAP-5 and NAP-10 gel-filtration columns (GE Healthcare, Schenectady, N.Y., USA) by using 50 mmol/L Tris-HCl (pH 7.75), containing 150 mmol/L NaCl and 0.5 g/L $NaN_3$. The labelled antibodies were stabilized with 1 g/L BSA (Bioreba, Nyon, Switzerland) and stored at +4° C.

Lectins

A panel of 15 plant lectins was purchased from VECTOR lab and a panel of 13 human lectins was purchased from RnD System.

TABLE 1

Lectins employed in the present experiments

| Lectin | Full name of Lectin | Major Carbohydrate binding specificities |
|---|---|---|
| SBA | Soybean agglutinin | Terminal α-or β linked GalNAc |
| SNA | *Sambucus nigra* agglutinin | sialic acid α (2-6) Gal |
| PNA | Peanut agglutinin | Galβ1-3 GalNAc (terminal) |
| MAA II | *Maackia amurensis* agglutinin II | α2-3-linked sialic acids |
| AAL | *Aleuria aurantia* lectin | α1-6Fuc |
| UEA | *Ulex europaeus* agglutinin | Fucα1-2Gal |
| PHA-E | *Phaseolus vulgaris* agglutinin-erythroagglutinin | bisecting GlcNAc |
| RCA | *Ricinus communis* agglutinin | Gal-β1-4GlcNAc |
| WGA | Wheat germ agglutinin | Terminal N-acetylglucosamine or chitobiose |
| WFA | *Wisteria floribunda* agglutinin | GalNAcα or β-3 or 6 position of galactose |
| PSA | *Pisum sativum* agglutinin | α-Mannose |
| VVL | *Vicia villosa* lectin | Terminal α-or β-linked GalNAc (Tn antigen) |
| TJA-II | *Trichosanthes japonica* agglutinin | Fuc α 1-2Gal and β-GalNAc |
| DSL | Datura Stramonium Lectin | (β-1,4) linked N-acetylglucosamine oligomers |
| HPA | *Helix pomatia* agglutinin | GalNAc (Tn antigen) |
| MGL | Macrophage galactose-type lectin | Terminal α-or β-linked GalNAc |
| DC-SIGN | Dendritic Cell-Specific Intercellular adhesion molecule-3-Grabbing Non-integrin (DC-SIGN) | Nonsialylated Lewis antigens and high mannose-type structures |
| MMR | Macrophage mannose receptor | Terminal mannose, fucose or N-acetylglucosamine |
| MBL | Mannose binding lectin | fucose, mannose/mannan |
| Siglec-2 | Sia-recognizing Ig-superfamily lectin 2 | Sia-> α6Gal-> β4GlcNac-> βR |
| Siglec-3 | Sia-recognizing Ig-superfamily lectin 3 | Sia-> α6Gal-> β4GlcNac-> βR |

TABLE 1-continued

Lectins employed in the present experiments

| Lectin | Full name of Lectin | Major Carbohydrate binding specificities |
|---|---|---|
| Siglec-5 | Sia-recognizing Ig-superfamily lectin 5 | Sia-> α3Gal-> β4GlcNac-> βR |
| Siglec-9 | Sia-recognizing Ig-superfamily lectin 9 | Sia-> α3Gal-> β4GlcNac-> βR, 6-sulfated sLe$^x$ |
| Siglec-10 | Sia-recognizing Ig-superfamily lectin 10 | Sia-> α3Gal-> β4GlcNac-> βR |
| Siglec-11 | Sia-recognizing Ig-superfamily lectin 11 | Sia-> α8Sia-> α3Gal-> β4GlcNac-> βR |
| Galectin-3 | β-galactoside binding lectins | galactomannans, mannan |
| Galectin-4 | β-galactoside binding lectins | SO$_3$->3Galβ1->3GalNAc pyranoside |
| E-selectin |  | sLe$^x$, near residues might affect affinity |

Lectins were immobilized onto europium chelate-doped, monodisperse, carboxyl-modified Fluoro-Max™ polystyrene nanoparticles (97 nm in diameter) which were obtained from Thermo Scientific Seradyn Inc., Indianapolis, Ind.). The nanoparticles employed produce a long-lifetime fluorescence equivalent to 30,000 chelated ions per particle.

Primary amino groups of lectins were covalently coupled to activated carboxyl groups of the nanoparticles using a procedure described previously with some minor modifications (Soukka et al., Anal. Chem. 2001, 73, 2254-2260). The nanoparticles (1e$^{12}$ particles) were suspended in 10 mmol/L phosphate buffer (pH 7.0), and their surfaces were activated with 0.75 mmol/L N-(3-dimethylaminopropyl)-N-ethylcarbodiimide (Sigma-Aldrich, St. Louis, Mo., USA) and 10 mmol/L N-hydroxysulfosuccinimide sodium salt (Sigma-Aldrich). The concentrations of lectins in the coupling reactions were 0.625 mg/ml, and the reactions contained 100 m mol/L NaCl. The activated particles were mixed with the lectins. The coupling reactions were incubated for 2 h at +23° C. with vigorous shaking. Final washes and blocking of the remaining active groups were performed in Tris-based buffer (10 mmol/L Tris, 0.5 g/L NaN$_3$, pH 8.5), and the nanoparticle-lectin conjugates were stored in the same buffer supplemented with 2 g/L BSA at 4° C. Before the first instance of use, the particles were mixed thoroughly, sonicated, and centrifuged lightly (350 g, 5 min) to separate non-colloidal aggregates from the monodisperse suspension.

Conventional CA15-3 Immunoassay

CA15-3 concentrations in serum were analyzed by ELISA using CanAg CA15-3 EIA kit (Fujirebio Diagnostics) according to the manufacturer's instructions. Briefly, the biotinylated capture MAb (bioMa695) and HRP conjugated tracer MAb (Ma552) were added into streptavidin (SAv) coated microtiter wells along with calibrator and clinical serum/plasma samples of 1:41 dilution. After 2 hr incubation the wells were washed six times and substrate TMB was added and optical density was measured at 450 nm after adding stop solution. The basic principle of this conventional CA15-3 immunoassay is illustrated in FIG. 1A.

Anti-CA15-3 Antibody-Lectin Nanoparticle Sandwich Assay

Red assay buffer, wash buffer and streptavidin-coated lowfluorescence microtiter plates used in these experiments were purchased from Kaivogen Oy, Turku, Finland.

Biotinylated solid-phase antibodies (100 ng), namely bioMa695 or bioMa552, were immobilized onto streptavidin-coated microtiter wells in 40 μL of the assay buffer. After 1 h incubation at RT and shaking at 900 rpm, the wells were washed two times with the wash solution and used immediately in the assays.

Next, 50 μl of diluted samples (1:40 in assay buffer) were added to each well, and incubated for 1 h at RT with shaking. CA15-3 antigens thereby captured on the wells were analysed by time-resolved fluorescence (TRF) using Eu$^{3+}$-labelled lectin-nanoparticles for detecting lectin-binding glycan epitopes of CA15-3. This was carried out as follows: 25 μl of assay buffer containing 1e$^7$ Eu$^{3+}$-NPs coated with various lectins, with additional 6 mM CaCl$_2$ for CLR (DC-SIGN, MGL, MBL, MMR), was added to each well and incubated for 2 h at RT with shaking. After the incubation, the wells were washed 6 times with the wash buffer. Time-resolved fluorescence for europium was measured (lex: 340 nm; lem: 615 nm) from dry wells using Victor3V 1420 Multilabel counter.

Example 2: Anti-CA15-3 Antibody-Lectin Nanoparticle Sandwich Assay

In these experiments, 5, 10 or 100 U/ml of BrCa cell line-purified CA15-3 (Fujirebio Diagnostics) spiked in TSA-BSA (Tris sodium azide with 7.5% BSA) was used. BrCa-associated CA15-3 was first captured with either biotinylated Ma552 or Ma695 anti-CA15-3 antibody on streptavidin-coated microtiter wells. A panel of plant or human lectins coated on Eu-doped NPs were used as tracers for screening BrCa-CA15-3 recognizing lectins as illustrated schematically in FIG. 1B and described in more detail in Example 1.

Figure 2:
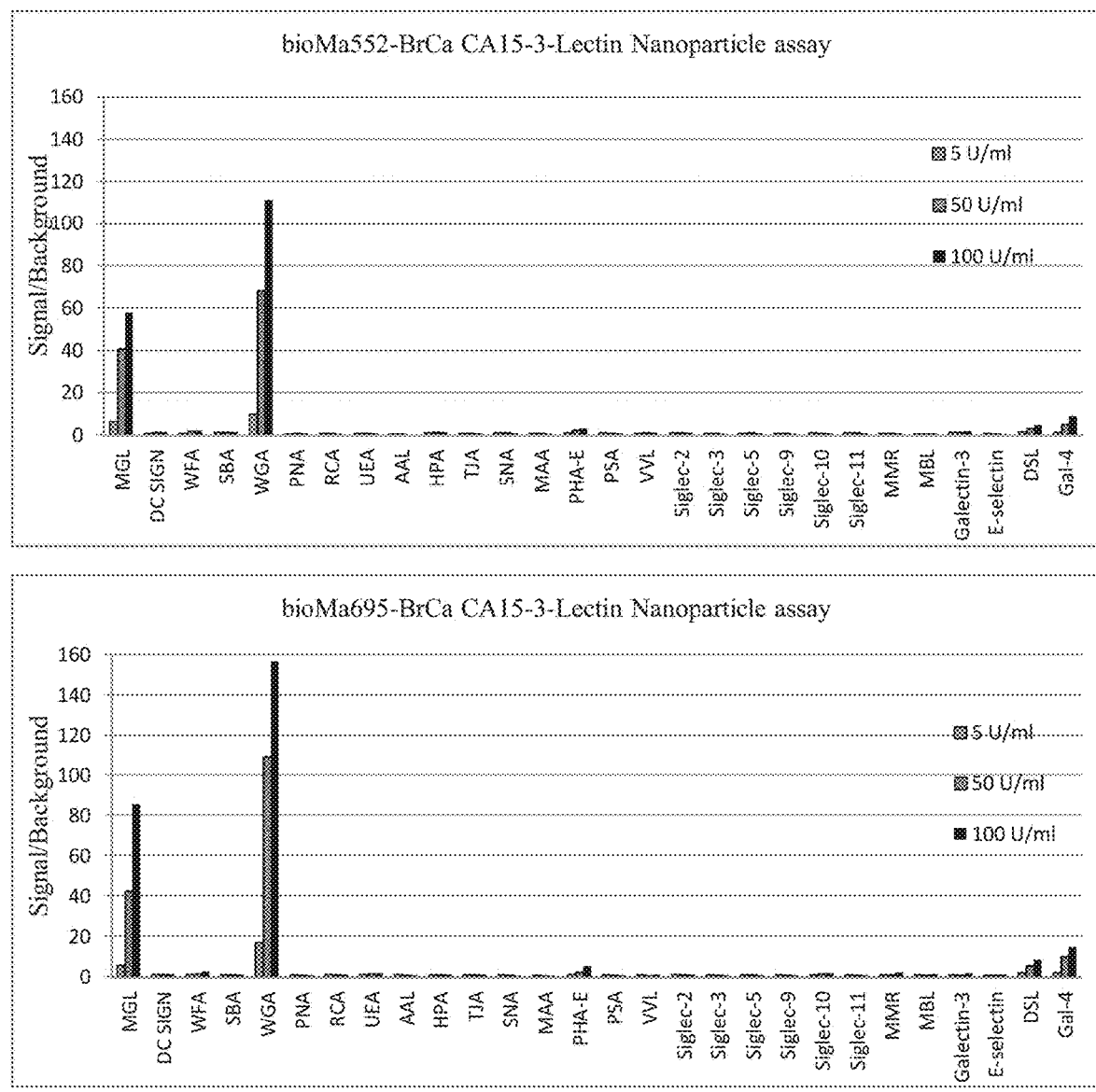
FIG. 2 shows the binding of Lectin-nanoparticles (lecting-NPs) to CA15-3 captured on A) biotinylated Ma552 Mab, or B) biotinylated Ma695 MAb. The X-axis shows different lectin-NPs used while the Y-axis shows the signal to background ratios. Only MGL and WGA lectins show significant binding with BrCa associated CA15-3.

Human lectin MGL and plant lectin WGA showed superior reactivity with BrCa-CA15-3 antigen among the lectins tested. The signal to background ratio (S/B) was more than 2 at rate of 5 U/ml with both lectin NPs (FIG. 2). Also DSL and Gal-4 showed binding to BrCa-CA15-3 but the S/B ratios were lower than with WGA and MGL. Corresponding results were obtained irrespective of whether Ma552 or Ma695 was used as the capturing antibody.

Owing to their significantly high level of binding to the BrCa-CA15-3 antigen, MGL-NPs and WGA-NPs were chosen for the development and optimization of the CA15-3 lectin assay.

Figure 3:
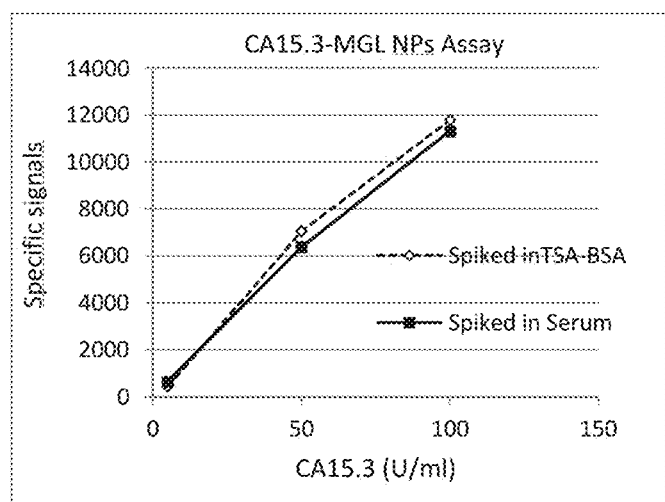
FIG. 3 demonstrates recovery rates in a CA15-3$^{MGL}$ assay. Specific signals of parallel CA15-3$^{MGL}$ assays with BrCa associated CA15-3 spiked either in a simple matrix (TSA-BSA) or a complex matrix, namely serum were compared. Excellent recovery was observed both in spiked buffer and spiked pooled healthy male serum (>95%) with excellent extrapolated analytical sensitivity (1 U/ml).

Next, recovery of BrCa-derived CA15-3 in a complex matrix, namely human serum was determined. For this purpose, 5 to 100 U/ml of CA15-3 was spiked in parallel in either healthy male pooled serum or in simple TSA-BSA buffer. CA15-3 was first captured with biotinylated Ma552 or Ma695 mAb on streptavidin microtiter plates and, after washing, finally traced with MGL-NPs to see the recovery rate. Excellent recovery (95-110%) with extrapolated analytical sensitivity 1 U/ml was achieved (FIG. 3). The results indicate that the inherent serum components do not interfere with the assay.

Figure 4:
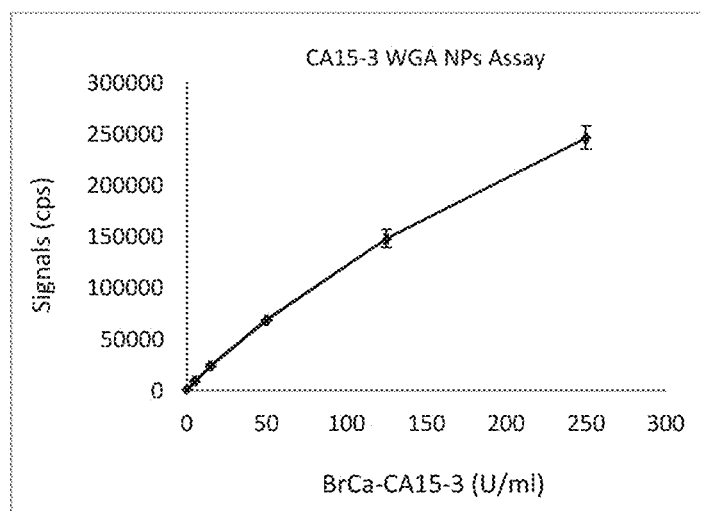
FIG. 4 shows a dose response curve for CA15-3$^{WGA}$ assay in pooled and spiked healthy male serum. Five to 250 U/ml of CA15-3 from BrCa cell line was captured on biotinylated Ma552 Mab. WGA-NPs were used as tracer. The extrapolated detection limit was 1 U/ml of BrCa associated CA15-3.

Equally excellent recovery and analytical sensitivity was observed with WGA-NPs (FIG. 4). In these experiments, 5 to 250 U/ml of BrCa-derived CA15-3 was spiked in pooled serum from healthy males, biotinylated Ma552 was used as the capturing antibody, and WGA NPs were used as tracers.

Figure 5:
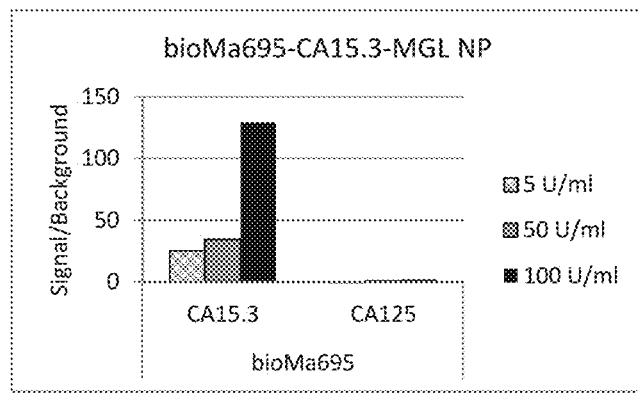
FIG. 5 demonstrates cross reactivity of capture MAbs. CA15-3$^{MGL}$ assay shows no cross reactivity with OvCa-CA125 when anti-CA15-3 MAb, either bioMa695 (A), or Ma552 (B), is used as capture. The CA125$^{MGL}$ assay shows 10-fold less binding with BrCa-associated CA15-3 compared with OvCa-associated CA125 when anti CA125 bioOv197 MAb was used as a capturing agent (C).
Figure 5:
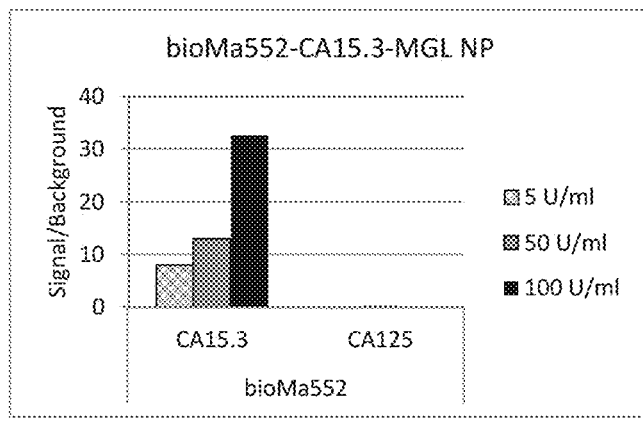
Figure 5:
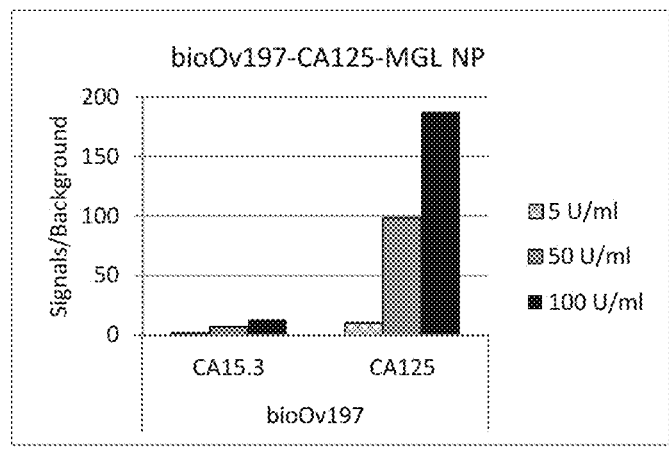

To confirm the accuracy of the results, cross-reactivity of the antibodies used in the CA15-3$^{MGL}$ assay and CA125$^{MGL}$ assays were tested (FIG. 5). No cross reactivity with ovarian cancer-derived CA125 was found in the CA15-3$^{MGL}$ assay, wherein anti-CA15-3 MAb was used as the capturing agent (FIGS. 5A and 5B). On the other hand, some cross-reactivity with BrCa-CA15-3 antigen was observed in a CA125$^{MGL}$ assay, wherein anti-CA125 MAb was used as a capturing antibody. A 10-fold difference between the measured concentrations of CA125 and CA15-3 was detected (FIG. 5C).

Example 3: Analyses of Clinical Samples

Figure 6:
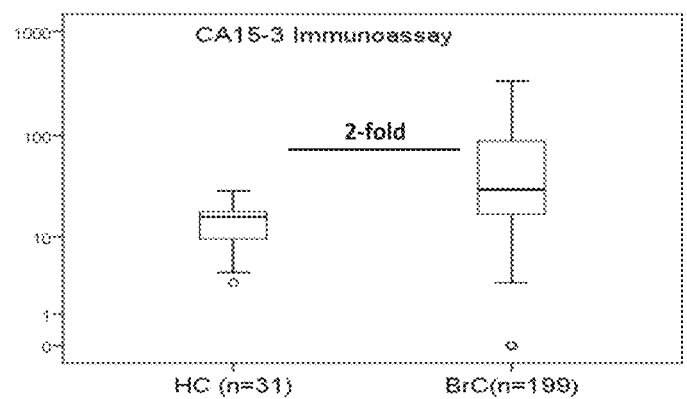
FIG. 6 shows a Box plot analysis of conventional CA15-3 immunoassay (A) and CA15-3$^{MGL}$ assay (B and C) between breast cancer (BC) patients and healthy controls (HC). All longitudinal BC samples (n=199) from 45 different BC patients were compared with samples from 31 HC. CA15-3$^{MGL}$ assay 1 is based on Ma552 (B), while CA15-3$^{MGL}$ assay 2 is based on Ma696 MAb (C) as the capturing agents. Fold differences between the median concentrations measured in the BC and HC groups are given within the figures. The line is not indicative of the fold difference.
Figure 6:
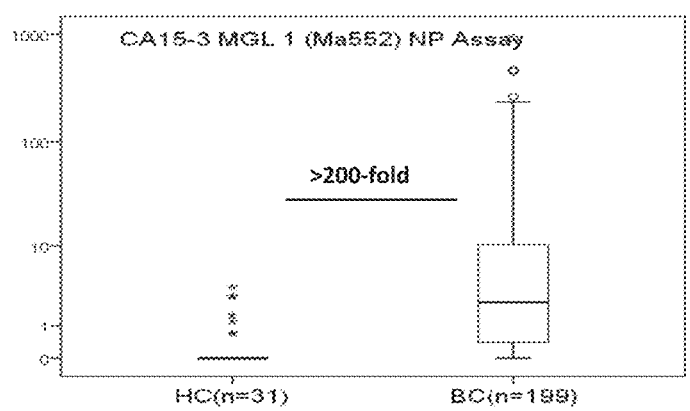
Figure 6:
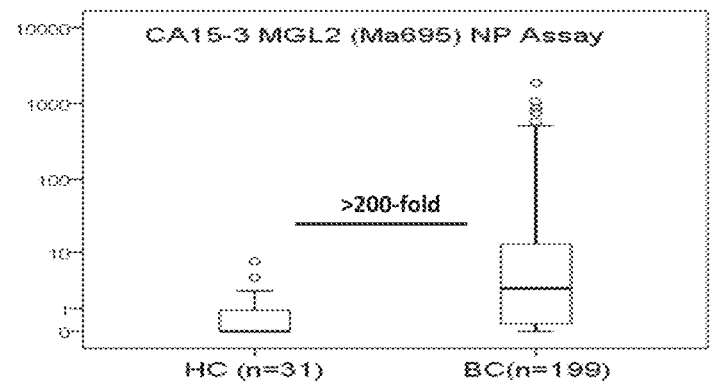

In order to test whether or not the results obtained with breast cancer cell line-based CA15-3 antigen could be translated into clinical context, a small cohort of clinical samples was analysed side by side with the present lectin-NP assay and the conventional CA15-3 immunoassay.
Box Plot Analyses Box Plot analyses of clinical breast cancer samples (n=199 from 45 different breast cancer patients) and healthy controls (n=31) with respect to their CA15-3 protein content (conventional) and CA15-3$^{MGL}$ glycoform content are shown in FIGS. 6A to 6C. According to the results, the conventional CA15-3 IA detected CA15-3 also in healthy women. Median 2-fold difference between healthy controls and breast cancer patients was detected with the conventional CA15-3 IA, while >200-fold difference between these clinical groups was detected with the present CA15-3$^{MGL}$ assay (FIG. 6). Corresponding results were obtained irrespective of whether Ma552 or Ma695 was used as the capturing antibody. Notably however, 77% of the healthy controls (24/31) were undetectable (i.e. 0 U/ml) with the present CA15-3$^{MGL}$ assay when Ma552 was used as the capturing antibody.

Figure 7:
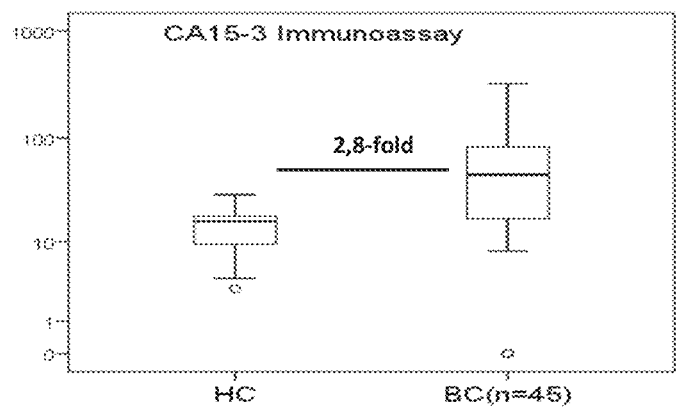
FIG. 7 shows a Box plot of conventional CA15-3 immunoassay (A) and CA15-3$^{MGL}$ assay (B and C) between breast cancer (BC) patients and healthy controls (HC). The 1st samples (n=45) among total 199 longitudinal samples from 45 different BC patients were compared with 31 HC. CA15-3$^{MGL}$ assay 1 is based on Ma552 (B), while CA15-3$^{MGL}$ assay 2 is based on Ma696, MAb as the capturing agent. Fold differences between the median concentrations measured in the BC and HC groups are shown.
Figure 7:
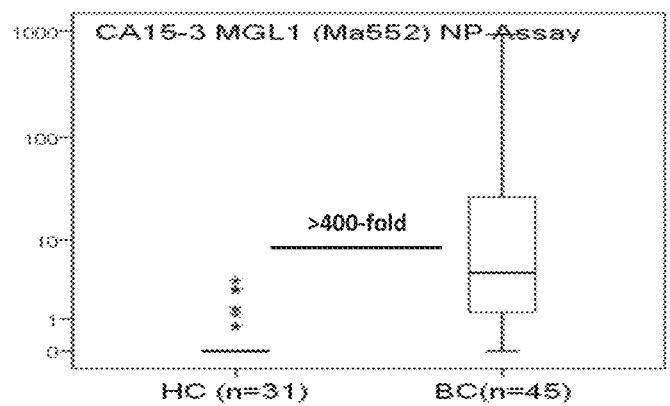
Figure 7:
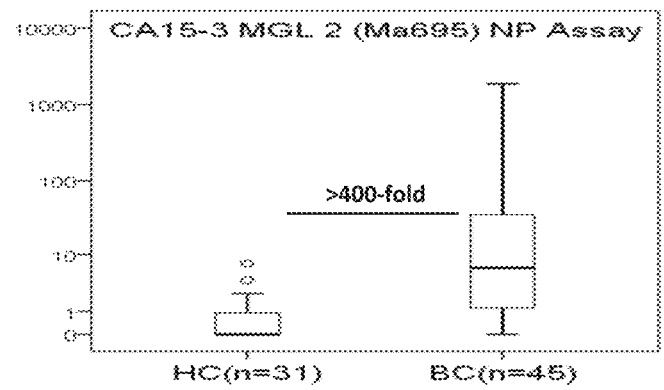

Another series of Box Plot analyses were performed using only the first serum samples for each breast cancer patient (n=45) and all control samples (n=31). In these analyses, median 2.8-fold difference between healthy controls and breast cancer patients was detected with the conventional CA15-3 IA, while >400-fold difference between these clinical groups was detected with the present CA15-3$^{MGL}$ assay irrespective of Ma552 or Ma695 was used as the capturing antibody (FIG. 7).

Figure 8:
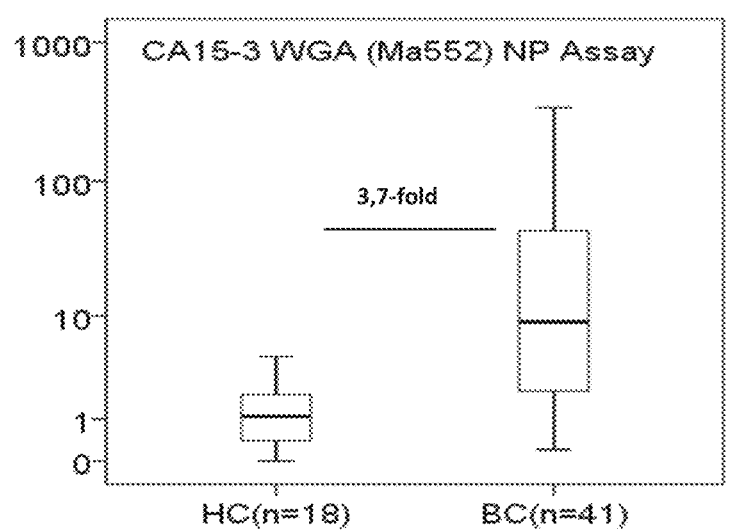
FIG. 8 shows a Box plot of CA15-3$^{WGA}$ assay between healthy controls (HC, n=18) and the first samples obtained from breast cancer patients (BC, n=41). There is a 3.7-fold difference in median between HC and BC.
Figure 9:
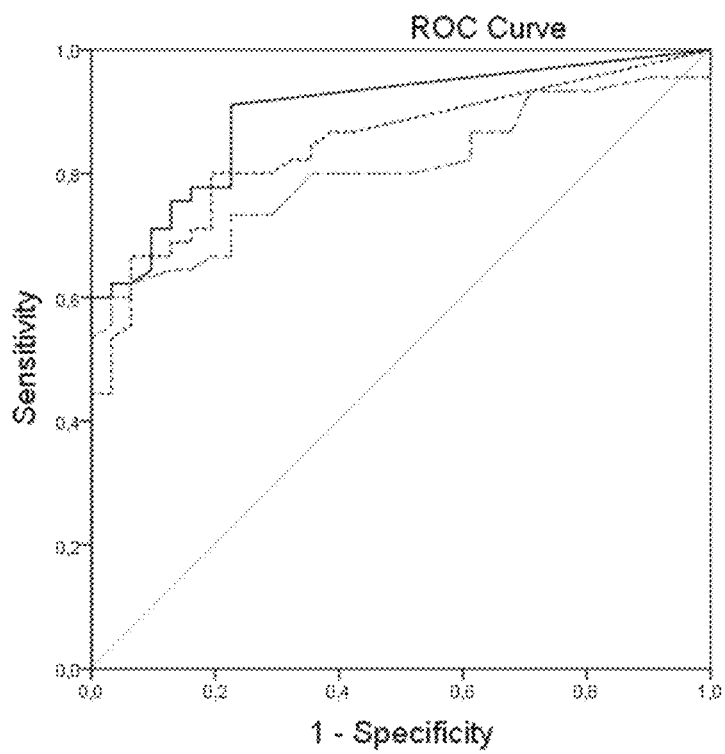
FIG. 9 shows ROC curves for all three CA15-3 assays (conventional CA15-3 immunoassay "CA153IA1st45", CA15-3$^{MGL}$ assay 1 "CA153MGL11st45" and CA15-3$^{MGL}$ assay 2 "CA153MGL21st45") generated using the first samples of BrCa patients (n=45) and healthy controls (n=31). AUC is highest for CA15-3$^{MGL}$ assay 1 (0.897), followed by CA15-3$^{MGL}$ assay 2 (0.848) and lowest for conventional CA15-3 immunoassay (0.805).
Figure 10:
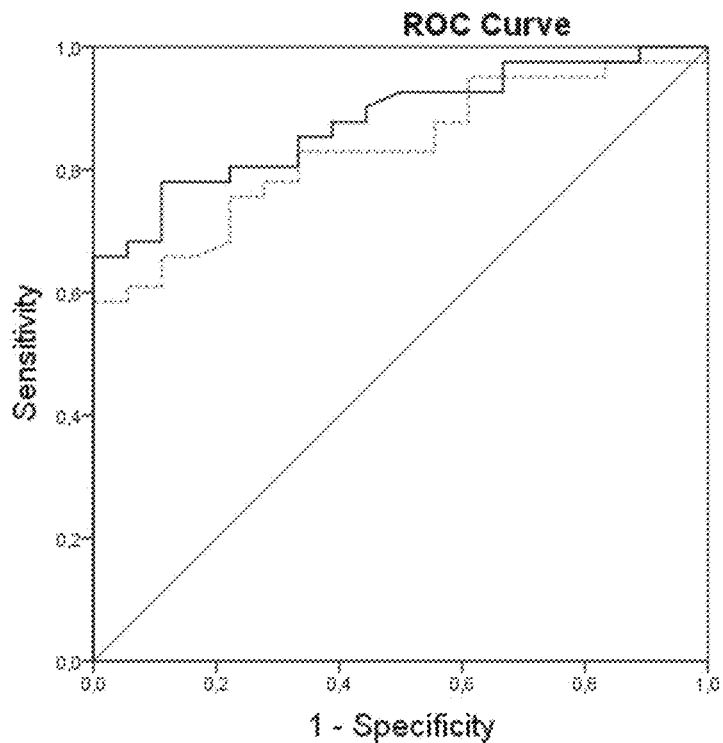
FIG. 10 shows ROC curves for conventional CA15-3 immunoassay "CA153IA1st41" and CA15-3$^{WGA}$ "CA153WGA1st41" assay generated using plasma samples of BrCa cases (n=41) and healthy women controls (n=18). AUC is higher for CA15-3$^{WGA}$ assay (0.880) than for conventional CA15-3 immunoassay (0.833).

Also the CA15-3$^{WGA}$ assay was subjected to the Box Plot analysis. For practical reasons, the first serum samples from only 41 breast cancer patient and only 18 control samples were used in the analysis. The results clearly indicate that CA15-3$^{WGA}$ can be used to distinguish breast cancer patients from healthy controls successfully (FIG. 8).
ROC Curve and AUC Analyses ROC curve analyses for discriminating breast cancer from healthy controls were performed with respect to CA15-3, CA15-3$^{MGL}$ and CA15-3$^{WGA}$. The ROC curves are shown in FIGS. 9 and 10, while the obtained AUC values are summarized below.

TABLE 2

AUC values obtained from ROC analysis performed for discriminating breast cancer (n = 45, 1$^{st}$ samples from each patient) from healthy controls (n = 31)

| Marker | AUC |
|---|---|
| CA15-3 | 0.805 |
| CA15-3$^{MGL}$ (Ma552 as the capturing antibody) | 0.897 |
| CA15-3$^{MGL}$ (Ma695 as the capturing antibody) | 0.848 |

TABLE 3

AUC values obtained from ROC analysis performed for discriminating breast cancer (n = 41, 1$^{st}$ samples from each patient) from healthy controls (n = 18)

| Marker | AUC |
|---|---|
| CA15-3 | 0.833 |
| CA15-3$^{WGA}$ | 0.880 |

According to the results, both CA15-3$^{MGL}$ and CA15-3$^{WGA}$ assays were able to discriminate better between breast cancer patients and healthy controls than the conventional CA15-3 immunoassay.
Assessment of Success Rates Success rates for markers CA15-3, and CA15-3$^{MGL}$ were determined regarding the breast cancer cases (n=45, the first sequential sample from each patient). Each serum sample was classified either as negative or positive for each marker using the following cut-off values: 25 IU/ml for CA15-3, and 2 IU/ml for CA15-3$^{MGL}$,

TABLE 4

Distribution of serum samples of breast cancer patients (n = 45) on the basis of their marker positivity or negativity

| | | CA15-3$^{MGL}$ NP Assay | | |
|---|---|---|---|---|
| | | Positive | Negative | |
| CA15-3 IA | Positive | 24 | 3 | 27 (60.0%) |
| | Negative | 8 | 10 | 18 (40.0%) |
| | | 32 (71.5%) | 13 (28.8%) | |

Figure 11:
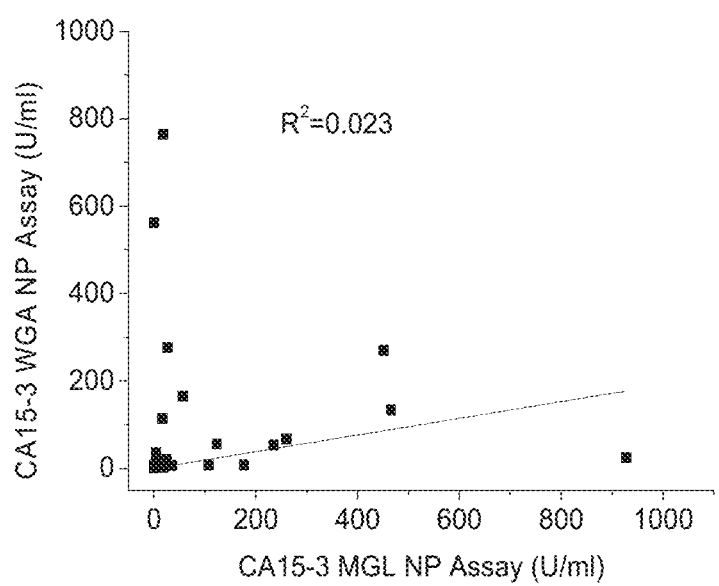
FIG. 11 demonstrates correlation between CA15-3$^{MGL}$ and CA15-3$^{WGA}$ assays. Poor correlation between the assays in all 41 plasma samples from BrCa patients was observed, indicating that the assays recognize different epitopes of the captured CA15-3.

These results indicate that in the clinical cohort employed, the success rate of CA15-3$^{MGL}$ for correctly identifying breast cancer patients as afflicted individuals is superior (71.5%) as compared with that of the conventional CA15-3 immunoassay (60%). Combined used of the assays improved the success rate to 77%.
Correlations Between Different Assays As shown in FIG. 2, both MGL and WGA when immobilized on Eu (III) nanoparticles (CA15-3$^{MGL}$ and CA15-3$^{WGA}$ assays, respectively) were able to recognise BrCa-associated CA15-3. However, the results did not correlate well when the assays were applied on clinical samples (FIG. 11). This result indicates that the glycosylation pattern of CA15-3 may vary between different breast cancer patients, and that assaying for both CA15-3$^{MGL}$ and CA15-3$^{WGA}$ may enhance sensitivity by decreasing the false negative rate.

Figure 12:
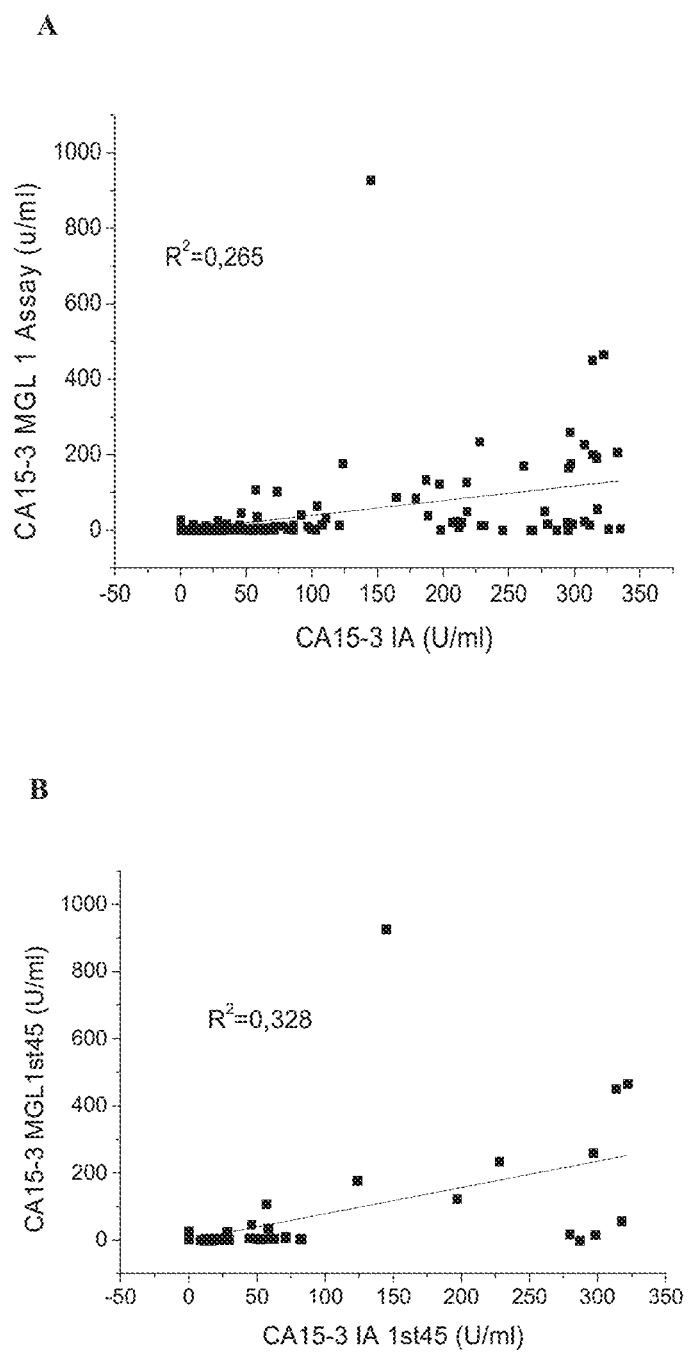
FIG. 12 demonstrates correlation between conventional CA15-3 IA and CA15-3$^{MGL}$ assay. Poor correlation between the assays in (A) all (n=199) longitudinal breast cancer patients samples as well as in (B) first samples (n=45) was observed indicating that the assays recognize different epitopes of the captured CA15-3.

Furthermore, the correlation between the CA15-3$^{MGL}$ assay and the conventional CA15-3 immunoassay (IA)

seemed very poor ($R^2=0.26$) in clinical samples from BrCa patients (n=199) as demonstrated in FIG. 12. Again, this result indicates that each of the assays detect CA15-3 differently but may be used to complement each other.

Figure 13:
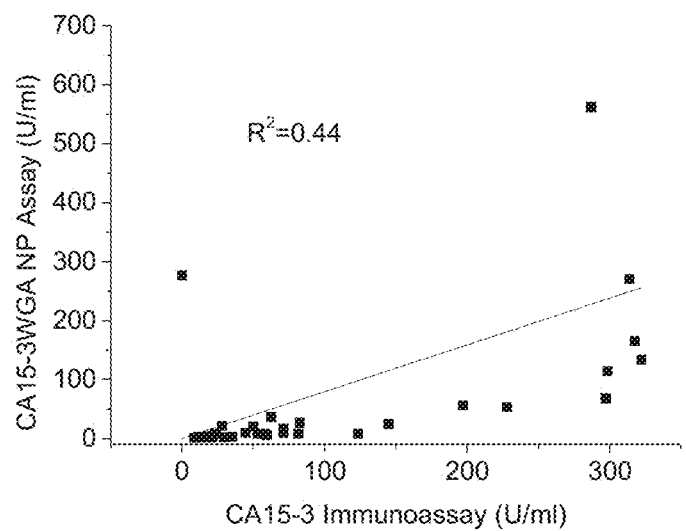
FIG. 13 demonstrates correlation between conventional CA15-3 IA and CA15-3$^{WGA}$ assay. Poor correlation between the assays in 41 plasma samples from BrCa patients was observed, indicating that the assays recognize different epitopes of the captured CA15-3.

Also, the CA15-3$^{WGA}$ assay correlated poorly with the conventional CA15-3 immunoassay (FIG. 13). However, the correlation was better than the correlation between the CA15-3$^{MGL}$ assay and the conventional CA15-3 immunoassay.

Example 4. Further Analyses of Clinical Samples

A cohort metastatic breast cancer patients and healthy controls were analysed for CA15-3$^{WGA}$ and CA15-3$^{MGL}$ either by immobilizing the lectins onto detectable nanoparticles or by direct Eu-chelate labelling.

CA15-3$^{WGA}$ and CA15-3$^{MGL}$ Eu Nanoparticle Assay

Figure 14:
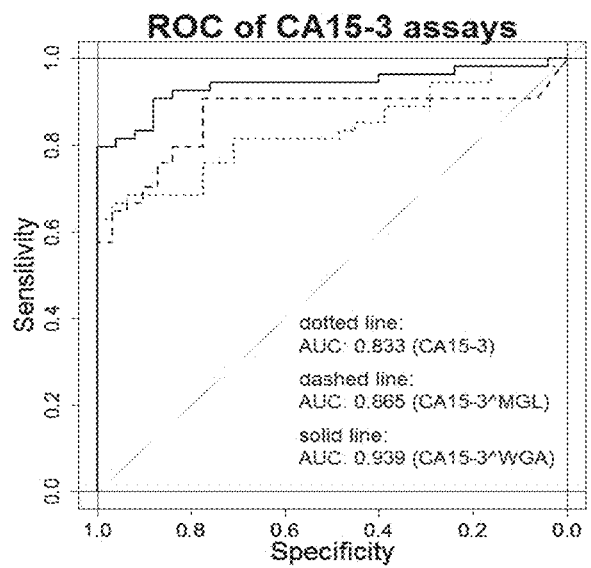
FIG. 14 shows ROC curves and AUCs of three assays of Example 4, namely the conventional CA15-3 (AUC=0.833), CA15-3$^{MGL}$ (AUC=0.865) and CA15-5$^{WGA}$ (0.939) assays using plasma samples of metastatic breast cancer cases (n=54) and healthy women controls (n=23).

ROC curves were generated for both lectins as NP based biomarkers and conventional CA15-3 assays, using baseline metastatic breast cancer patient's plasma samples (n=54) and healthy women as control (n=23) samples. AUC (Area under Curve) of both lectin-based biomarkers assay seemed to be superior over conventional assay (AUC=0.833), and best with CA125$^{WGA}$ (0.939) (FIG. 14). Thus, this new CA15-3-lectin (MGL and WGA) nanoparticle concept can substantially increase the clinical sensitivity without affecting specificity compared to the conventional CA15-3 immunoassays.

CA15-3 WGA-Eu Chelate Based Assay

Of the numerous lectins nanoparticles investigated, merely recombinant human MGL and plant lectin WGA NPs showed good potential for detection of BCa cell line associated-CA15-3 glycoforms. As the performance of WGA NPs assay was superior over MGL NPs assay, and also because the WGA is a plant lectin and much cheaper than recombinant MGL, WGA was directly labelled with soluble Eu-chelates. Directly labelled WGA performed equally well as the WGA nanoparticle (see the tables below).

It is well known that lectins have a poor affinity. Thus, Eu-NPs were used to increase their binding affinity through avidity effect. However, at least WGA performs extremely well with soluble Eu-chelate labelling (without requiring affinity improvement). Without being limited to any theory, this might be due to the good affinity of WGA itself, and also because the WGA-reactive glycan epitope (GlcNAc) can be present at several positions on CA15-3, being a large 200-1000 kDa glycoprotein. Thus, many molecules of WGA-Eu chelates can bind with single CA15-3 resulting a sensitivity close to that of WGA-NPs.

TABLE 5

Signal to background ratio of CA15-3 WGA NPs and CA15-3 WGA Eu-chelates. Both assays seem to be equally sensitive

| CA15.3 (U/ml) | WGA NPs | WGA Eu-chelate |
| --- | --- | --- |
| 5 | 5.2 | 2.7 |
| 50 | 26.2 | 16.7 |
| 100 | 45.9 | 34.3 |

TABLE 6

Signals from a pool of BrCa samples and healthy samples as controls (HC) with CA15-3 WGA NPs and CA15-3 WGA Eu-chelates. The ratio of BrCa and HC are very similar in both assays

| | CA15-3 WGA NPs | CA15-3 WGA Eu-chelate |
| --- | --- | --- |
| Background | 1 238 | 1 320 |
| Pooled Healthy control plasma (HC) | 7629 | 2 440 |
| Pooled BrCa plasma | 92060 | 36 823 |
| Ratio BrCa/HC | 12.1 | 15.1 |

Figure 15:
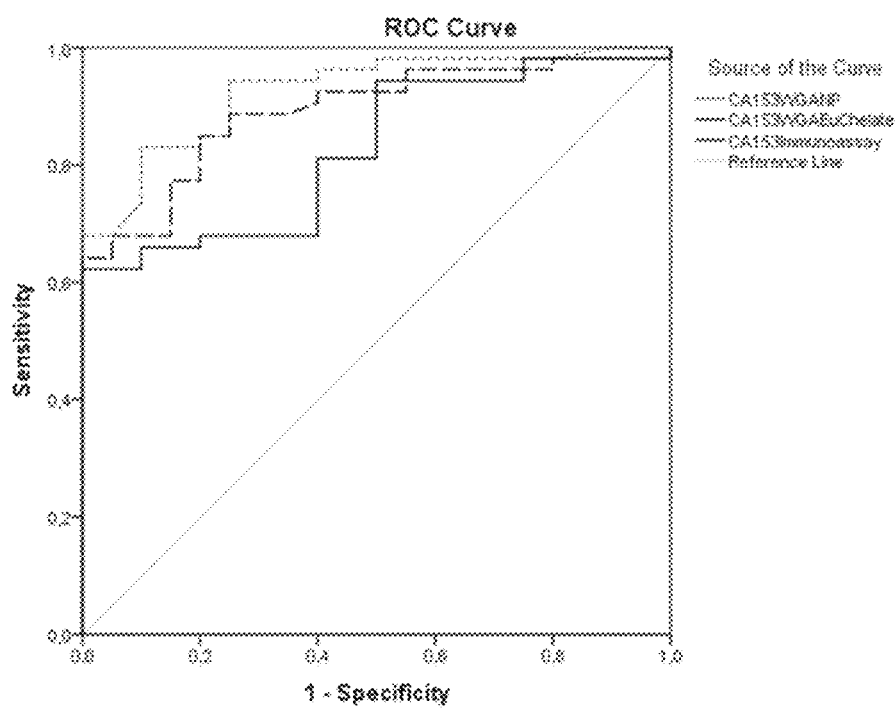
FIG. 15 shows ROC curves and AUC of three assays of Example 4, namely, the conventional CA15-3 (AUC=0.826), CA15-3$^{WGA}$ Eu-chelates labelled assay (AUC=0.890), and Eu nanoparticle CA15-3$^{WGA}$ assay (0.926).

ROC curves were generated for CA15-3$^{WGA}$ NPs, CA15-3$^{WGA}$-Eu-chelate based biomarkers and conventional CA15-3 assays, using baseline metastatic breast cancer patient's plasma samples (n=53) and healthy women as control (n=20) samples. AUC (Area under Curve) of WGA-based biomarkers assay either nanoparticle or Eu-chelates labelled were superior over conventional assay (AUC=0.826). The best performance was obtained with Eu-nanoparticle based CA15-3$^{WGA}$ (0.926). However, the AUC of Eu-chelate based CA15-3$^{WGA}$(AUC=0.890) was close to nanoparticle based assay (AUC=0.926) (FIG. 15).

Colorectal Cancer

Example 5. CEA Glycovariant Lectin-Nanoparticle Assays for Colorectal Cancer

Materials and Methods

Clinical Samples

EDTA plasma samples from colitis patients (n=14), and colorectal cancer patients (n=34) were purchased from Auria biobank (Turku, Finland). Of the colorectal cancer (CRC) patients, 23 EDTA samples were taken prior to the treatment, and they were analyzed as an entity and compared to EDTA plasma samples from colitis patients using the developed CEA glycovariant lectin-nanoparticle assays and a commercial CEA immunoassay (Fujirebio Diagnostics Ltd., Göteborg, Sweden). EDTA plasma from CRC patients having CEA<5 ng/ml (n=23) were compared to healthy volunteers (n=11) having CEA in the same range.

Materials

Human DC-sign (Dendritic cell specific intercellular adhesion molecule 3-grabbing non-integrin) fused with human IgG$_1$ Fc (Immunoglobulin G$_1$ fragment, chrystallizable) and human MBL (mannose binding lectin) were purchased from R&D Systems, Inc. (Minneapolis, Minnesaota, United States). Human MGL (macrophage galactose-type lectin) was from Sino Biological, Inc. (Beijing, China). Anti-CEA mAb (monoclonal antibody) 12-140-1 and one preparation of CEA were acquired from Fujirebio Diagnostics Ltd. (Göteborg, Sweden). Anti-CEA mAb T84.66 and a CEA preparation were kind gifts from Kjell Nustad at Norwegian Radium Hospital (Oslo, Norway). Another CEA preparation was purchased from Hytest Ltd. (Turku, Suomi). Yellow streptavidin-coated 96-well microtiter plates were specially made by Kaivogen Ltd. (Turku, Finland). RED assay buffer was purchased from Kaivogen Ltd. DELFIA plate shaker, DELFIA plate washer, and Victor™ fluorometer were manufactured by Wallac Oy (Turku, Finland). Bromelain solution ID-diluent 1 was from DiaMed (Cressier FR, Switzerland). NAP-5 and NAP-10 buffer exchange columns were purchased from GE Healthcare (Chicago, Ill., United States).

Methods

Capture Fragmentation

To yield 12-140-1 Fab$_2$ (fragment, antigen binding) antibody fragments, buffer of 12-140-1 mAb (1.15 mg) was exchanged to 0.9% NaCl using a NAP-5 column and digested by incubating with of ID-diluent 1 (50 μl per 1 mg mAb) for two hours in reaction buffer (50 mM Tris-HCl, pH 7.0, 100 mM NaCl, 3 mM EDTA) at +37° C. The digestion was stopped by adding 0.2 M N-ethylmaleimide (NEM) for a final concentration of 0.02 M NEM. The Fab2 antibody fragments were purified using protein G affinity purification.

Biotinylation

Buffers of fragmented and whole anti-CEA mAbs were exchanged to 0.9% NaCl. The antibodies were conjugated with biotin by adding a 40-time molar excess of BITC (biotin isothiocyanate) and 1/10 of total reaction volume of 500 mM Na$_2$CO$_3$ buffer (pH 9.8). The reaction was incubated for four hours at RT, away from direct light. The mixtures were purified with two rounds of buffer exchanges to TSA buffer (50 mM Tris-HCl, pH 7.75, 150 mM NaCl, 0.05% NaN$_3$) and 1% DTPA(diethylenetriaminepentaacetic acid)-treated BSA (bovine serum albumin) was added to all mixtures.

Preparation of Biotinylated 12-140-1 Fab$_2$ Spots

Biotinylated 12-140-1 Fab$_2$ (30 μg/mL) were printed in an array-in-well format onto the yellow streptavidin-coated 96-well microtiter plates (Kaivogen, Finland) with a Nano-Plotter noncontact microdispensing instrument (GeSiM, Germany) by using settings: 70% humidity, pulse 50 μs, voltage 90 V, delay 250 μs, frequency 100 Hz. Printing buffer contained phosphate buffered saline (pH 7.4) with 10% (v/v) glycerol.

Lectin Nanoparticle Assays

The lectins were coated on europium-doped nanoparticles as described in Example 1. All assays were performed on yellow streptavidin-coated 96-well microtiter plates. Triplicates in total volume of 25 μl per well were used in all assay incubations, which were performed at RT in slow shaking. The CEA standard was prepared by mixing together equal amounts of all three CEA preparations and diluting the mixture to 200, 100, 50, 15, 5, 2, and 0 ng/ml concentrations in TSA-BSA buffer (50 mM Tris-HCl, pH 7.75, 150 mM NaCl, 0.05% NaN3, 0.1% BSA). Biotinylated mAbs 12-140-1 and T84.66 were added 50 ng per well in RED assay and immobilized by incubating for one hour for use as captures in MBL and DC-sign assays, respectively. Biotinylated 12-140-1 Fab$^2$ as spots in streptavidin-coated microtiter plates were used as a capture in human MGL assay. The samples and standards were diluted 5 times in buffer A (50 mM Tris-HCl, pH 7.75, 175 mM CaCl$_2$, 350 mM NaCl, 37.5 U/ml heparin, 100 μM DTPA, 0.01% Tween 40, 0.5 mg/ml bovine γ-globulin, 5 mg/ml BSA) for MBL and DC-sign assays and buffer B (50 mM Tris-HCl, pH 7.75, 175 mM CaCl$_2$), 350 mM NaCl, 5 μg/ml native mouse IgG, 5 μg/ml HBR-2, 5 μg/ml MAK-33, 105 U/ml heparin, 100 μM DTPA, 0.01% Tween 40, 0.5 mg/ml bovine γ-globulin, 5 mg/ml BSA) for human MGL assay. After washing the wells twice, the samples and standards were added and incubated for one hour. Lectin nanoparticles were diluted in RED assay buffer with 3 mM CaCl$_2$ added for MBL and DC-sign assays and 12 mM CaCl$_2$ added for human MGL assay. The lectin nanoparticle concentrations added were 20×10$^6$, 15×10$^6$, and 35×10$^6$ particles per well for MBL, DC-sign and MGL assays, respectively. The wells were washed twice and the nanoparticle solutions added. The plates were incubated for two hours and washed six times. Time-resolved fluorescence of europium was measured at 615 nm wavelength using 340 nm excitation wavelength. The measurement cycle was 1000 μs with 400 μs delay and 400 μs measurement window time.

Results

Figure 16A:
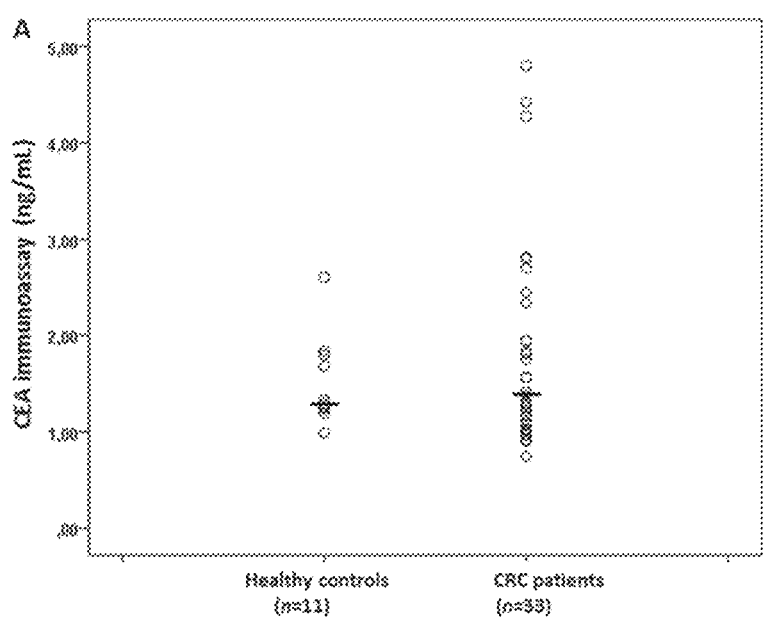
FIGS. 16A-C show a comparison of conventional CEA immunoassay (FIG. 16A) and CEA$^{DC\text{-}Sign}$ (FIG. 16B) and CEA$^{MGL}$ (FIG. 16C) glycovariant assays from CRC patients (both untreated and under treatment at the time of sampling) and healthy controls having plasma CEA<5 ng/ml.
Figure 16B:
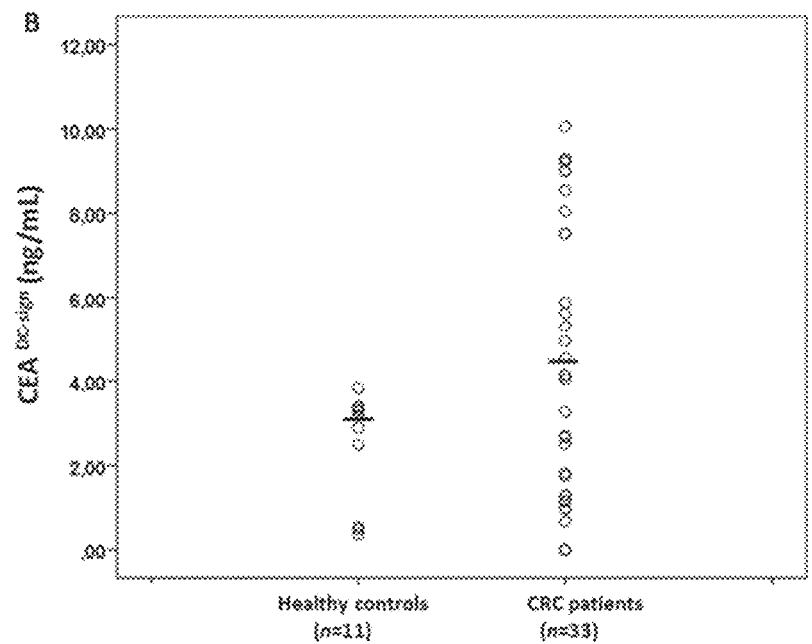
Figure 16C:
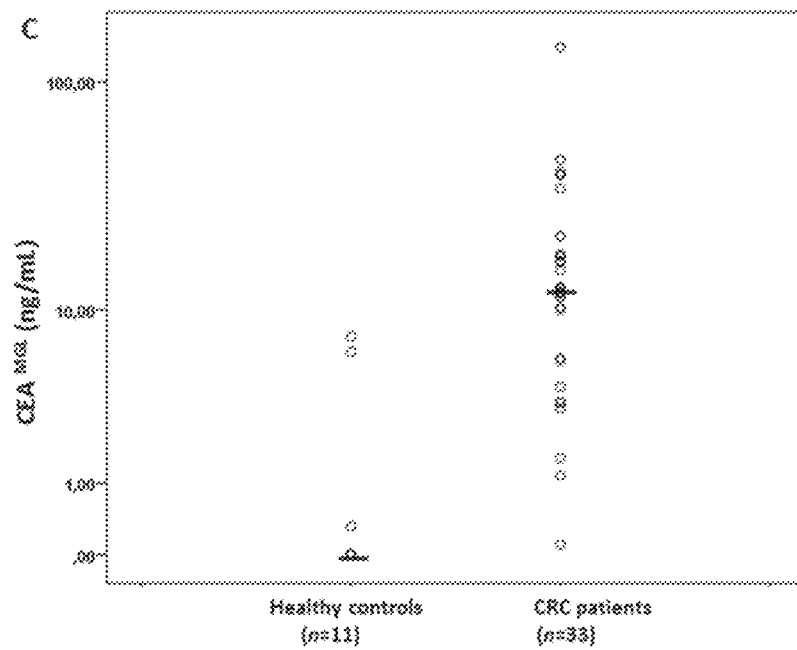

EDTA plasma from CRC patients having CEA<5 ng/ml were compared to healthy volunteers having CEA in the same range using commercial CEA immunoassay and the CEA$^{DC\text{-}Sign}$ and CEA$^{MGL}$ glycovariant assays (FIG. 16). CRC patients and healthy controls having plasma equivalent CEA levels were differentially detected with the lectin glycovariant CEA assays, with increased amount of CEA glycoforms in CRC. Seven of the healthy controls were undetectable with CEA$^{MGL}$ assay.

Figure 17A:
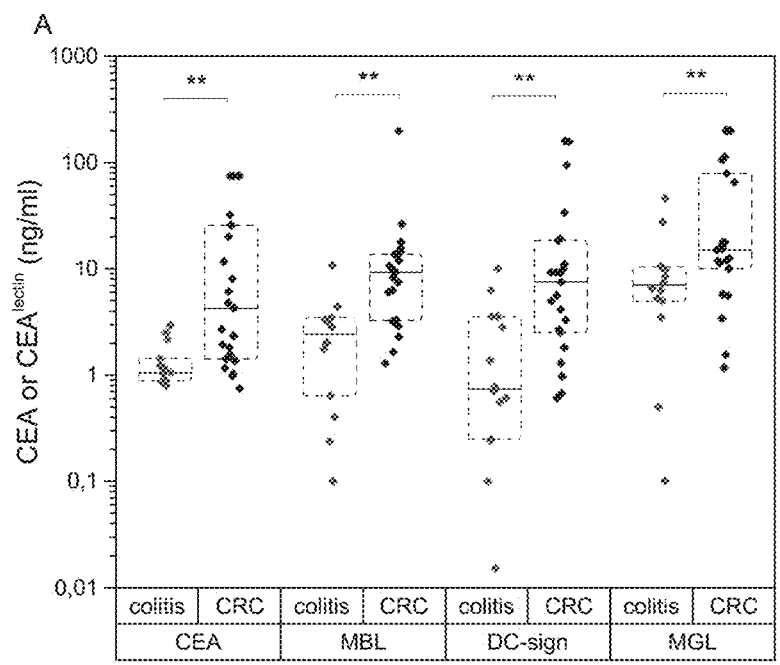
FIGS. 17A-B show CEA levels measured with the conventional and lectin CEA assays in colitis and CRC patients (FIG. 17A).
Figure 17B:
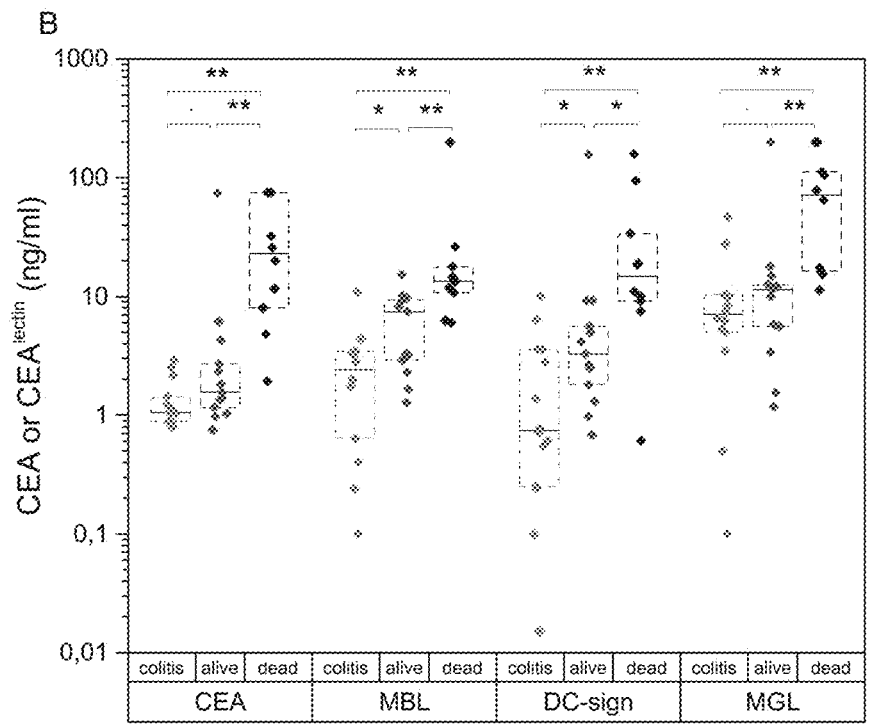

The conventional CEA values from patients with colitis or CRC were plotted (FIG. 17). Mann-Whitney's U-test with 95% confidence interval was the test used for determining statistical significance. The differences between the two groups in FIG. 17A with all the assays were significant. When using the commercial CEA immunoassay, only ten out of the 23 CRC patients (having the sampling prior to treatment) had plasma CEA value above the reference range of 5 ng/ml, and 13 CRC patients being false-negatives. The glycovariant CEA assays enabled to decrease the number of false-negatives to 6 with CEA$^{MBL}$ and CEA$^{MGL}$ assays and to 8 with CEA$^{DC\text{-}Sign}$ assay.

When the CRC group was divided into the subgroups, the patients alive (n=13) after follow-up and the patients dead (n=10) after follow-up (FIG. 17B), all except the differences between the colitis group and "alive" group with conventional CEA and MGL assay remained significant.

Figure 18:
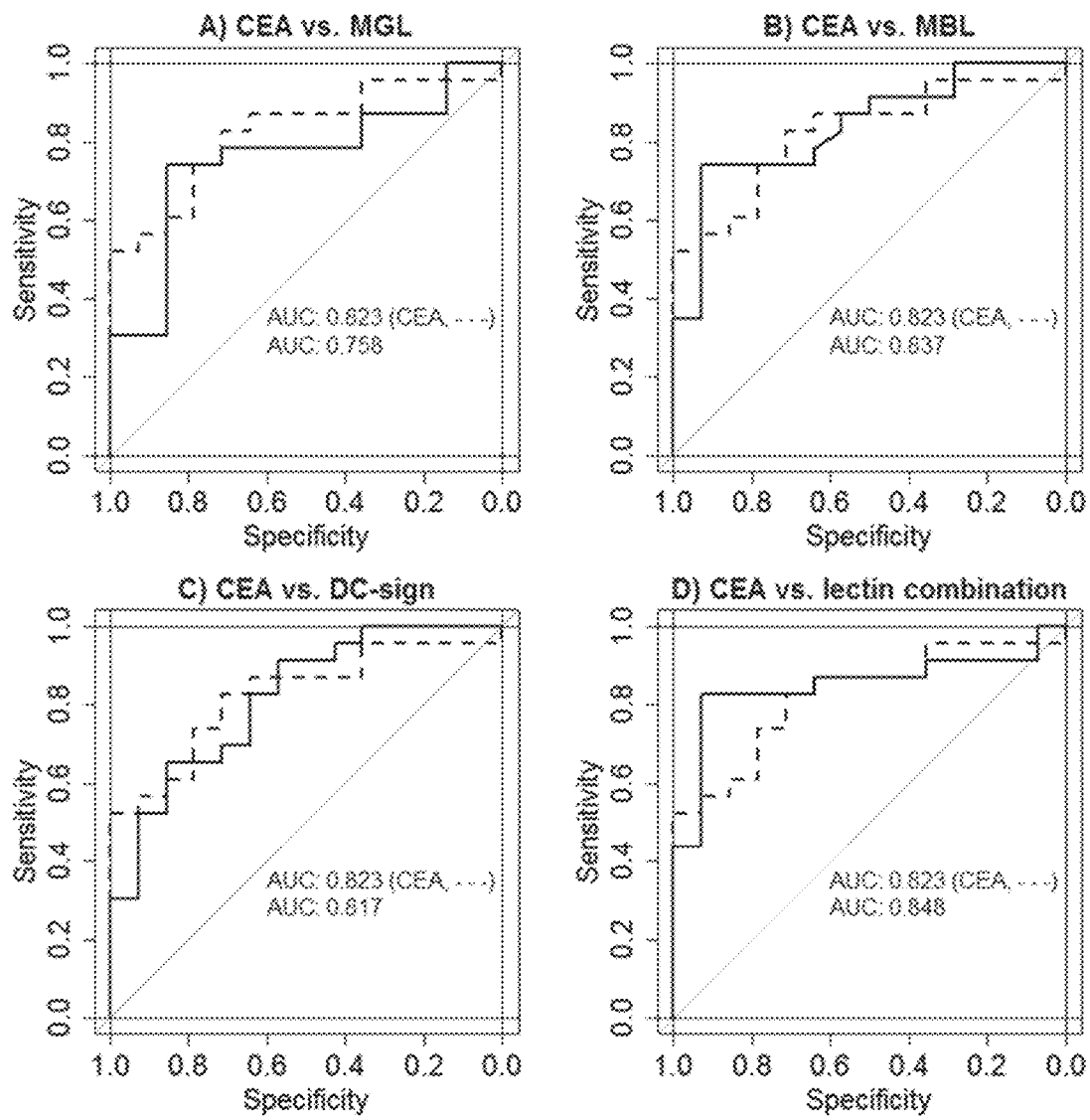
FIG. 18 shows ROC curves for plasma CEA of the MGL, MBL and DC-sign lectin assays in comparison to the conventional CEA immunoassay. ROC was performed for EDTA plasma CEA of colorectal cancer patients (n=23) and patients with colitis (n=14). The dashed line presents the conventional CEA immunoassay and solid line to lectin CEA assays.
Figure 19A:
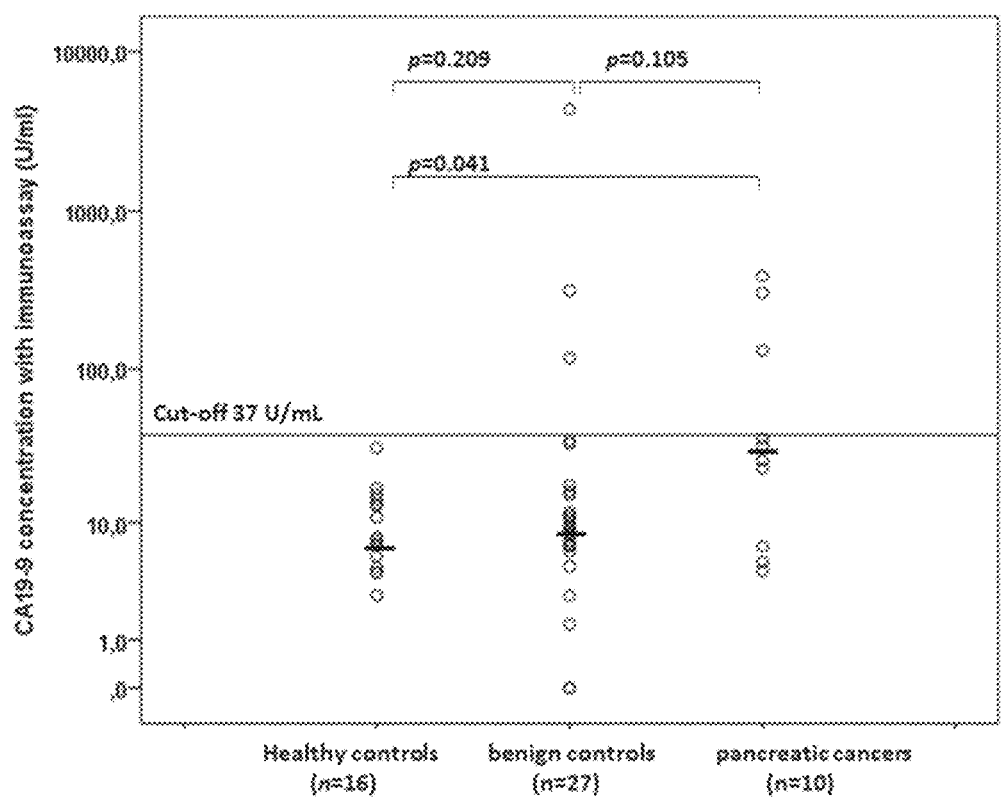
FIG. 19A shows plasma CA19-9 concentrations (U/mL) measured with the commercial CA19-9 immunoassay. Only three of the pancreatic cancer samples had CA19-9 concentrations above the cutoff 37 U/mL. No statistically significant difference observed in the median CA19-9 concentrations between pancreatic cancer patients (n=10) and benign controls (n=27). The short horizontal bars present the median CA19-9 values.
Figure 19B:
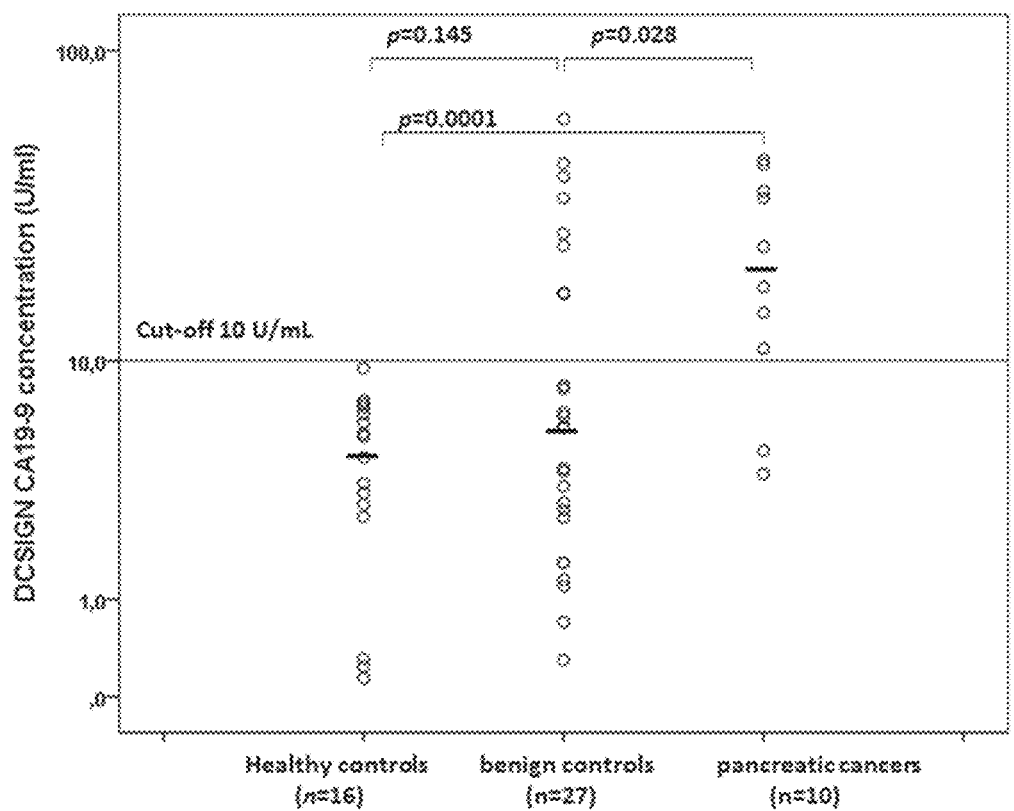
FIG. 19B shows plasma glycovariant CA19-9 (i.e. CA19-9$^{DC\text{-}SIGN}$) concentrations (U/mL) measured with the CA19-9 lectin-nanoparticle assay. Plasma glycovariant CA19-9 concentrations are elevated in pancreatic cancer and in some of the benign gastrointestinal diseases. Eight of the ten pancreatic cancer patients had plasma glycovariant CA19-9 concentrations above the cutoff 10 U/mL. There was a statistically significant difference in the median glycovariant CA19-9 concentrations between pancreatic cancer patients (n=10) and healthy controls as well as benign controls (n=27). The short horizontal bars present the median CA19-9 values.

The ROC (receiver operating characteristics) was calculated for all the assays (FIG. 18). The AUC (area under curve value) was 0.823 for the conventional CEA assay. The AUCs of MBL assay and a regression model combining the values of the three lectin assays were higher than the conventional assay's, 0.837 and 0.848, respectively. The AUCs of MGL and DC-sign assays were lower than the conventional assay's, 0.758 and 0.817, respectively.

Among the 32 lectins tested, MBL, DC-SIGN and MGL showed the highest reactivity for cancerous CEA antigen and low backgrounds in EDTA plasma.

Improvement with Lectin CEA Assays Compared to the Commercial CEA Immunoassay

The different glycovariant CEA assays (CEA$^{DC\text{-}Sign}$, CEA$^{MGL}$ or CEA$^{MBL}$) can to improve the colorectal cancer specificity of CEA tumor marker. CRC patients and healthy controls having plasma CEA levels in the normal range were differentially detected with the lectin glycovariant CEA assays, with increased amount of CEA glycoforms in CRC. The number of false-negatives significantly decreased using CEA$^{DC\text{-}Sign}$, CEA$^{MGL}$ or CEA$^{MBL}$ assay.

Pancreatic Cancer

Example 6. CA19-9 Glycovariant Lectin-Nanoparticle Assay

Materials and Methods

Clinical Samples and Control Samples

EDTA plasma from 16 healthy young volunteers were collected at the Department of Biotechnology, University of Turku with appropriate permissions and informed consents. EDTA plasma samples from 11 control samples from patients diagnosed with gastrointestinal diseases and where elevated CA19-9 levels are frequently measured, were purchased from Auria Biobank (Turku Finland). Out of these controls five patients were diagnosed having fibrosis and cirrhosis of liver, two patients having chronic hepatitis, one patient with alcoholic liver disease, three patients diagnosed as having other diseases of biliary tract. Additional EDTA plasma samples from 16 controls with CA19-9 value>5 U/mL (ranging up to 4852 U/mL) and no incidence of cancer, of any kind, as well as 10 samples from pancreatic cancer patients were purchased from Auria Biobank. Of the pancreatic cancer patients, eight were classified as having an adenocarsinoma, one having neuroendocrine carcinoma and two a metastatic carcinoma. The 11 patients with gastrointestinal diseases and 16 controls with CA19-9>5 U/mL were all considered as benign controls.

Materials

Anti-CA19-9 mAb (monoclonal antibody) c241 was acquired from Fujirebio Diagnostics Ltd. (Göteborg, Sweden). Human DC-sign (Dendritic cell specific intercellular adhesion molecule 3-grabbing non-integrin) fused with human IgG$_1$ Fc (Immunoglobulin G$_1$ fragment, chrystallizable) was purchased from R&D Systems, Inc. (Minneapolis, Minnesaota, United States). Yellow streptavidin-coated 96-well microtiter plates were specially made by Kaivogen Ltd. (Turku, Finland). RED assay buffer was purchased from Kaivogen Ltd. DELFIA plate shaker, DELFIA plate washer, and Victor™ fluorometer were manufactured by Wallac Oy (Turku, Finland).

Same amount of CA19-9 antigen from Fujirebio Diagnostics Ltd. and HyTest Ltd. (Turku, Finland) was pooled and used as a calibrator, and dilutions of 1, 5, 10, 20, 50 100 U/mL were made in Tris-saline-azide buffer (50 mmol/L Tris, 150 mmol/L NaCl, 0.5 g/L NaN$_3$, pH 7.7) containing 5 g/L BSA, and used as triplicates.

Methods

The developed CA19-9 glycovariant lectin-nanoparticle assay was conducted in three-step sandwich-type format, where anti-CA19-9 monoclonal antibody was used as a capture and lectin-coated nanoparticles as the tracer. All subsequent steps were undertaken at room temperature and incubations done with slow shaking.

Biotinylated anti-CA19-9 monoclonal antibody c241 (75 ng/well), used as a capture antibody, was immobilized to streptavidin coated wells in 25 µL of RED assay buffer for one hour incubation. After washing twice, 5 µL of either sample or calibrator and 20 µL of Red Assay buffer with added 50 mM CaCl$_2$, in three replicas, were added and incubated for one hour. The wells were washed twise and DC-sign coupled to Eu(III)-chelate-dyed nanoparticles (1.0×10$^7$ particles/well) were added in 30 µl of RED assay buffer with 12.5 mM CaCl$_2$ added. After incubating the nanoparticles for two hours, the wells where washed six times and the TRF of the bound nanoparticle bioconjugates was directly measured from the surface of the well.

A commercial CA19-9 immunoassay kit (Fujirebio Ldt) was used as a reference method to compare the developed CA19-9 glycovariant lectin-nanoparticle assay.

Results

With the CA19-9 glycovariant lectin-nanoparticle assay the median concentration for pancreatic cancer patients was 20.8 U/mL (interquartile range: 9.45, 38 U/mL), for benign patients 5.9 U/mL (interquartile range: 2.6, 16.8 U/mL) and for healthy volunteers 4.9 U/mL (interquartile range: 2.7, 6.8 U/mL). CA19-9 glycovariant lectin-nanoparticle assay improved the discrimination of pancreatic cancer patients from healthy controls (p=0.0001) and benign controls (p=0.028) compared to the conventional CA19-9 immunoassay, where only a borderline statistically significant difference was seen between pancreatic cancer patients and healthy controls (p=0.041) (FIG. 1). There was no statistically significant difference between pancreatic cancer patients and benign controls when the conventional CA19-9 immunoassay was used (p=0.105).

Moreover, only three out of the ten pancreatic cancer patients had CA19-9 values above the recommended cutoff of 37 U/mL in the conventional CA19-9 immunoassay, resulting in 70% (7/10) of the tested pancreatic cancer patients being determined as false-negatives. Using the CA19-9 glycovariant lectin-nanoparticle assay, with the cut-off of 10 U/mL, eight out the ten pancreatic cancer patients were correctly determined as positive, significantly improving the sensitivity.

Among the 27 lectins tested, DC-SIGN showed the one of the highest reactivity for cancerous CA19-9 antigen and good performance when either EDTA plasma or serum was used.

Improvement with CA19-9 Glycovariant Lectin-Nanoparticle Assay

The CA19-9 glycovariant lectin-nanoparticle assay improved the discrimination of pancreatic cancer patients from healthy controls and benign controls, patients having benign disease of the liver or biliary tract, compared to the conventional CA19-9 immunoassay. Moreover, the CA19-9 glycovariant assay decreased the number of false-negatives, significantly improving the sensitivity.

Prostate Cancer

Example 7. PSA Glycovariant Lectin-Nanoparticle Assays

Reagents and Instrumentation

Seminal plasma PSA from healthy donors was obtained from Department of Clinical Chemistry, Lund University Hospital (Malmö, Sweden) with appropriate permissions and informed consents. Purified PSA from prostate cancer cell line, LNCaP, was from the Department of Biotechnology, University of Turku. Human MGL (macrophage galactose-type lectin) was from Sino Biological, Inc. (Beijing, China). Unconjugated WGA (Wheat germ agglutinin) was from Vector Laboratories, Peterborough, United Kingdom. Recombinant human Gal4 (Galectin 4) and Dectin 2 were from R&D Systems, Inc. (Minneapolis, Minnesaota, United States). Microtiter wells coated with streptavidin, wash buffer concentrate and RED assay buffer was purchased from Kaivogen Ltd (Turku, Finland). DELFIA plate shaker, DELFIA plate washer, and Victor™ fluorometer were manufactured by Wallac Oy (Turku, Finland).

LNCaP PSA was used as a calibrator, and dilutions (1-200 µg/L LNCaP PSA) were made in Tris-saline-azide buffer (50 mmol/L Tris, 150 mmol/L NaCl, 0.5 g/L NaN$_3$, pH 7.7) containing 5 g/L BSA, and used as triplicates.

Clinical Samples and Control Samples

Prostate tissue samples from 36 PCa patients (12 histologically benign and 24 cancerous, graded as Gleason 2-4) were obtained from radical prostatectomies (RP) immediately after surgery from Turku University Hospital, Finland. The sample tissues were stored at −20° C. in 1 ml of phosphate-buffered saline (PBS) buffer with added protease inhibitors (cOmplete tablets Roche Diagnostics, Manheim, Germany) until further processing. The protein pool from was recovered using Triton-X-100 detergent from Acros Organics, ThermoFischer Scientific (Geel, Belgium) by adding 1/10 of the sample volume of 10×PBS lysis buffer (pH 7.4, with added protease inhibitors, 20 mM EDTA, 10% Triton-X-100). The lysis was done on ice under slow shaking for two hours and the supernatant stored in −20° C. For the analysis from each sample a 1:10 dilution was done in Tris-saline-azide buffer containing 5 g/L BSA.

Urine samples were obtained from Turku University Hospital. The study cohort included consecutive 143 men with clinical suspicion of prostate cancer (PCa), enrolled in a prospective, registered IMPROD-trial (ClinicalTrials.gov identifier NCT01864135). EDTA plasma was obtained from 45 men registered in the IMPROD-trial. Urine samples from 11 male volunteers (under 35 years) were collected at the Department of Biotechnology, University of Turku.

Methods

Preparation of Biotinylated 5A10 Fab Spots

Biotinylated 5A10 Fab (100 µg/mL) was printed in an array-in-well format onto the yellow streptavidin-coated 96-well microtiter plates (Kaivogen, Finland) with a NanoPlotter noncontact microdispensing instrument (GeSiM, Germany) by using settings: 70% humidity, pulse 50 µs, voltage 90 V, delay 250 µs, frequency 100 Hz. Printing buffer contained phosphate buffered saline (pH 7.4) with 10% (v/v) glycerol.

Lectin Nanoparticle Assays for Tissue Lysates

The developed PSA$^{MGL}$ glycovariant lectin-nanoparticle assay was conducted in three-step sandwich-type format and all the incubations were performed at room temperature, in slow shaking. Biotinylated free PSA-specific recombinant Fab-fragment 5A10 (150 ng/well), used as a capture antibody, was immobilized to streptavidin coated wells in 100 µL of Red assay buffer for one hour incubation. After washing twice, 50 µL of either tissue lysate dilution or calibrator and 50 µL of Red Assay buffer with 5 µg/ml native mouse IgG, 5 µg/ml HBR-2, 5 µg/ml MAK-33 added, in triplicates, were added and incubated for one hour. The wells were washed twice and MGL coupled to Eu(III)-chelate-dyed nanoparticles (2.0×10$^7$ particles/well) were added in 100 µl of RED assay buffer with 3 mM CaCl$_2$ added. After incubating the nanoparticles for two hours, the wells where washed six times and the time-resolved fluorescence (TRF) of the bound nanoparticle bioconjugates was directly measured from the surface of the well.

Figure 20:
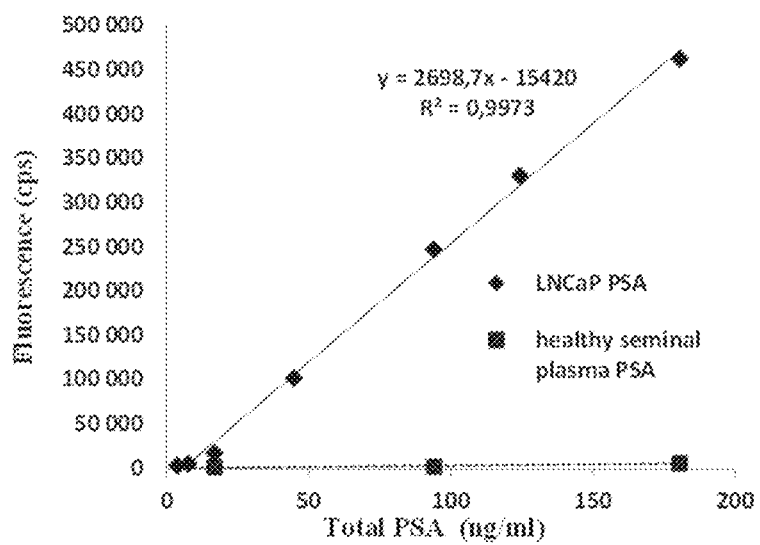
FIG. 20 shows dose response curves (mean fluorescence signals measured from triplicates) from different PSA forms with PSA$^{MGL}$ glycovariant assay. LNCaP PSA calibration curves (◇) and seminal plasma PSA from healthy donors (□).

PSA secreted by LNCaP cells and seminal plasma PSA from healthy donors were studied using the developed PSA$^{MGL}$ glycovariant lectin-nanoparticle assay. The fluorescence from different PSA forms in a concentration range of 1-180 ng/ml is shown in FIG. 20. The assay was performed as for the tissue lysates, except in the sample incubation 25 µl of different PSA concentrations and 75 µl of RED assay buffer were used.

Lectin Nanoparticle Assays for Urine and EDTA Plasma Samples

Biotinylated 5A10 Fab (100 µg/ml) spotted onto streptavidin-coated microtiter plates were used as a capture in glycovariant fPSA$^{MGL}$ assay. Biotinylated 5A10 Fab (80 ng/well) for fPSA$^{Dectin2}$ fPSA$^{WGA}$ assays and H117 mAb (120 ng/well) for total PSA$^{Gal4}$ assay were added in RED assay buffer onto streptavidin-coated microtiter plates and incubated for one hour.

After washing twice, 20 µL of either sample or calibrator and 30 µL Red Assay buffer with 5 µg/ml native mouse IgG, 5 µg/ml HBR-2, 5 µg/ml MAK-33 was added to fPSA$^{MGL}$ assay; for all the other assays 10 µl of sample or calibrator and 40 µl of assay buffer was used. The samples and calibrators were added in triplicates and incubated for 1 hour. Lectin nanoparticles were diluted in RED assay buffer with 6 mM CaCl$_2$. After washing twice, the lectin nanoparticle concentrations added were 7×10$^6$, 4×10$^7$, 5×10$^6$, and 2×10$^7$ particles per well for fPSA$^{MGL}$, fPSA$^{Dectin2}$, fPSA$^{WGA}$ and total PSA$^{Gal4}$ assays, respectively. The plates were incubated for two hours, washed six times and TRF was measured.

Results

Seminal plasma PSA from healthy donors and PSA derived from prostate cancer cell line, LNCaP, was differentially detected with the developed PSA$^{MGL}$ glycovariant assay, as the assay was only detecting the cancerous PSA (FIG. 20).

Figure 21:
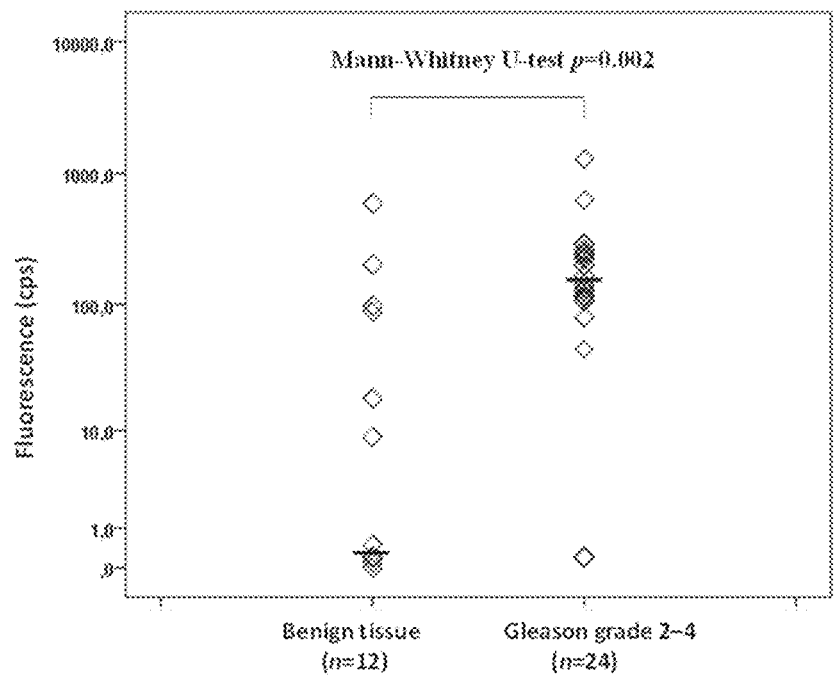
FIG. 21 shows the fluorescence signal from MGL-coupled nanoparticles measuring the PSA glycovariant in lysates from histologically benign and cancerous prostate tissue. There was a statistically significant increase in the PSA$^{MGL}$ glycovariant in cancer tissue compared to the benign tissue.

PSA from 12 benign and 24 cancerous prostate tissue lysates was studied using the nanoparticle-based lectin-immunoassay fPSA$^{MGL}$ in a whole-well format. The tumor tissue showed a statistically significant (p=0.00$^2$) increase in PSA$^{MGL}$ glycovariant compared to the benign tissue from PCa patients (FIG. 21). All the benign tissue samples were from PCa patients, but having a normal prostate tissue microscopic appearance, and most likely, altered glycosylation could have already occurred on PSA in the benign tissue, resulting in measurable fluorescence signals with the fPSA$^{MGL}$ glycovariant assay.

Figure 22:
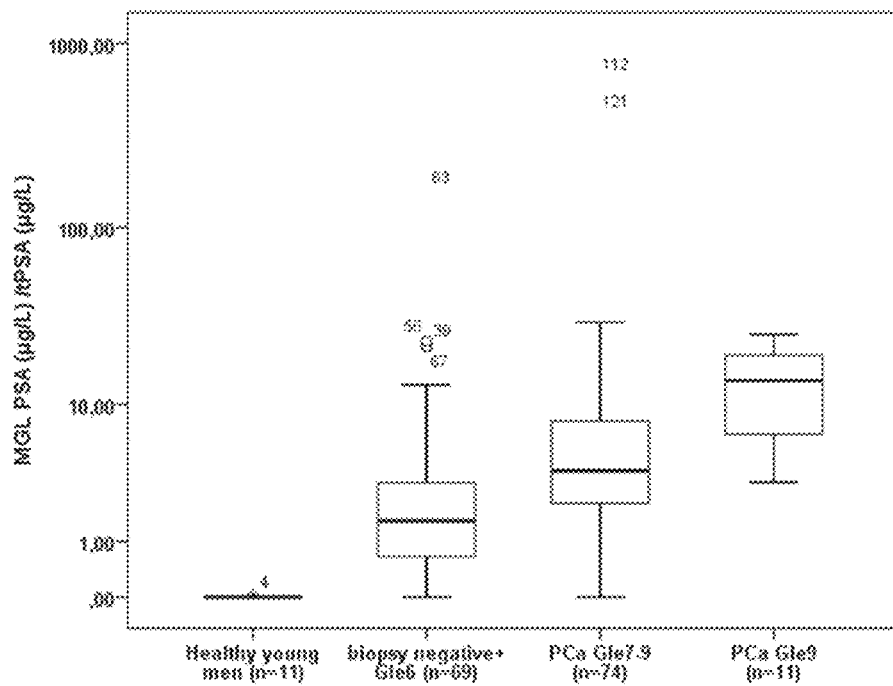
FIG. 22 shows the total PSA-corrected fluorescence signals of PSA$^{MGL}$ glycovariant assay from urine PSA from prostate cancer patients (n=74), BPH patients (n=69) and healthy young males (n=11). The tPSA-corrected fluorescence signals were calculated as the measured fluorescence from the Eu-nanoparticles, divided by tPSA-concentration in the sample. Comparing the tPSA-corrected fluorescence signal of MGL coupled nanoparticles from urine PSA between healthy young males (n=11), men with negative PCA biopsy or Gleason score 6 prostate cancer (n=69), and prostate cancer patients with Gleason score 7-9 (n=74) and Gleason score 9 (n=11). The 10/25/50/75/90$^{th}$ percentiles are marked in the figures.

Urine samples from 143 men with clinical suspicion of PCa in a prospective controlled trial (IMPROD, NCT01864135) were analyzed with the fPSA$^{MGL}$ glycovariant assay, with capture 5A10 Fab spotted onto streptavidin-coated microtiter plates. Of the 143 men, 74 were diagnosed with clinically significant PCa (Gleason score≥7), 20 men having Gleason score 6 graded PCa and 49 with a negative prostate biopsy (referred as biopsy negative). In addition urine from 11 young healthy males was included. The total PSA-corrected fluorescence signals of PSA$^{MGL}$ glycovariant assay from urine PSA are presented in FIG. 22. There was a statistically significant (p=0.006) increase in the median urine PSA glycovariant concentrations in men with clinically significant PCa compared to men having a negative PCa biopsy or Gleason score 6 PCa. Urine PSA glycovariant content seemed to be further elevated in the more aggressive Gleason score 9 prostate cancers. Urine PSA from young males was not detected using the fPSA$^{MGL}$ glycovariant assay, albeit the urine PSA concentrations were in the same range for all the groups tested. The urine PSA concentrations for patients having a clinically significant PCa, negative prostate biopsy or a Gleason 6 PCa, and healthy young men are presented in Table 7.

Figure 23A:
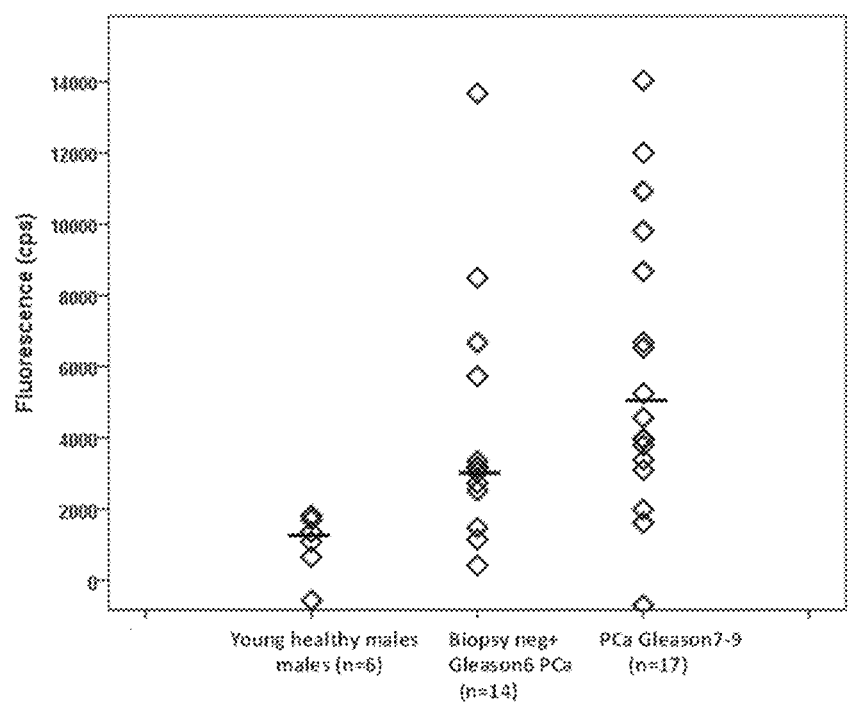
FIGS. 23A-C show fluorescence signals, as mean fluorescence signals from three replicates, in PSA$^{WGA}$ (FIG. 23A), PSA$^{GAl4}$ (FIG. 23B) and PSA$^{Dectin\ 2}$ glycovariant assay (FIG. 23C). Comparing the fluorescence signal of WGA coupled nanoparticles from urine PSA between young males (n=6) men with negative PCa biopsy or Gleason score 6 PCa (n=14) and men with clinically significant PCa (n=17) (FIG. 23A). Comparing the fluorescence signal of GAl4 coupled nanoparticles from urine PSA between young males (n=9), men with negative PCa biopsy or Gleason score 6 PCa (n=19) and men with clinically significant PCa (n=26) (FIG. 23B). Comparing the fluorescence signal of GAl4 coupled nanoparticles from urine PSA between young males (n=9), men with negative PCa biopsy or Gleason score 6 PCa (n=9) and men with clinically significant PCa (n=26) (FIG. 23C).
Figure 23B:
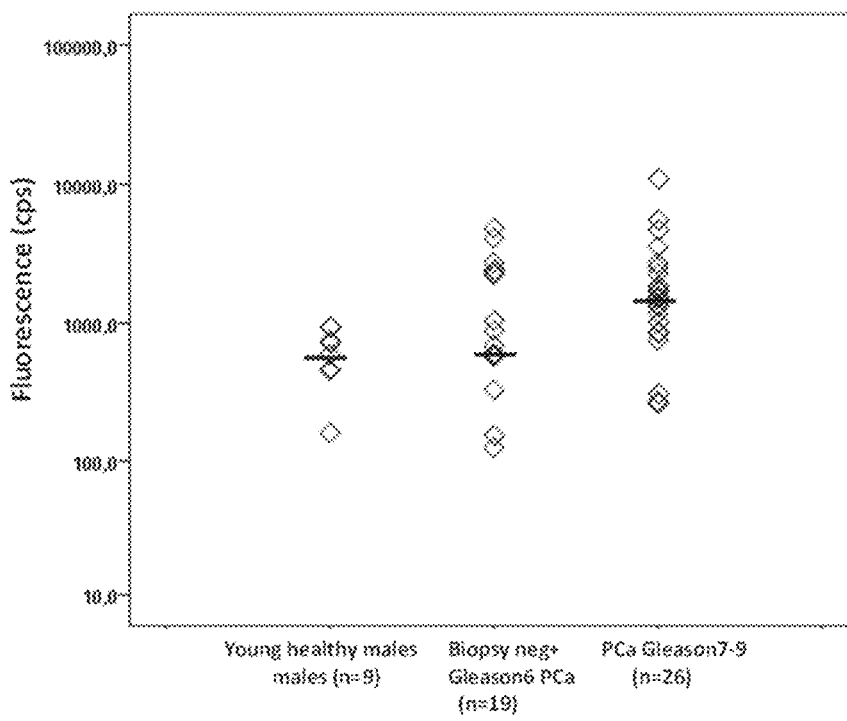
Figure 23C:
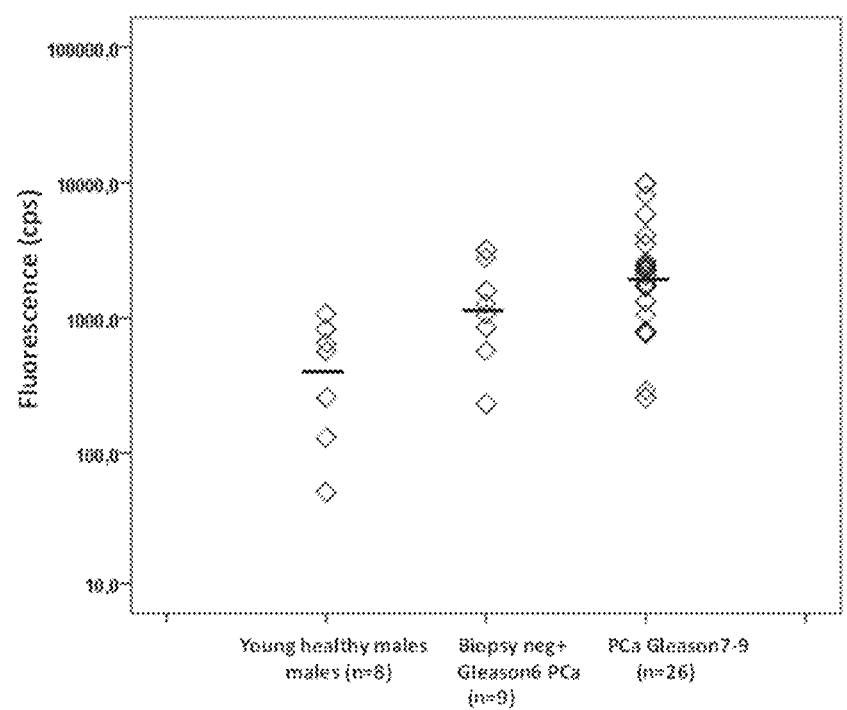

Additional PSA glycovariant assays having potential to further improve the discrimination of clinically significant prostate cancers are presented in FIG. 23. EDTA plasma from men with a confirmed PCa or with a suspicion of prostate cancer but having a negative biopsy was compared to healthy men. The PSA$^{WGA}$, PSA$^{Gal4}$ and PSA$^{Dectin2}$ glycovariant assays showed an increase in median PSA glycovariant content in men with clinically significant PCa.

Among the 30 lectins tested, MGL showed superior ability to discriminate between the cancerous and non-cancerous PSA antigen.

TABLE 1

Urine PSA concentrations (μg/L) for men with PCa, men having negative biopsies and young men

| Urine tPSA (μg/L) | Healthy young males (n = 11) | Biopsy neg. +Gle6 (n = 71) | Gle7 to Gle9 (n = 74) | Gle9 (n = 11) |
|---|---|---|---|---|
| Range | 1.2-1023 | 0.2-1309 | 0.4-1516 | 1.5-687 |
| Median | 51.9 | 112.4 | 77.2 | 43.5 |

Improvement with fPSA$^{MGL}$ Glycovariant Assay

The fPSA$^{MGL}$ glycovariant assay can improve cancer specificity of PSA and aid in discriminating patients with clinically significant PCa, as and the assay detects PSA glycoforms present in prostate cancer tissue and urine of PCa patients. The urine PSA, even when in high concentrations, from young men is undetectable with the fPSA$^{MGL}$ glycovariant assay. Using urine samples instead of blood samples has the advantage of being non-invasive and there is no need for personnel for sampling. The conventional total or free PSA immunoassays unable to differentiate as the PSA concentration range are identical in young males, PCa patients and men with negative PCa biopsy.

As the PSA$^{MGL}$ glycovariant assay is suitable for tissue lysates and urine samples, it can be applied for serum samples, as has been shown with the other tumor markers.

The invention claimed is:

1. A method for treating pancreatic cancer in a subject in need thereof, said method comprising:
   (a) assaying a sample obtained from the subject to detect a level of a Carbohydrate antigen 19-9 (CA19-9) glycoform that binds to Dendritic Cell-Specific Intercellular adhesion molecule-3-Grabbing Non-integrin (DC-SIGN), wherein the CA19-9 glycoform is CA19-9$^{DC-SIGN}$, and wherein a CA19-9 specific antibody is used as a capturing agent and DC-SIGN as a detectably labelled tracer, or wherein DC-SIGN is used as a capturing agent and a CA19-9 specific antibody as a detectably labelled tracer;
   (b) comparing the detected level of said CA19-9$^{DC-SIGN}$ in said sample with that of (i) a healthy control sample, (ii) a benign control sample, or (iii) a predetermined threshold value; and
   (c) when the detected level of said CA19-9$^{DC-SIGN}$ in said sample is increased compared to that of (i) said healthy control sample, (ii) said benign control sample, or (iii) said predetermined threshold value, treating said subject for said pancreatic cancer with surgery, radiation therapy, chemotherapy, or any combination thereof.

2. The method according to claim 1, further comprising: monitoring said pancreatic cancer, wherein said monitoring is carried out by repeating the assaying step at least twice at different time points to determine if the level of CA19-9$^{DC-SIGN}$ in said sample is increased compared to one or more earlier samples obtained from the same subject or compared to that of said healthy control sample, said benign control sample, or said predetermined threshold value.

3. The method according to claim 2, further comprising: monitoring response to treatment, monitoring relapse of said cancer, or monitoring recurrence of said pancreatic cancer.

4. The method according to claim 1, where in the assaying step comprises:
   subjecting said sample to an antibody specific for CA19-9 in order to capture CA19-9 contained in the sample;
   subjecting said captured CA19-9 to DC-SIGN; and
   measuring the level of binding of said captured CA19-9 to said DC-SIGN.

5. The method according to claim 1, wherein the assaying step comprises:
   subjecting said sample to DC-SIGN in order to capture CA19-9$^{DC-SIGN}$ contained in the sample;
   subjecting said captured CA19-19$^{DC-SIGN}$ to an antibody specific for CA19-9; and
   measuring the level of binding of said captured CA19-9$^{DC-SIGN}$ to the antibody specific for CA19-9.

6. The method according to claim 4, wherein either said DC-SIGN or said CA19-9 specific antibody is immobilized on a nanoparticle.

7. The method according to claim 1, wherein said sample is selected from the group consisting of urine, blood, serum, plasma, peritoneal cavity fluid, and tissue samples.

8. The method according to claim 1, comprising: immobilizing said DC-SIGN on a nanoparticle or labelling said DC-SIGN with a detectable label.

9. The method according to claim 6, wherein all dimensions of said nanoparticle are less than about 1000 nm.

10. The method according to claim 9, wherein said nanoparticle is selected from the group consisting of protein nanoparticles, mineral nanoparticles, glass nanoparticles, nanoparticle crystals, metal nanoparticles, plastic nanoparticles, polystyrene nanoparticles, poly (ethylene glycol) nanoparticles, polyethylene nanoparticles, poly (acrylic acid) nanoparticles, poly (methyl methacrylate) nanoparticles, polysaccharide nanoparticles, colloidal gold nanoparticles, silver nanoparticles, quantum dots, carbon nanoparticles, porous silica nanoparticles, and liposomes.

11. The method according to claim 9, wherein said nanoparticle is composed of upconverting phosphorus (UCP) or is doped with a lanthanide chelate.

12. The method according to claim 1, wherein the detected level of said CA19-9$^{DC-SIGN}$ is determined as increased if its level in said sample is at least about 1.5 times that of said healthy control sample, said benign control sample, or said predetermined threshold value.

* * * * *